United States Patent
Matsumura et al.

(10) Patent No.: US 11,524,074 B2
(45) Date of Patent: Dec. 13, 2022

(54) CANCER-CELL-SPECIFIC ANTI-TMEM-180 MONOCLONAL ANTIBODY, ANTICANCER DRUG, AND CANCER TESTING METHOD

(71) Applicants: National Cancer Center, Tokyo (JP); RIN Institute Inc., Tokyo (JP)

(72) Inventors: Yasuhiro Matsumura, Tokyo (JP); Masahiro Yasunaga, Tokyo (JP); Shinji Saijou, Tokyo (JP); Shingo Hanaoka, Tokyo (JP)

(73) Assignees: National Cancer Center, Tokyo (JP); RIN Institute Inc., Tokyo (JP)

( * ) Notice: Subject to any disclaimer, the term of this patent is extended or adjusted under 35 U.S.C. 154(b) by 382 days.

(21) Appl. No.: 16/578,861

(22) Filed: Sep. 23, 2019

(65) Prior Publication Data

US 2020/0078458 A1 Mar. 12, 2020

Related U.S. Application Data

(62) Division of application No. 15/509,269, filed as application No. PCT/JP2015/075425 on Sep. 8, 2015, now Pat. No. 10,471,146.

(30) Foreign Application Priority Data

Sep. 8, 2014 (JP) ................. 2014-182760
Dec. 24, 2014 (JP) ................. 2014-260727

(51) Int. Cl.
| | | |
|---|---|---|
| A61K 39/395 | (2006.01) | |
| C07K 16/30 | (2006.01) | |
| C07K 16/18 | (2006.01) | |
| G01N 33/574 | (2006.01) | |
| A61K 39/00 | (2006.01) | |

(52) U.S. Cl.
CPC .... *A61K 39/39558* (2013.01); *A61K 39/0011* (2013.01); *C07K 16/18* (2013.01); *C07K 16/30* (2013.01); *C07K 16/3046* (2013.01); *G01N 33/574* (2013.01); *G01N 33/57419* (2013.01); *C07K 2317/24* (2013.01); *C07K 2317/51* (2013.01); *C07K 2317/515* (2013.01); *C07K 2317/565* (2013.01); *C07K 2317/73* (2013.01)

(58) Field of Classification Search
CPC .................................................. C07K 16/30
See application file for complete search history.

(56) References Cited

U.S. PATENT DOCUMENTS

| | | | |
|---|---|---|---|
| 8,623,829 B2 | 1/2014 | Tsunoda et al. | |
| 2011/0195848 A1 | 8/2011 | Roopra et al. | |
| 2011/0244501 A1 | 10/2011 | Chu et al. | |
| 2012/0114704 A1 | 5/2012 | Feinstein | |
| 2013/0280276 A1 | 10/2013 | Watanabe et al. | |
| 2016/0009799 A1 | 1/2016 | Satofuka et al. | |
| 2019/0060480 A1* | 2/2019 | Matsumura ............ | C12N 15/62 |

FOREIGN PATENT DOCUMENTS

| | | |
|---|---|---|
| EP | 2177615 A1 | 4/2010 |
| WO | 2013133450 A1 | 12/2013 |
| WO | 2014041185 A1 | 3/2014 |

OTHER PUBLICATIONS

Portolano (The Journal of Immunology, vol. 150, No. 3, p. 880-887, 1993) (Year: 1993).*
Harris (Biotechnology, vol. 11, p. 1293-1297, 1993) (Year: 1993).*
Rudikoff et al (Proc. Natl. Acad. Sci. USA, 79(6):1979-1983, 1982) (Year: 1982).*
Colman P. M. (Research in Immunology, 145:33-36, 1994) (Year: 1994).*
Clark, et al., "The Secreted Protein Discovery Initiative (SPDI), a Large-Scale Effort to Identify Novel Human Secreted and Transmembrane Proteins: A Bioinformatics..", Sep. 1, 2003, pp. 22652270, vol. 13, No. 10, Publisher: Genome Research.
Cunningham, et al., "Cetuximab Monotherapy and Cetuximab plus Irinotecan in Irinotecan-Refractory Metastatic Colorectal Cancer", Jul. 22, 2004, pp. 337-345, vol. 351, Publisher: N Engl J Med.
Goldstein, et al., "Biological efficacy of a chimeric antibody to the epidermal growth factor receptor in a human tumor xenograft model", Nov. 1, 1995, pp. 1311-1318, vol. 1, No. 11, Publisher: Clin Cancer Res.
International Search Report received in PCT/JP2015/075425 dated Dec. 15, 2015.
Karapetis, et al., "K-ras Mutations and Benefit from Cetuximab in Advanced Colorectal Cancer", Oct. 23, 2008, pp. 1757-1765, vol. 359, No. 17, Publisher: N Engl J Med.
Rudikoff, et al., "Single amino acid substitution altering antigen-binding specificity", Mar. 1982, pp. 1979-1983, vol. 79, No. 6, Publisher: PNAS USA.
Tamura, et al., "Structural Correlates of an Anticarcinoma Antibody: Identification of Specificity-Determining Residues (SDRs) and Development of a Minimally Immuno . . . ", Feb. 1, 2000, pp. 1432-1441, vol. 164, No. 3, Publisher: J. Immunol.
Written Opinion received in PCT/JP2015/075425 dated Dec. 15, 2015.
Bendig et al., "Humanization of Rodent Monoclonal Antibodies by CDR Grafting", 1995, pp. 83-93, vol. 8, Publisher: Methods: A companion to Methods in Enzymology.

(Continued)

*Primary Examiner* — Michael Allen
(74) *Attorney, Agent, or Firm* — Suzannah K. Sundby, Esq.; Canady + Lortz LLP

(57) ABSTRACT

An object of the present invention is to provide an anticancer drug capable of treating cancer by finding a target molecule specifically expressed in cancer cells and by specifically acting on the target molecule, and to provide a cancer testing method including a step of measuring the target molecule in a sample. The present invention provides an anticancer drug containing, as an active ingredient thereof, an anti-transmembrane protein 180 (TMEM-180) antibody or an antigen-binding fragment thereof. In addition, the present invention provides a cancer testing method including a step of measuring the amount of TMEM-180 in a sample collected from a subject.

13 Claims, 13 Drawing Sheets

Specification includes a Sequence Listing.

(56) References Cited

OTHER PUBLICATIONS

Edris, et al., "Antibody therapy targeting the CD47 protein is effective in a model of aggressive metastatic leiomyosarcoma", Apr. 24, 2012, pp. 6656-6661, vol. 109, No. 17, Publisher: PNAS USA.
Isacke, et al., "p180, a novel recycling transmembrane glycoprotein with restricted cell type expression", Jun. 1, 1990, pp. 2606-2618, vol. 10, No. 6, Publisher: Molecular and Cellular Biology.
Notice of Reasons for Refusal received in JP2016547444 dated Aug. 16, 2019.
NCBI Reference Sequence: NM_024789.3 *Homo sapiens* transmembrane protein 180 (TMEM180), mRNA, Mar. 22, 2014 (see also current version NM_024789.4).
Palmieri, et al., "Endo180 modulation by bisphosphonates and diagnostic accuracy in metastatic breast cancer", Jan. 15, 2013, pp. 163-169, vol. 108, No. 1, Publisher: Br J Cancer.
Paul et al., "Fundamental Immunology Third Edition", 1993, pp. 292-295, Publisher: Raven Press, NY.

* cited by examiner

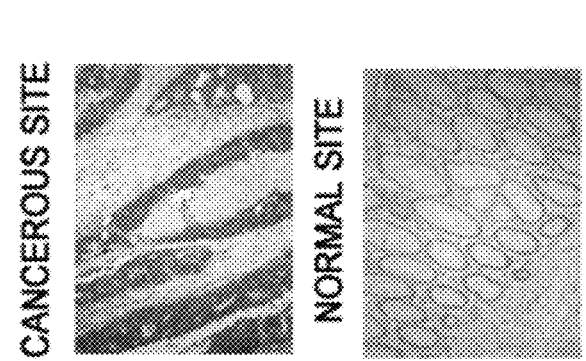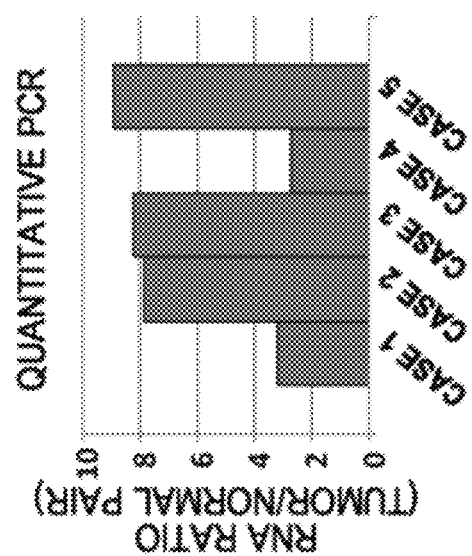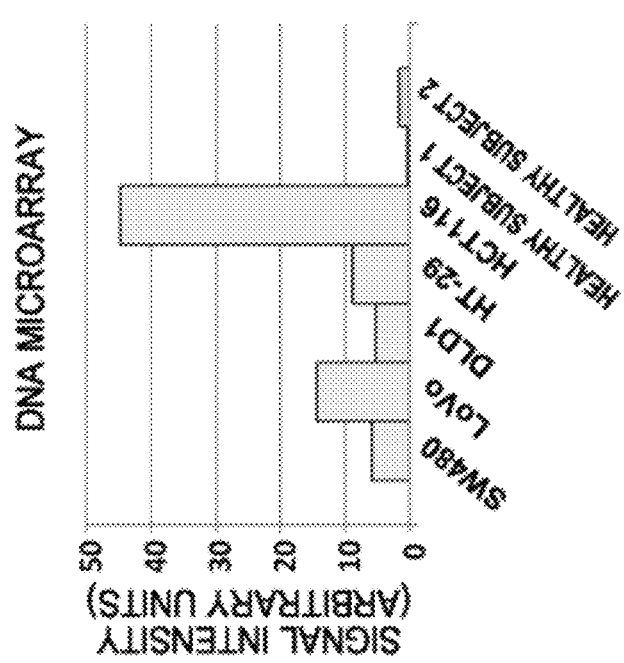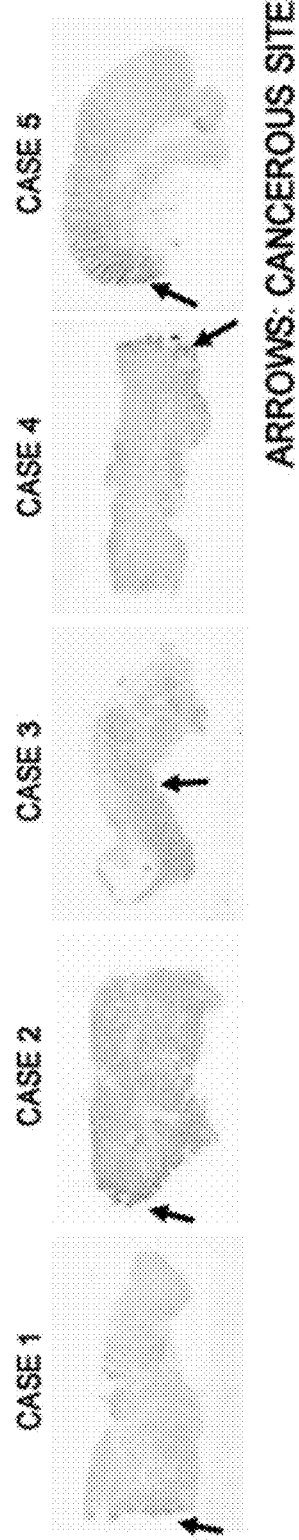

COLON CANCER CELL-POSITIVE ANTIBODY
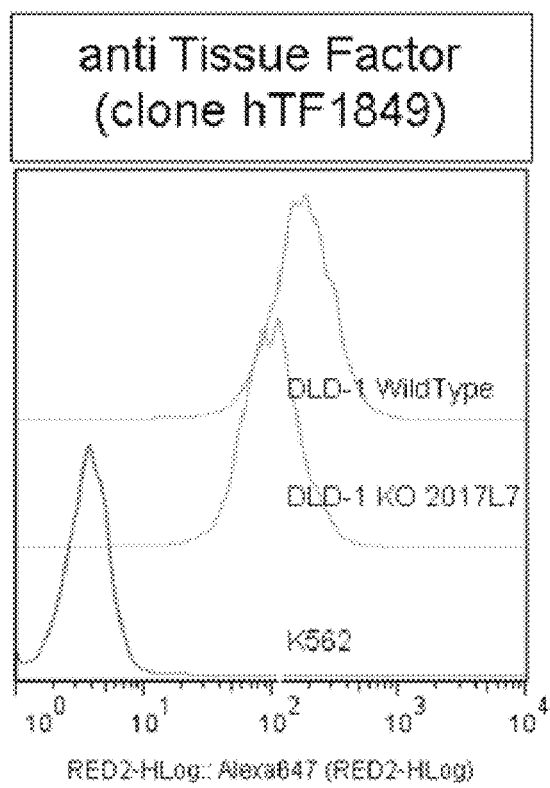
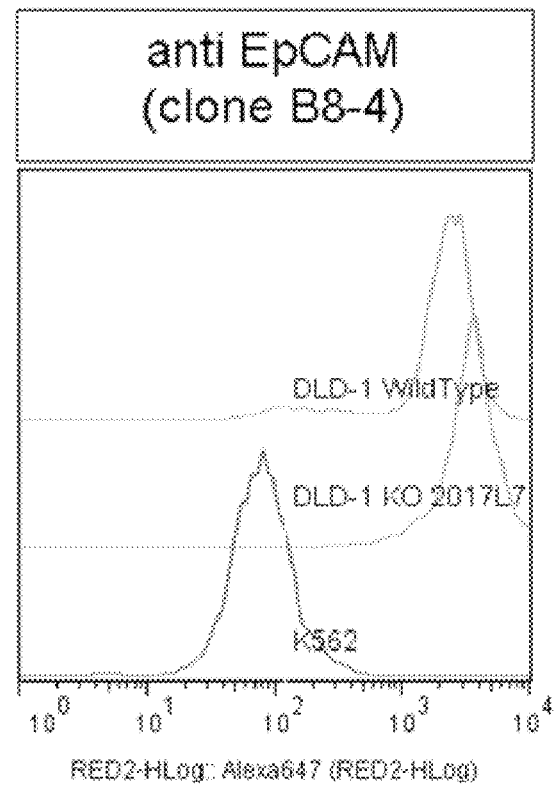
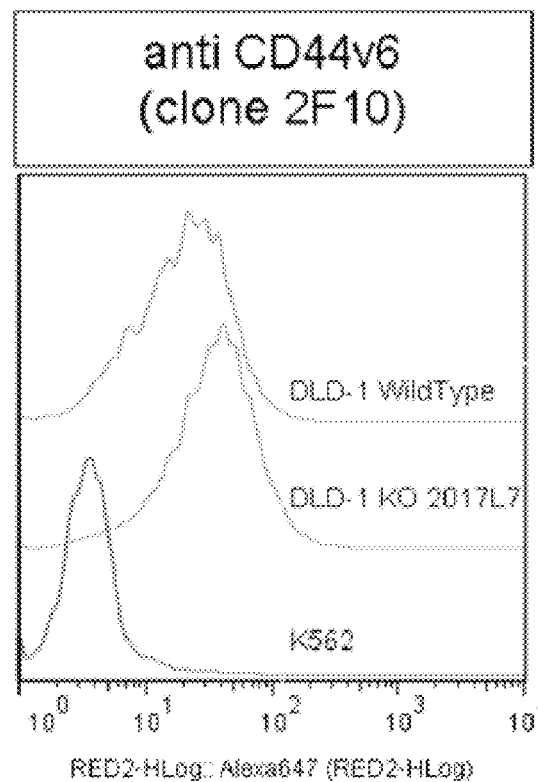
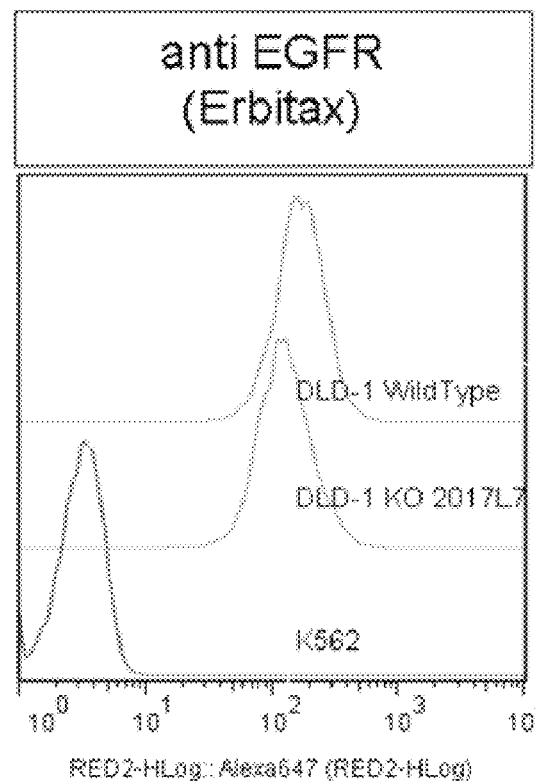
Fig. 5 cont.

SEQUENCE LISTING

```
<160> NUMBER OF SEQ ID NOS: 170

<210> SEQ ID NO 1
<211> LENGTH: 10
<212> TYPE: PRT
<213> ORGANISM: Artificial
```

```
<220> FEATURE:
<223> OTHER INFORMATION: Heavy chain CDR1 of clone 98.

<400> SEQUENCE: 1

Gly Phe Ser Leu Thr Arg Tyr Asn Val His
1               5                   10

<210> SEQ ID NO 2
<211> LENGTH: 9
<212> TYPE: PRT
<213> ORGANISM: Artificial
<220> FEATURE:
<223> OTHER INFORMATION: Heavy chain CDR2 of clone 98.

<400> SEQUENCE: 2

Val Ile Trp Thr Gly Gly Ser Thr Asp
1               5

<210> SEQ ID NO 3
<211> LENGTH: 4
<212> TYPE: PRT
<213> ORGANISM: Artificial
<220> FEATURE:
<223> OTHER INFORMATION: Heavy chain CDR3 of clone 98.

<400> SEQUENCE: 3

Asp Leu Gly Tyr
1

<210> SEQ ID NO 4
<211> LENGTH: 16
<212> TYPE: PRT
<213> ORGANISM: Artificial
<220> FEATURE:
<223> OTHER INFORMATION: Light chain CDR1 of clone 98.

<400> SEQUENCE: 4

Lys Ser Ser Gln Ser Leu Lys Tyr Arg Asp Gly Lys Thr Tyr Leu Asn
1               5                   10                  15

<210> SEQ ID NO 5
<211> LENGTH: 7
<212> TYPE: PRT
<213> ORGANISM: Artificial
<220> FEATURE:
<223> OTHER INFORMATION: Light chain CDR2 of clone 98.

<400> SEQUENCE: 5

Gln Val Ser Lys Leu Asp Ser
1               5

<210> SEQ ID NO 6
<211> LENGTH: 9
<212> TYPE: PRT
<213> ORGANISM: Artificial
<220> FEATURE:
<223> OTHER INFORMATION: Light chain CDR3 of clone 98.

<400> SEQUENCE: 6

Cys Gln Gly Ser Tyr Ser Pro His Thr
1               5

<210> SEQ ID NO 7
<211> LENGTH: 10
<212> TYPE: PRT
<213> ORGANISM: Artificial
<220> FEATURE:
```

```
<223> OTHER INFORMATION: Heavy chain CDR1 of clone 101.

<400> SEQUENCE: 7

Gly Phe Ser Leu Thr Ser Tyr Tyr Met Gln
1               5                   10

<210> SEQ ID NO 8
<211> LENGTH: 9
<212> TYPE: PRT
<213> ORGANISM: Artificial
<220> FEATURE:
<223> OTHER INFORMATION: Heavy chain CDR2 of clone 101.

<400> SEQUENCE: 8

Phe Ile Arg Ser Gly Gly Ser Thr Glu
1               5

<210> SEQ ID NO 9
<211> LENGTH: 10
<212> TYPE: PRT
<213> ORGANISM: Artificial
<220> FEATURE:
<223> OTHER INFORMATION: Heavy chain CDR3 of clone 101.

<400> SEQUENCE: 9

Ala Phe Tyr Gly Gly Tyr Tyr Phe Asp Tyr
1               5                   10

<210> SEQ ID NO 10
<211> LENGTH: 11
<212> TYPE: PRT
<213> ORGANISM: Artificial
<220> FEATURE:
<223> OTHER INFORMATION: Light chain CDR1 of clone 101.

<400> SEQUENCE: 10

Lys Ala Ser Gln Asn Val Gly Ser Asn Val Asp
1               5                   10

<210> SEQ ID NO 11
<211> LENGTH: 7
<212> TYPE: PRT
<213> ORGANISM: Artificial
<220> FEATURE:
<223> OTHER INFORMATION: Light chain CDR2 of clone 101.

<400> SEQUENCE: 11

Lys Ala Ser Asn Arg Tyr Thr
1               5

<210> SEQ ID NO 12
<211> LENGTH: 8
<212> TYPE: PRT
<213> ORGANISM: Artificial
<220> FEATURE:
<223> OTHER INFORMATION: Light chain CDR3 of clone 101.

<400> SEQUENCE: 12

Met Gln Ser Asn Thr Lys Tyr Thr
1               5

<210> SEQ ID NO 13
<211> LENGTH: 131
<212> TYPE: PRT
<213> ORGANISM: Artificial
<220> FEATURE:
<223> OTHER INFORMATION: Heavy chain of clone 98.
```

<400> SEQUENCE: 13

Met Ala Val Leu Val Leu Leu Cys Leu Val Thr Phe Pro Thr Cys
1               5                   10                  15

Val Leu Ser Gln Val Gln Leu Lys Glu Ser Gly Pro Gly Leu Val Gln
            20                  25                  30

Pro Ser Gln Thr Leu Ser Leu Thr Cys Thr Val Ser Gly Phe Ser Leu
            35                  40                  45

Thr Arg Tyr Asn Val His Trp Val Arg Gln Pro Thr Gly Lys Gly Leu
50                  55                  60

Glu Trp Met Gly Val Ile Trp Thr Gly Gly Ser Thr Asp Tyr Asn Ser
65                  70                  75                  80

Ala Leu Lys Ser Arg Leu Ser Ile Ser Arg Asp Thr Ser Lys Ser Gln
                85                  90                  95

Val Phe Leu Lys Met Asn Ser Leu Gln Thr Glu Asp Ile Ala Thr Tyr
            100                 105                 110

Tyr Cys Ala Arg Asp Leu Gly Tyr Trp Gly Gln Gly Val Met Val Thr
            115                 120                 125

Val Ser Ser
    130

<210> SEQ ID NO 14
<211> LENGTH: 132
<212> TYPE: PRT
<213> ORGANISM: Artificial
<220> FEATURE:
<223> OTHER INFORMATION: Light chain of clone 98.

<400> SEQUENCE: 14

Met Met Ser Pro Ala Gln Phe Leu Phe Leu Leu Met Leu Trp Ile Gln
1               5                   10                  15

Glu Thr His Ser Asp Ile Val Met Thr Gln Thr Pro Leu Ser Leu Ser
            20                  25                  30

Val Ala Ile Gly Gln Ser Ala Ser Ile Ser Cys Lys Ser Ser Gln Ser
            35                  40                  45

Leu Lys Tyr Arg Asp Gly Lys Thr Tyr Leu Asn Trp Val Phe Gln Ser
50                  55                  60

Pro Gly Gln Ser Pro Lys Arg Leu Ile Tyr Gln Val Ser Lys Leu Asp
65                  70                  75                  80

Ser Gly Val Pro Asp Arg Phe Ser Gly Thr Gly Ser Glu Thr Asp Phe
                85                  90                  95

Thr Leu Lys Ile Ser Arg Val Glu Ala Glu Asp Leu Gly Val Tyr Tyr
            100                 105                 110

Cys Cys Gln Gly Ser Tyr Ser Pro His Thr Phe Gly Ala Gly Thr Lys
            115                 120                 125

Leu Glu Leu Lys
    130

<210> SEQ ID NO 15
<211> LENGTH: 137
<212> TYPE: PRT
<213> ORGANISM: Artificial
<220> FEATURE:
<223> OTHER INFORMATION: Heavy chain of clone 101.

<400> SEQUENCE: 15

Met Ala Ile Leu Val Leu Leu Cys Leu Val Thr Ile Pro His Ser
1               5                   10                  15

```
Val Leu Ser Gln Val Gln Leu Lys Glu Thr Gly Pro Gly Leu Val Gln
            20                  25                  30

Pro Thr Gln Thr Leu Ser Ile Thr Cys Thr Val Ser Gly Phe Ser Leu
        35                  40                  45

Thr Ser Tyr Tyr Met Gln Trp Val Arg Gln Pro Gly Lys Gly Leu
    50                  55                  60

Glu Trp Met Gly Phe Ile Arg Ser Gly Gly Ser Thr Glu Tyr Asn Ser
65                  70                  75                  80

Glu Phe Lys Ser Arg Leu Ser Ile Ser Arg Asp Thr Ser Lys Asn Gln
                85                  90                  95

Val Phe Leu Lys Met Asn Ser Leu Lys Thr Glu Asp Thr Gly Val Tyr
            100                 105                 110

Tyr Cys Ala Arg Ala Phe Tyr Gly Gly Tyr Tyr Phe Asp Tyr Trp Gly
        115                 120                 125

Gln Gly Val Met Val Thr Val Ser Ser
        130                 135
```

<210> SEQ ID NO 16
<211> LENGTH: 130
<212> TYPE: PRT
<213> ORGANISM: Artificial
<220> FEATURE:
<223> OTHER INFORMATION: Light chain of clone 101.

<400> SEQUENCE: 16

```
Met Gly Ile Arg Met Glu Ser His Thr Arg Val Phe Ile Phe Leu Leu
1               5                   10                  15

Leu Trp Leu Ser Gly Ala Asp Gly Asp Ile Val Met Thr Gln Ser Pro
            20                  25                  30

Thr Ser Ile Ser Ile Ser Val Gly Glu Arg Val Thr Met Asn Cys Lys
        35                  40                  45

Ala Ser Gln Asn Val Gly Ser Asn Val Asp Trp Tyr Gln Gln Lys Thr
    50                  55                  60

Gly Gln Ser Pro Lys Leu Leu Ile Tyr Lys Ala Ser Asn Arg Tyr Thr
65                  70                  75                  80

Gly Val Pro Asp Arg Phe Thr Gly Ser Gly Ser Gly Thr Asp Phe Thr
                85                  90                  95

Phe Thr Ile Ser Asn Met Gln Ala Glu Asp Leu Ala Val Tyr Tyr Cys
            100                 105                 110

Met Gln Ser Asn Thr Lys Tyr Thr Phe Gly Ala Gly Thr Lys Leu Glu
        115                 120                 125

Leu Lys
    130
```

<210> SEQ ID NO 17
<211> LENGTH: 517
<212> TYPE: PRT
<213> ORGANISM: Homo sapiens
<220> FEATURE:
<221> NAME/KEY: MISC_FEATURE
<223> OTHER INFORMATION: TMEM-180 protein.

<400> SEQUENCE: 17

```
Met Gly Leu Gly Gln Pro Gln Ala Trp Leu Leu Gly Leu Pro Thr Ala
1               5                   10                  15

Val Val Tyr Gly Ser Leu Ala Leu Phe Thr Thr Ile Leu His Asn Val
            20                  25                  30
```

```
Phe Leu Leu Tyr Tyr Val Asp Thr Phe Val Ser Val Tyr Lys Ile Asn
             35                  40                  45

Lys Met Ala Phe Trp Val Gly Glu Thr Val Phe Leu Leu Trp Asn Ser
 50                  55                  60

Leu Asn Asp Pro Leu Phe Gly Trp Leu Ser Asp Arg Gln Phe Leu Ser
 65                  70                  75                  80

Ser Gln Pro Arg Ser Gly Ala Gly Leu Ser Ser Arg Ala Val Val Leu
                 85                  90                  95

Ala Arg Val Gln Ala Leu Gly Trp His Gly Pro Leu Leu Ala Leu Ser
            100                 105                 110

Phe Leu Ala Phe Trp Val Pro Trp Ala Pro Ala Gly Leu Gln Phe Leu
            115                 120                 125

Leu Cys Leu Cys Leu Tyr Asp Gly Phe Leu Thr Leu Val Asp Leu His
        130                 135                 140

His His Ala Leu Leu Ala Asp Leu Ala Leu Ser Ala His Asp Arg Thr
145                 150                 155                 160

His Leu Asn Phe Tyr Cys Ser Leu Phe Ser Ala Ala Gly Ser Leu Ser
                165                 170                 175

Val Phe Ala Ser Tyr Ala Phe Trp Asn Lys Glu Asp Phe Ser Ser Phe
            180                 185                 190

Arg Ala Phe Cys Val Thr Leu Ala Val Ser Ser Gly Leu Gly Phe Leu
        195                 200                 205

Gly Ala Thr Gln Leu Leu Arg Arg Val Glu Ala Ala Arg Lys Asp
            210                 215                 220

Pro Gly Cys Ser Gly Leu Val Val Asp Ser Gly Leu Cys Gly Glu Glu
225                 230                 235                 240

Leu Leu Val Gly Ser Glu Glu Ala Asp Ser Ile Thr Leu Gly Arg Tyr
                245                 250                 255

Leu Arg Gln Leu Ala Arg His Arg Asn Phe Leu Trp Phe Val Ser Met
            260                 265                 270

Asp Leu Val Gln Val Phe His Cys His Phe Asn Ser Asn Phe Phe Pro
        275                 280                 285

Leu Phe Leu Glu His Leu Leu Ser Asp His Ile Ser Leu Ser Thr Gly
        290                 295                 300

Ser Ile Leu Leu Gly Leu Ser Tyr Val Ala Pro His Leu Asn Asn Leu
305                 310                 315                 320

Tyr Phe Leu Ser Leu Cys Arg Arg Trp Gly Val Tyr Ala Val Val Arg
                325                 330                 335

Gly Leu Phe Leu Leu Lys Leu Gly Leu Ser Leu Leu Met Leu Leu Ala
            340                 345                 350

Gly Pro Asp His Leu Ser Leu Leu Cys Leu Phe Ile Ala Ser Asn Arg
            355                 360                 365

Val Phe Thr Glu Gly Thr Cys Lys Leu Leu Thr Leu Val Thr Asp
        370                 375                 380

Leu Val Asp Glu Asp Leu Val Leu Asn His Arg Lys Gln Ala Ala Ser
385                 390                 395                 400

Ala Leu Leu Phe Gly Met Val Ala Leu Val Thr Lys Pro Gly Gln Thr
                405                 410                 415

Phe Ala Pro Leu Leu Gly Thr Trp Leu Leu Cys Phe Tyr Thr Gly His
            420                 425                 430

Asp Leu Phe Gln Gln Ser Leu Ile Thr Pro Val Gly Ser Ala His Pro
        435                 440                 445

Trp Pro Glu Pro Pro Ala Pro Ala Pro Ala Gln Ala Pro Thr Leu Arg
```

```
            450               455               460
Gln Gly Cys Phe Tyr Leu Leu Val Leu Val Pro Ile Thr Cys Ala Leu
465                 470                 475                 480

Leu Gln Leu Phe Thr Trp Ser Gln Phe Thr Leu His Gly Arg Leu
                485                 490                 495

His Met Val Lys Ala Gln Arg Gln Asn Leu Ser Gln Ala Gln Thr Leu
                500                 505                 510

Asp Val Lys Met Val
        515

<210> SEQ ID NO 18
<211> LENGTH: 73
<212> TYPE: DNA
<213> ORGANISM: Artificial
<220> FEATURE:
<223> OTHER INFORMATION: Synthesized primer.

<400> SEQUENCE: 18
cagacctgca cctgaacgtg gttgagagct gaggaattga cggtcactga gggactgtaa      60
tgctgcactt cgc                                                        73

<210> SEQ ID NO 19
<211> LENGTH: 78
<212> TYPE: DNA
<213> ORGANISM: Artificial
<220> FEATURE:
<223> OTHER INFORMATION: Synthesized primer.

<400> SEQUENCE: 19
caaccacgtt caggtgcagg tctgtcttca cgtgctgttg tactggctcg tgttcaagag      60
ttcaaactgg aggacctg                                                   78

<210> SEQ ID NO 20
<211> LENGTH: 33
<212> TYPE: DNA
<213> ORGANISM: Artificial
<220> FEATURE:
<223> OTHER INFORMATION: Synthesized primer.

<400> SEQUENCE: 20
gagatataca tatgtcggag gtgactcgta gtc                                  33

<210> SEQ ID NO 21
<211> LENGTH: 31
<212> TYPE: DNA
<213> ORGANISM: Artificial
<220> FEATURE:
<223> OTHER INFORMATION: Synthesized primer.

<400> SEQUENCE: 21
tggtgctcga aataggctg aacatcaaat g                                     31

<210> SEQ ID NO 22
<211> LENGTH: 54
<212> TYPE: DNA
<213> ORGANISM: Artificial
<220> FEATURE:
<223> OTHER INFORMATION: Synthesized primer.

<400> SEQUENCE: 22
gcgaagtgca gcattacagt ccgatcatct gagtctgctg tgcctcttca ttgc           54
```

<210> SEQ ID NO 23
<211> LENGTH: 66
<212> TYPE: DNA
<213> ORGANISM: Artificial
<220> FEATURE:
<223> OTHER INFORMATION: Synthesized primer.

<400> SEQUENCE: 23
caggtcctcc agtttgaact cagaagctgc ttgcttacga tgattcagca ccaggtcctc    60
gtctac    66

<210> SEQ ID NO 24
<211> LENGTH: 33
<212> TYPE: DNA
<213> ORGANISM: Artificial
<220> FEATURE:
<223> OTHER INFORMATION: Synthesized primer.

<400> SEQUENCE: 24
gagatataca tatgtcggag gtgactcgta gtc    33

<210> SEQ ID NO 25
<211> LENGTH: 31
<212> TYPE: DNA
<213> ORGANISM: Artificial
<220> FEATURE:
<223> OTHER INFORMATION: Synthesized primer.

<400> SEQUENCE: 25
tggtgctcga aataggctg aacatcaaat g    31

<210> SEQ ID NO 26
<211> LENGTH: 45
<212> TYPE: DNA
<213> ORGANISM: Artificial
<220> FEATURE:
<223> OTHER INFORMATION: Synthesized primer.

<400> SEQUENCE: 26
ctaatacgac tcactatagg gcaagcagtg gtatcaacgc agagt    45

<210> SEQ ID NO 27
<211> LENGTH: 22
<212> TYPE: DNA
<213> ORGANISM: Artificial
<220> FEATURE:
<223> OTHER INFORMATION: Synthesized primer.

<400> SEQUENCE: 27
ctaatacgac tcactatagg gc    22

<210> SEQ ID NO 28
<211> LENGTH: 29
<212> TYPE: DNA
<213> ORGANISM: Artificial
<220> FEATURE:
<223> OTHER INFORMATION: Synthesized primer.

<400> SEQUENCE: 28
cccatggcca ccarattcty atcagacag    29

<210> SEQ ID NO 29
<211> LENGTH: 45
<212> TYPE: DNA
<213> ORGANISM: Artificial
<220> FEATURE:

```
<223> OTHER INFORMATION: Synthesized primer.

<400> SEQUENCE: 29
ctaatacgac tcactatagg gcaagcagtg gtatcaacgc agagt          45

<210> SEQ ID NO 30
<211> LENGTH: 22
<212> TYPE: DNA
<213> ORGANISM: Artificial
<220> FEATURE:
<223> OTHER INFORMATION: Synthesized primer.

<400> SEQUENCE: 30
ctaatacgac tcactatagg gc                                   22

<210> SEQ ID NO 31
<211> LENGTH: 28
<212> TYPE: DNA
<213> ORGANISM: Artificial
<220> FEATURE:
<223> OTHER INFORMATION: Synthesized primer.

<400> SEQUENCE: 31
gttgttcawg argcacacga ctgaggca                             28

<210> SEQ ID NO 32
<211> LENGTH: 10
<212> TYPE: PRT
<213> ORGANISM: Artificial
<220> FEATURE:
<223> OTHER INFORMATION: Heavy chain CDR1 of clone 212.

<400> SEQUENCE: 32

Gly Phe Thr Phe Ser Asp Tyr Ala Met Ala
1               5                   10

<210> SEQ ID NO 33
<211> LENGTH: 9
<212> TYPE: PRT
<213> ORGANISM: Artificial
<220> FEATURE:
<223> OTHER INFORMATION: Heavy chain CDR2 of clone 212.

<400> SEQUENCE: 33

Thr Ile Ile Tyr Asp Gly Ser Ser Thr
1               5

<210> SEQ ID NO 34
<211> LENGTH: 8
<212> TYPE: PRT
<213> ORGANISM: Artificial
<220> FEATURE:
<223> OTHER INFORMATION: Heavy chain CDR3 of clone 212.

<400> SEQUENCE: 34

His Trp Tyr Trp Tyr Phe Asp Phe
1               5

<210> SEQ ID NO 35
<211> LENGTH: 11
<212> TYPE: PRT
<213> ORGANISM: Artificial
<220> FEATURE:
<223> OTHER INFORMATION: Light chain CDR1 of clone 212.

<400> SEQUENCE: 35
```

```
Leu Ala Ser Glu Gly Ile Ser Asn Asp Leu Ala
1               5                   10
```

<210> SEQ ID NO 36
<211> LENGTH: 7
<212> TYPE: PRT
<213> ORGANISM: Artificial
<220> FEATURE:
<223> OTHER INFORMATION: Light chain CDR2 of clone 212.

<400> SEQUENCE: 36

```
Ala Ala Ser Arg Leu Gln Asp
1               5
```

<210> SEQ ID NO 37
<211> LENGTH: 9
<212> TYPE: PRT
<213> ORGANISM: Artificial
<220> FEATURE:
<223> OTHER INFORMATION: Light chain CDR3 of clone 212.

<400> SEQUENCE: 37

```
Gln Gln Ser Tyr Lys Tyr Pro Leu Thr
1               5
```

<210> SEQ ID NO 38
<211> LENGTH: 136
<212> TYPE: PRT
<213> ORGANISM: Artificial
<220> FEATURE:
<223> OTHER INFORMATION: Heavy chain of clone 212.

<400> SEQUENCE: 38

```
Met Asp Ile Arg Leu Ser Leu Ala Phe Leu Val Leu Phe Ile Lys Gly
1               5                   10                  15

Val Gln Cys Glu Val Gln Leu Val Glu Ser Gly Gly Gly Leu Val Gln
            20                  25                  30

Pro Gly Asn Ser Leu Lys Leu Ser Cys Ala Ala Ser Gly Phe Thr Phe
        35                  40                  45

Ser Asp Tyr Ala Met Ala Trp Val Arg Gln Ser Pro Lys Lys Gly Leu
    50                  55                  60

Glu Trp Val Ala Thr Ile Ile Tyr Asp Gly Ser Ser Thr Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asp Ser Leu Arg Ser Glu Asp Thr Ala Thr
            100                 105                 110

Tyr Tyr Cys Ala Thr His Trp Tyr Trp Tyr Phe Asp Phe Trp Gly Pro
        115                 120                 125

Gly Thr Met Val Thr Val Ser Ser
    130                 135
```

<210> SEQ ID NO 39
<211> LENGTH: 127
<212> TYPE: PRT
<213> ORGANISM: Artificial
<220> FEATURE:
<223> OTHER INFORMATION: Light chain of clone 212.

<400> SEQUENCE: 39

```
Met Gly Val Pro Thr Gln Leu Leu Gly Leu Leu Leu Leu Trp Ile Thr
1               5                   10                  15
```

-continued

Asp Ala Ile Cys Asp Ile Gln Met Thr Gln Ser Pro Ala Ser Leu Ser
            20                  25                  30

Ala Ser Leu Gly Glu Thr Val Ser Ile Glu Cys Leu Ala Ser Glu Gly
        35                  40                  45

Ile Ser Asn Asp Leu Ala Trp Tyr Gln Gln Lys Ser Gly Lys Ser Pro
    50                  55                  60

Gln Leu Leu Ile Tyr Ala Ala Ser Arg Leu Gln Asp Gly Val Pro Ser
65                  70                  75                  80

Arg Phe Ser Gly Ser Gly Ser Gly Thr Arg Tyr Ser Leu Lys Ile Ser
                85                  90                  95

Gly Met Gln Pro Glu Asp Glu Ala Asp Tyr Phe Cys Gln Gln Ser Tyr
            100                 105                 110

Lys Tyr Pro Leu Thr Phe Gly Ser Gly Thr Lys Leu Glu Ile Lys
        115                 120                 125

<210> SEQ ID NO 40
<211> LENGTH: 10
<212> TYPE: PRT
<213> ORGANISM: Artificial
<220> FEATURE:
<223> OTHER INFORMATION: Heavy chain CDR1 of clone 212.

<400> SEQUENCE: 40

Gly Phe Thr Phe Ser Asp Tyr Ala Met Ala
1               5                   10

<210> SEQ ID NO 41
<211> LENGTH: 9
<212> TYPE: PRT
<213> ORGANISM: Artificial
<220> FEATURE:
<223> OTHER INFORMATION: Heavy chain CDR2 of clone 212.

<400> SEQUENCE: 41

Thr Ile Ile Tyr Asp Gly Ser Ser Thr
1               5

<210> SEQ ID NO 42
<211> LENGTH: 8
<212> TYPE: PRT
<213> ORGANISM: Artificial
<220> FEATURE:
<223> OTHER INFORMATION: Heavy chain CDR3 of clone 212.

<400> SEQUENCE: 42

His Trp Tyr Trp Tyr Phe Asp Phe
1               5

<210> SEQ ID NO 43
<211> LENGTH: 11
<212> TYPE: PRT
<213> ORGANISM: Artificial
<220> FEATURE:
<223> OTHER INFORMATION: Light chain CDR1 of clone 212.

<400> SEQUENCE: 43

Leu Ala Ser Glu Gly Ile Ser Asn Asp Leu Ala
1               5                   10

<210> SEQ ID NO 44
<211> LENGTH: 7
<212> TYPE: PRT
<213> ORGANISM: Artificial
<220> FEATURE:

-continued

<223> OTHER INFORMATION: Light chain CDR2 of clone 212.

<400> SEQUENCE: 44

Ala Ala Ser Arg Leu Gln Asp
1               5

<210> SEQ ID NO 45
<211> LENGTH: 9
<212> TYPE: PRT
<213> ORGANISM: Artificial
<220> FEATURE:
<223> OTHER INFORMATION: Light chain CDR3 of clone 212.

<400> SEQUENCE: 45

Gln Gln Ser Tyr Lys Tyr Pro Leu Thr
1               5

<210> SEQ ID NO 46
<211> LENGTH: 136
<212> TYPE: PRT
<213> ORGANISM: Artificial
<220> FEATURE:
<223> OTHER INFORMATION: Heavy chain variable region of clone 212.

<400> SEQUENCE: 46

Met Asp Ile Arg Leu Ser Leu Ala Phe Leu Val Leu Phe Ile Lys Gly
1               5                   10                  15

Val Gln Cys Glu Val Gln Leu Val Glu Ser Gly Gly Gly Leu Val Gln
            20                  25                  30

Pro Gly Asn Ser Leu Lys Leu Ser Cys Ala Ala Ser Gly Phe Thr Phe
        35                  40                  45

Ser Asp Tyr Ala Met Ala Trp Val Arg Gln Ser Pro Lys Lys Gly Leu
    50                  55                  60

Glu Trp Val Ala Thr Ile Ile Tyr Asp Gly Ser Ser Thr Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asp Ser Leu Arg Ser Glu Asp Thr Ala Thr
            100                 105                 110

Tyr Tyr Cys Ala Thr His Trp Tyr Trp Tyr Phe Asp Phe Trp Gly Pro
        115                 120                 125

Gly Thr Met Val Thr Val Ser Ser
        130                 135

<210> SEQ ID NO 47
<211> LENGTH: 127
<212> TYPE: PRT
<213> ORGANISM: Artificial
<220> FEATURE:
<223> OTHER INFORMATION: Light chain variable region of clone 212.

<400> SEQUENCE: 47

Met Gly Val Pro Thr Gln Leu Leu Gly Leu Leu Leu Leu Trp Ile Thr
1               5                   10                  15

Asp Ala Ile Cys Asp Ile Gln Met Thr Gln Ser Pro Ala Ser Leu Ser
            20                  25                  30

Ala Ser Leu Gly Glu Thr Val Ser Ile Glu Cys Leu Ala Ser Glu Gly
        35                  40                  45

Ile Ser Asn Asp Leu Ala Trp Tyr Gln Gln Lys Ser Gly Lys Ser Pro
    50                  55                  60

Gln Leu Leu Ile Tyr Ala Ala Ser Arg Leu Gln Asp Gly Val Pro Ser
65                  70                  75                  80

Arg Phe Ser Gly Ser Gly Ser Gly Thr Arg Tyr Ser Leu Lys Ile Ser
                85                  90                  95

Gly Met Gln Pro Glu Asp Glu Ala Asp Tyr Phe Cys Gln Gln Ser Tyr
            100                 105                 110

Lys Tyr Pro Leu Thr Phe Gly Ser Gly Thr Lys Leu Glu Ile Lys
        115                 120                 125

<210> SEQ ID NO 48
<211> LENGTH: 5
<212> TYPE: PRT
<213> ORGANISM: Artificial
<220> FEATURE:
<223> OTHER INFORMATION: Heavy chain CDR1 of clone 129.

<400> SEQUENCE: 48

Asp Cys Ala Leu Asn
1               5

<210> SEQ ID NO 49
<211> LENGTH: 15
<212> TYPE: PRT
<213> ORGANISM: Artificial
<220> FEATURE:
<223> OTHER INFORMATION: Heavy chain CDR2 of clone 129.

<400> SEQUENCE: 49

Trp Ile Asn Thr Gln Thr Gly Lys Pro Thr Tyr Ala Asp Asp Phe
1               5                   10                  15

<210> SEQ ID NO 50
<211> LENGTH: 8
<212> TYPE: PRT
<213> ORGANISM: Artificial
<220> FEATURE:
<223> OTHER INFORMATION: Heavy chain CDR3 of clone 129.

<400> SEQUENCE: 50

Glu Asp Tyr Gly Tyr Phe Asp Tyr
1               5

<210> SEQ ID NO 51
<211> LENGTH: 11
<212> TYPE: PRT
<213> ORGANISM: Artificial
<220> FEATURE:
<223> OTHER INFORMATION: Light chain CDR1 of clone 129.

<400> SEQUENCE: 51

Gln Ala Ser Gln Asn Ile Asn Lys Phe Ile Ala
1               5                   10

<210> SEQ ID NO 52
<211> LENGTH: 7
<212> TYPE: PRT
<213> ORGANISM: Artificial
<220> FEATURE:
<223> OTHER INFORMATION: Light chain CDR2 of clone 129.

<400> SEQUENCE: 52

Tyr Thr Ser Thr Leu Val Ser
1               5

<210> SEQ ID NO 53

```
<211> LENGTH: 7
<212> TYPE: PRT
<213> ORGANISM: Artificial
<220> FEATURE:
<223> OTHER INFORMATION: Light chain CDR3 of clone 129.

<400> SEQUENCE: 53

Leu Gln Tyr Asp Asn Leu Arg
1               5

<210> SEQ ID NO 54
<211> LENGTH: 136
<212> TYPE: PRT
<213> ORGANISM: Artificial
<220> FEATURE:
<223> OTHER INFORMATION: Heavy chain variable region of clone 129.

<400> SEQUENCE: 54

Met Asp Trp Leu Trp Asn Leu Leu Phe Leu Met Val Val Ala Gln Ser
1               5                   10                  15

Ala Gln Ala Gln Ile Gln Leu Val Gln Ser Gly Pro Glu Leu Lys Lys
            20                  25                  30

Pro Gly Glu Ser Val Lys Ile Ser Cys Lys Ala Ser Gly Tyr Thr Phe
        35                  40                  45

Thr Asp Cys Ala Leu Asn Trp Val Lys Gln Ala Pro Gly Asn Gly Leu
    50                  55                  60

Lys Trp Met Gly Trp Ile Asn Thr Gln Thr Gly Lys Pro Thr Tyr Ala
65                  70                  75                  80

Asp Asp Phe Lys Gln Arg Phe Val Phe Ser Leu Glu Thr Ser Ala Ser
                85                  90                  95

Thr Ala Tyr Leu Gln Ile Asn Asn Leu Asn Ile Glu Asp Thr Ala Thr
            100                 105                 110

Tyr Phe Cys Thr Arg Glu Asp Tyr Gly Tyr Phe Asp Tyr Trp Gly Gln
        115                 120                 125

Gly Val Met Val Thr Val Ser Ser
        130                 135

<210> SEQ ID NO 55
<211> LENGTH: 126
<212> TYPE: PRT
<213> ORGANISM: Artificial
<220> FEATURE:
<223> OTHER INFORMATION: Light chain variable region of clone 129.

<400> SEQUENCE: 55

Met Arg Thr Ser Ile Gln Leu Leu Gly Leu Leu Leu Trp Leu His
1               5                   10                  15

Asp Ala Gln Cys Asp Ile Gln Met Thr Gln Ser Pro Pro Ser Leu Ser
            20                  25                  30

Ala Ser Leu Gly Asp Lys Val Thr Ile Thr Cys Gln Ala Ser Gln Asn
        35                  40                  45

Ile Asn Lys Phe Ile Ala Trp Tyr Gln Gln Lys Pro Gly Lys Ala Pro
    50                  55                  60

Arg His Leu Val His Tyr Thr Ser Thr Leu Val Ser Gly Thr Pro Ser
65                  70                  75                  80

Arg Phe Ser Gly Ser Gly Ser Gly Arg Asp Tyr Ser Phe Ser Ile Ser
                85                  90                  95

Asn Val Glu Ser Glu Asp Ile Ala Ser Tyr Tyr Cys Leu Gln Tyr Asp
            100                 105                 110
```

Asn Leu Arg Thr Phe Gly Gly Thr Lys Leu Glu Leu Lys
        115                 120                 125

<210> SEQ ID NO 56
<211> LENGTH: 5
<212> TYPE: PRT
<213> ORGANISM: Artificial
<220> FEATURE:
<223> OTHER INFORMATION: Heavy chain CDR1 of clone 382.

<400> SEQUENCE: 56

Asn Tyr Gly Met His
1               5

<210> SEQ ID NO 57
<211> LENGTH: 15
<212> TYPE: PRT
<213> ORGANISM: Artificial
<220> FEATURE:
<223> OTHER INFORMATION: Heavy chain CDR2 of clone 382.

<400> SEQUENCE: 57

Ser Ile Ser Pro Ser Gly Gly Ser Thr Tyr Tyr Arg Asp Ser Val
1               5                   10                  15

<210> SEQ ID NO 58
<211> LENGTH: 13
<212> TYPE: PRT
<213> ORGANISM: Artificial
<220> FEATURE:
<223> OTHER INFORMATION: Heavy chain CDR3 of clone 382.

<400> SEQUENCE: 58

Ser Ala Ser Ile Thr Ala Tyr Tyr Tyr Val Met Asp Ala
1               5                   10

<210> SEQ ID NO 59
<211> LENGTH: 11
<212> TYPE: PRT
<213> ORGANISM: Artificial
<220> FEATURE:
<223> OTHER INFORMATION: Light chain CDR1 of clone 382.

<400> SEQUENCE: 59

Lys Ala Ser Gln Asn Val Gly Ser Asn Val Asp
1               5                   10

<210> SEQ ID NO 60
<211> LENGTH: 7
<212> TYPE: PRT
<213> ORGANISM: Artificial
<220> FEATURE:
<223> OTHER INFORMATION: Light chain CDR2 of clone 382.

<400> SEQUENCE: 60

Lys Ala Ser Asn Arg Tyr Thr
1               5

<210> SEQ ID NO 61
<211> LENGTH: 9
<212> TYPE: PRT
<213> ORGANISM: Artificial
<220> FEATURE:
<223> OTHER INFORMATION: Light chain CDR3 of clone 382.

<400> SEQUENCE: 61

Met Gln Ser Asn Ser Tyr Pro Pro Thr

-continued

<210> SEQ ID NO 62
<211> LENGTH: 141
<212> TYPE: PRT
<213> ORGANISM: Artificial
<220> FEATURE:
<223> OTHER INFORMATION: Heavy chain variable region of clone 382.

<400> SEQUENCE: 62

Met Asp Ile Arg Leu Ser Leu Gly Phe Leu Val Leu Phe Ile Lys Gly
1               5                   10                  15

Val Gln Cys Glu Val Gln Leu Val Glu Ser Gly Gly Gly Leu Val Gln
            20                  25                  30

Pro Gly Arg Ser Leu Lys Leu Ser Cys Ala Ala Ser Gly Phe Thr Phe
        35                  40                  45

Ser Asn Tyr Gly Met His Trp Ile Arg Gln Ala Pro Thr Lys Gly Leu
    50                  55                  60

Glu Trp Val Ala Ser Ile Ser Pro Ser Gly Gly Ser Thr Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asp Ser Leu Arg Ser Glu Asp Thr Ala Thr
            100                 105                 110

Tyr Tyr Cys Ala Thr Ser Ala Ser Ile Thr Ala Tyr Tyr Tyr Val Met
        115                 120                 125

Asp Ala Trp Gly Gln Gly Ala Ser Val Thr Val Ser Ser
    130                 135                 140

<210> SEQ ID NO 63
<211> LENGTH: 127
<212> TYPE: PRT
<213> ORGANISM: Artificial
<220> FEATURE:
<223> OTHER INFORMATION: Light chain variable region of clone 382.

<400> SEQUENCE: 63

Met Glu Ser His Thr Arg Val Phe Ile Phe Leu Leu Leu Trp Leu Ser
1               5                   10                  15

Gly Ala Asp Gly Asp Ile Val Met Thr Gln Ser Pro Thr Ser Met Ser
            20                  25                  30

Ile Ser Val Gly Asp Arg Val Thr Met Asn Cys Lys Ala Ser Gln Asn
        35                  40                  45

Val Gly Ser Asn Val Asp Trp Tyr Gln Gln Lys Thr Gly Gln Ser Pro
    50                  55                  60

Lys Leu Leu Ile Tyr Lys Ala Ser Asn Arg Tyr Thr Gly Val Pro Asp
65                  70                  75                  80

Arg Phe Thr Gly Ser Gly Ser Gly Thr Asp Phe Thr Phe Thr Ile Ser
                85                  90                  95

Asn Met Gln Ala Glu Asp Leu Ala Val Tyr Tyr Cys Met Gln Ser Asn
            100                 105                 110

Ser Tyr Pro Pro Thr Phe Gly Gly Gly Thr Lys Leu Glu Leu Arg
        115                 120                 125

<210> SEQ ID NO 64
<211> LENGTH: 5
<212> TYPE: PRT
<213> ORGANISM: Artificial
<220> FEATURE:

```
<223> OTHER INFORMATION: Heavy chain CDR1 of clone 1361.

<400> SEQUENCE: 64

Asn Tyr Trp Met Thr
1               5

<210> SEQ ID NO 65
<211> LENGTH: 15
<212> TYPE: PRT
<213> ORGANISM: Artificial
<220> FEATURE:
<223> OTHER INFORMATION: Heavy chain CDR2 of clone 1361.

<400> SEQUENCE: 65

Ser Ile Thr Asn Thr Gly Gly Ser Thr Tyr Tyr Pro Asp Ser Val
1               5                   10                  15

<210> SEQ ID NO 66
<211> LENGTH: 12
<212> TYPE: PRT
<213> ORGANISM: Artificial
<220> FEATURE:
<223> OTHER INFORMATION: Heavy chain CDR3 of clone 1361.

<400> SEQUENCE: 66

Ala Gly Tyr Ser Ser Tyr Pro Asp Tyr Phe Asp Tyr
1               5                   10

<210> SEQ ID NO 67
<211> LENGTH: 11
<212> TYPE: PRT
<213> ORGANISM: Artificial
<220> FEATURE:
<223> OTHER INFORMATION: Light chain CDR1 of clone 1361.

<400> SEQUENCE: 67

Lys Ala Gly Gln Asn Ile Tyr Asn Tyr Leu Ala
1               5                   10

<210> SEQ ID NO 68
<211> LENGTH: 7
<212> TYPE: PRT
<213> ORGANISM: Artificial
<220> FEATURE:
<223> OTHER INFORMATION: Light chain CDR2 of clone 1361.

<400> SEQUENCE: 68

Asn Ala Asn Ser Leu Gln Thr
1               5

<210> SEQ ID NO 69
<211> LENGTH: 7
<212> TYPE: PRT
<213> ORGANISM: Artificial
<220> FEATURE:
<223> OTHER INFORMATION: Light chain CDR3 of clone 1361.

<400> SEQUENCE: 69

Gln Gln Tyr Ser Ser Gly Trp
1               5

<210> SEQ ID NO 70
<211> LENGTH: 140
<212> TYPE: PRT
<213> ORGANISM: Artificial
<220> FEATURE:
<223> OTHER INFORMATION: Heavy chain variable region of clone 1361.
```

<400> SEQUENCE: 70

Met Asp Ile Arg Leu Ser Leu Val Phe Leu Val Leu Phe Ile Lys Gly
1               5                   10                  15

Val Gln Cys Glu Val Gln Leu Val Glu Ser Gly Gly Gly Leu Val Gln
            20                  25                  30

Pro Gly Arg Ser Leu Lys Leu Ser Cys Val Ala Ser Gly Phe Thr Phe
        35                  40                  45

Asn Asn Tyr Trp Met Thr Trp Ile Arg Gln Ala Pro Gly Lys Gly Leu
    50                  55                  60

Glu Trp Val Ala Ser Ile Thr Asn Thr Gly Gly Ser Thr Tyr Tyr Pro
65                  70                  75                  80

Asp Ser Val Lys Gly Arg Phe Thr Ile Ser Arg Asp Tyr Ala Lys Ser
                85                  90                  95

Thr Leu Tyr Leu Gln Met Asn Ser Leu Arg Ser Glu Asp Thr Ala Thr
            100                 105                 110

Tyr Tyr Cys Thr Arg Ala Gly Tyr Ser Ser Tyr Pro Tyr Phe Asp
        115                 120                 125

Tyr Trp Gly Gln Gly Val Met Leu Thr Val Ser Ser
    130                 135                 140

<210> SEQ ID NO 71
<211> LENGTH: 126
<212> TYPE: PRT
<213> ORGANISM: Artificial
<220> FEATURE:
<223> OTHER INFORMATION: Light chain variable region of clone 1361.

<400> SEQUENCE: 71

Met Met Ala Pro Val Gln Leu Leu Gly Leu Leu Leu Trp Leu Pro
1               5                   10                  15

Ala Met Arg Cys Asn Ile Gln Met Thr Gln Ser Pro Ser Leu Leu Ser
            20                  25                  30

Ala Ser Val Gly Asp Arg Val Thr Leu Ser Cys Lys Ala Gly Gln Asn
        35                  40                  45

Ile Tyr Asn Tyr Leu Ala Trp Tyr Gln Gln Lys Leu Gly Glu Ala Pro
    50                  55                  60

Lys Leu Leu Ile Tyr Asn Ala Asn Ser Leu Gln Thr Gly Ile Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Val Ala Thr Tyr Phe Cys Gln Gln Tyr Ser
            100                 105                 110

Ser Gly Trp Thr Phe Gly Gly Gly Thr Lys Leu Glu Leu Lys
        115                 120                 125

<210> SEQ ID NO 72
<211> LENGTH: 5
<212> TYPE: PRT
<213> ORGANISM: Artificial
<220> FEATURE:
<223> OTHER INFORMATION: Heavy chain CDR1 of clone 669.

<400> SEQUENCE: 72

Asp Tyr Trp Val Ser
1               5

<210> SEQ ID NO 73

```
<211> LENGTH: 16
<212> TYPE: PRT
<213> ORGANISM: Artificial
<220> FEATURE:
<223> OTHER INFORMATION: Heavy chain CDR2 of clone 669.

<400> SEQUENCE: 73

Glu Ile Tyr Pro Asn Ser Gly Ala Thr Asn Phe Asn Glu Asn Phe Lys
1               5                   10                  15

<210> SEQ ID NO 74
<211> LENGTH: 12
<212> TYPE: PRT
<213> ORGANISM: Artificial
<220> FEATURE:
<223> OTHER INFORMATION: Heavy chain CDR3 of clone 669.

<400> SEQUENCE: 74

Asp Gly Thr Met Gly Ile Ala Tyr Tyr Phe Asp Tyr
1               5                   10

<210> SEQ ID NO 75
<211> LENGTH: 11
<212> TYPE: PRT
<213> ORGANISM: Artificial
<220> FEATURE:
<223> OTHER INFORMATION: Light chain CDR1 of clone 669.

<400> SEQUENCE: 75

Lys Ala Ser Gln Asn Ile Asn Arg Tyr Leu Asn
1               5                   10

<210> SEQ ID NO 76
<211> LENGTH: 7
<212> TYPE: PRT
<213> ORGANISM: Artificial
<220> FEATURE:
<223> OTHER INFORMATION: Light chain CDR2 of clone 669.

<400> SEQUENCE: 76

Asn Ala Asn Ser Leu Gln Thr
1               5

<210> SEQ ID NO 77
<211> LENGTH: 9
<212> TYPE: PRT
<213> ORGANISM: Artificial
<220> FEATURE:
<223> OTHER INFORMATION: Light chain CDR3 of clone 669.

<400> SEQUENCE: 77

Leu Gln His Asn Ser Trp Pro Tyr Thr
1               5

<210> SEQ ID NO 78
<211> LENGTH: 139
<212> TYPE: PRT
<213> ORGANISM: Artificial
<220> FEATURE:
<223> OTHER INFORMATION: Heavy chain variable region of clone 669.

<400> SEQUENCE: 78

Met Gly Trp Ile Cys Ile Ile Phe Leu Val Ala Thr Ala Thr Gly Val
1               5                   10                  15

His Ser Gln Val Lys Leu Leu Gln Ser Gly Ala Ala Leu Val Lys Pro
                20                  25                  30
```

```
Gly Ala Ser Val Lys Met Ser Cys Lys Ala Ser Gly Tyr Thr Phe Thr
            35                  40                  45

Asp Tyr Trp Val Ser Trp Val Lys Gln Ser His Gly Lys Ser Leu Glu
 50                  55                  60

Trp Ile Gly Glu Ile Tyr Pro Asn Ser Gly Ala Thr Asn Phe Asn Glu
 65                  70                  75                  80

Asn Phe Lys Gly Lys Ala Thr Leu Thr Val Asp Lys Ser Thr Ser Thr
                 85                  90                  95

Ala Tyr Met Glu Leu Ser Arg Leu Thr Ser Glu Asp Ser Ala Ile Tyr
                100                 105                 110

Tyr Cys Thr Arg Asp Gly Thr Met Gly Ile Ala Tyr Tyr Phe Asp Tyr
                115                 120                 125

Trp Gly Gln Gly Val Met Val Thr Val Ser Ser
    130                 135

<210> SEQ ID NO 79
<211> LENGTH: 127
<212> TYPE: PRT
<213> ORGANISM: Artificial
<220> FEATURE:
<223> OTHER INFORMATION: Light chain variable region of clone 669.

<400> SEQUENCE: 79

Met Met Ala Ala Val Gln Leu Leu Gly Leu Leu Leu Leu Trp Val Pro
 1               5                  10                  15

Ala Met Arg Cys Asp Ile Gln Met Thr Gln Ser Pro Ser Phe Leu Ser
                20                  25                  30

Ala Ser Val Gly Asp Arg Val Thr Ile Asn Cys Lys Ala Ser Gln Asn
            35                  40                  45

Ile Asn Arg Tyr Leu Asn Trp Tyr Gln Gln Lys Leu Gly Glu Ala Pro
 50                  55                  60

Lys Leu Leu Ile Tyr Asn Ala Asn Ser Leu Gln Thr Gly Ile Pro Ser
 65                  70                  75                  80

Arg Phe Ser Gly Ser Gly Ser Gly Thr Asp Phe Thr Leu Thr Ile Ser
                 85                  90                  95

Ser Leu Gln Pro Glu Asp Val Ala Thr Tyr Phe Cys Leu Gln His Asn
                100                 105                 110

Ser Trp Pro Tyr Thr Phe Gly Ala Gly Thr Lys Leu Glu Leu Lys
            115                 120                 125

<210> SEQ ID NO 80
<211> LENGTH: 5
<212> TYPE: PRT
<213> ORGANISM: Artificial
<220> FEATURE:
<223> OTHER INFORMATION: Heavy chain CDR1 of clone 699.

<400> SEQUENCE: 80

Ser Tyr Asp Ile Ser
 1               5

<210> SEQ ID NO 81
<211> LENGTH: 18
<212> TYPE: PRT
<213> ORGANISM: Artificial
<220> FEATURE:
<223> OTHER INFORMATION: Heavy chain CDR2 of clone 699.

<400> SEQUENCE: 81

Ala Ile Asn Pro Gly Ser Gly Gly Thr Gly Tyr Asn Glu Lys Phe Lys
```

-continued

```
1               5                   10                  15

Gly Lys

<210> SEQ ID NO 82
<211> LENGTH: 11
<212> TYPE: PRT
<213> ORGANISM: Artificial
<220> FEATURE:
<223> OTHER INFORMATION: Heavy chain CDR3 of clone 699.

<400> SEQUENCE: 82

Ile His Gly Gly Tyr Arg Tyr Trp Phe Ala Tyr
1               5                   10

<210> SEQ ID NO 83
<211> LENGTH: 10
<212> TYPE: PRT
<213> ORGANISM: Artificial
<220> FEATURE:
<223> OTHER INFORMATION: Light chain CDR1 of clone 699.

<400> SEQUENCE: 83

Arg Ala Ser Ser Ser Val Ser Tyr Met His
1               5                   10

<210> SEQ ID NO 84
<211> LENGTH: 7
<212> TYPE: PRT
<213> ORGANISM: Artificial
<220> FEATURE:
<223> OTHER INFORMATION: Light chain CDR2 of clone 699.

<400> SEQUENCE: 84

Asp Thr Ser Lys Leu Ala Ser
1               5

<210> SEQ ID NO 85
<211> LENGTH: 9
<212> TYPE: PRT
<213> ORGANISM: Artificial
<220> FEATURE:
<223> OTHER INFORMATION: Light chain CDR3 of clone 699.

<400> SEQUENCE: 85

Leu Gln Arg Ser Ser Tyr Pro Pro Thr
1               5

<210> SEQ ID NO 86
<211> LENGTH: 139
<212> TYPE: PRT
<213> ORGANISM: Artificial
<220> FEATURE:
<223> OTHER INFORMATION: Heavy chain variable region of clone 699.

<400> SEQUENCE: 86

Met Glu Trp Asn Trp Val Phe Leu Phe Leu Leu Ser Val Thr Ala Gly
1               5                   10                  15

Val His Ser Gln Val Gln Leu Gln Gln Ser Gly Ala Glu Leu Thr Lys
                20                  25                  30

Pro Gly Ser Ser Val Lys Ile Ser Cys Lys Ala Ser Gly Tyr Thr Phe
            35                  40                  45

Thr Ser Tyr Asp Ile Ser Trp Ile Lys Gln Arg Pro Gly Gln Ala Leu
        50                  55                  60

Glu Trp Ile Gly Ala Ile Asn Pro Gly Ser Gly Gly Thr Gly Tyr Asn
```

```
                65                  70                  75                  80
Glu Lys Phe Lys Gly Lys Ala Thr Leu Thr Val Asp Lys Ser Ser
                    85                  90                  95
Thr Ala Phe Met Gln Leu Ser Ser Leu Thr Pro Glu Asp Thr Ala Val
                100                 105                 110
Tyr Tyr Cys Ala Arg Ile His Gly Gly Tyr Arg Tyr Trp Phe Ala Tyr
                115                 120                 125
Trp Gly Gln Gly Thr Leu Val Thr Val Ser Ser
            130                 135
```

<210> SEQ ID NO 87
<211> LENGTH: 128
<212> TYPE: PRT
<213> ORGANISM: Artificial
<220> FEATURE:
<223> OTHER INFORMATION: Light chain variable region of clone 699.

<400> SEQUENCE: 87

```
Met Asp Phe Gln Val Gln Ser Phe Ser Leu Leu Leu Ile Ser Ile Thr
1               5                   10                  15
Val Ile Val Ser Ser Gly Glu Ile Val Leu Thr Gln Ser Pro Thr Thr
                20                  25                  30
Met Ala Ala Ser Pro Gly Glu Lys Val Thr Ile Thr Cys Arg Ala Ser
            35                  40                  45
Ser Ser Val Ser Tyr Met His Trp Phe Gln Gln Lys Ser Gly Thr Ser
        50                  55                  60
Pro Lys Pro Trp Ile Tyr Asp Thr Ser Lys Leu Ala Ser Gly Val Pro
65                  70                  75                  80
Asp Arg Phe Ser Gly Ser Gly Ser Gly Thr Ser Tyr Ser Leu Thr Ile
                85                  90                  95
Ser Ser Met Glu Ala Glu Asp Ala Ala Thr Tyr Tyr Cys Leu Gln Arg
                100                 105                 110
Ser Ser Tyr Pro Pro Thr Phe Gly Ala Gly Thr Lys Leu Glu Leu Lys
            115                 120                 125
```

<210> SEQ ID NO 88
<211> LENGTH: 5
<212> TYPE: PRT
<213> ORGANISM: Artificial
<220> FEATURE:
<223> OTHER INFORMATION: Heavy chain CDR1 of clone 1052.

<400> SEQUENCE: 88

```
Ser Asn Gly Val Gly
1               5
```

<210> SEQ ID NO 89
<211> LENGTH: 16
<212> TYPE: PRT
<213> ORGANISM: Artificial
<220> FEATURE:
<223> OTHER INFORMATION: Heavy chain CDR2 of clone 1052.

<400> SEQUENCE: 89

```
Thr Ile Trp Thr Gly Gly Gly Thr Asn Tyr Asn Ser Gly Val Gln Ser
1               5                   10                  15
```

<210> SEQ ID NO 90
<211> LENGTH: 7
<212> TYPE: PRT
<213> ORGANISM: Artificial

```
<220> FEATURE:
<223> OTHER INFORMATION: Heavy chain CDR3 of clone 1052.

<400> SEQUENCE: 90

Glu Tyr Met Gly Phe Asp Tyr
1               5

<210> SEQ ID NO 91
<211> LENGTH: 11
<212> TYPE: PRT
<213> ORGANISM: Artificial
<220> FEATURE:
<223> OTHER INFORMATION: Light chain CDR1 of clone 1052.

<400> SEQUENCE: 91

Lys Ala Ser Gln Asn Val Gly Ile Asn Val Gly
1               5                   10

<210> SEQ ID NO 92
<211> LENGTH: 7
<212> TYPE: PRT
<213> ORGANISM: Artificial
<220> FEATURE:
<223> OTHER INFORMATION: Light chain CDR2 of clone 1052.

<400> SEQUENCE: 92

Trp Ala Ser Asn Arg Asp Thr
1               5

<210> SEQ ID NO 93
<211> LENGTH: 9
<212> TYPE: PRT
<213> ORGANISM: Artificial
<220> FEATURE:
<223> OTHER INFORMATION: Light chain CDR3 of clone 1052.

<400> SEQUENCE: 93

Leu Gln His Asn Ser Tyr Pro Arg Thr
1               5

<210> SEQ ID NO 94
<211> LENGTH: 134
<212> TYPE: PRT
<213> ORGANISM: Artificial
<220> FEATURE:
<223> OTHER INFORMATION: Heavy chain variable region of clone 1052.

<400> SEQUENCE: 94

Met Ala Val Leu Val Leu Leu Cys Leu Val Thr Phe Pro Ser Cys
1               5                   10                  15

Val Leu Ser Gln Val Gln Leu Lys Glu Ser Gly Pro Gly Leu Met Gln
                20                  25                  30

Pro Ser Glu Thr Leu Ser Leu Thr Cys Thr Val Ser Gly Phe Ser Leu
        35                  40                  45

Thr Ser Asn Gly Val Gly Trp Val Arg Gln Pro Leu Gly Lys Gly Leu
    50                  55                  60

Val Trp Met Gly Thr Ile Trp Thr Gly Gly Thr Asn Tyr Asn Ser
65                  70                  75                  80

Gly Val Gln Ser Arg Leu Ser Ile Ser Arg Asp Thr Ser Lys Ser Gln
                85                  90                  95

Val Phe Leu Lys Met Asn Ser Leu Gln Pro Glu Asp Thr Gly Thr Tyr
                100                 105                 110

Tyr Cys Ala Arg Glu Tyr Met Gly Phe Asp Tyr Trp Gly Gln Gly Val
```

-continued

```
                 115                 120                 125

Met Val Thr Val Ser Ser
            130

<210> SEQ ID NO 95
<211> LENGTH: 127
<212> TYPE: PRT
<213> ORGANISM: Artificial
<220> FEATURE:
<223> OTHER INFORMATION: Light chain variable region of clone 1052.

<400> SEQUENCE: 95

Met Glu Leu Ile Ser Gln Val Phe Val Phe Leu Leu Trp Leu Ser
1               5                   10                  15

Gly Val Tyr Gly Asn Thr Val Met Thr Gln Ser Pro Thr Ser Met Phe
            20                  25                  30

Thr Ser Val Gly Asp Arg Val Thr Met Ser Cys Lys Ala Ser Gln Asn
        35                  40                  45

Val Gly Ile Asn Val Gly Trp Tyr Gln Gln Lys Thr Gly Gln Ser Pro
    50                  55                  60

Lys Arg Leu Ile Tyr Trp Ala Ser Asn Arg Asp Thr Gly Val Pro Asp
65                  70                  75                  80

Arg Phe Thr Gly Ser Gly Ser Gly Thr Asp Phe Thr Leu Thr Ile Ser
                85                  90                  95

Asn Met Gln Ala Glu Asp Pro Ala Ile Tyr Tyr Cys Leu Gln His Asn
            100                 105                 110

Ser Tyr Pro Arg Thr Phe Gly Gly Thr Lys Leu Glu Leu Lys
        115                 120                 125

<210> SEQ ID NO 96
<211> LENGTH: 5
<212> TYPE: PRT
<213> ORGANISM: Artificial
<220> FEATURE:
<223> OTHER INFORMATION: Heavy chain CDR1 of clone 1105.

<400> SEQUENCE: 96

Ser Asn Gly Val Gly
1               5

<210> SEQ ID NO 97
<211> LENGTH: 16
<212> TYPE: PRT
<213> ORGANISM: Artificial
<220> FEATURE:
<223> OTHER INFORMATION: Heavy chain CDR2 of clone 1105.

<400> SEQUENCE: 97

Thr Ile Trp Ser Gly Gly Gly Thr Asn Tyr Asn Ser Ala Val Gln Ser
1               5                   10                  15

<210> SEQ ID NO 98
<211> LENGTH: 7
<212> TYPE: PRT
<213> ORGANISM: Artificial
<220> FEATURE:
<223> OTHER INFORMATION: Heavy chain CDR3 of clone 1105.

<400> SEQUENCE: 98

Glu Glu Lys Gly Phe Ala Tyr
1               5
```

-continued

```
<210> SEQ ID NO 99
<211> LENGTH: 11
<212> TYPE: PRT
<213> ORGANISM: Artificial
<220> FEATURE:
<223> OTHER INFORMATION: Light chain CDR1 of clone 1105.

<400> SEQUENCE: 99

Lys Ala Ser Gln Asn Val Gly Ile Asn Val Gly
1               5                   10

<210> SEQ ID NO 100
<211> LENGTH: 7
<212> TYPE: PRT
<213> ORGANISM: Artificial
<220> FEATURE:
<223> OTHER INFORMATION: Light chain CDR2 of clone 1105.

<400> SEQUENCE: 100

Trp Ala Ser Asn Arg Asp Thr
1               5

<210> SEQ ID NO 101
<211> LENGTH: 9
<212> TYPE: PRT
<213> ORGANISM: Artificial
<220> FEATURE:
<223> OTHER INFORMATION: Light chain CDR3 of clone 1105.

<400> SEQUENCE: 101

Leu Gln His Asn Ser Tyr Pro Arg Ala
1               5

<210> SEQ ID NO 102
<211> LENGTH: 134
<212> TYPE: PRT
<213> ORGANISM: Artificial
<220> FEATURE:
<223> OTHER INFORMATION: Heavy chain variable region of clone 1105.

<400> SEQUENCE: 102

Met Ala Val Leu Val Leu Leu Cys Leu Val Thr Phe Pro Ser Cys
1               5                   10                  15

Val Leu Ser Gln Val Gln Leu Lys Glu Ser Gly Pro Gly Leu Met Gln
                20                  25                  30

Pro Ser Glu Thr Leu Ser Leu Thr Cys Thr Val Ser Gly Phe Ser Leu
                35                  40                  45

Thr Ser Asn Gly Val Gly Trp Val Arg Gln Pro Leu Gly Lys Gly Leu
        50                  55                  60

Val Trp Met Gly Thr Ile Trp Ser Gly Gly Gly Thr Asn Tyr Asn Ser
65                  70                  75                  80

Ala Val Gln Ser Arg Leu Ser Ile Thr Arg Asp Thr Ser Lys Ser Gln
                85                  90                  95

Val Phe Leu Lys Met Asn Ser Leu Gln Pro Glu Asp Thr Gly Thr Tyr
                100                 105                 110

Tyr Cys Ala Arg Glu Glu Lys Gly Phe Ala Tyr Trp Gly Gln Gly Thr
            115                 120                 125

Leu Val Thr Val Ser Ser
        130

<210> SEQ ID NO 103
<211> LENGTH: 127
<212> TYPE: PRT
```

-continued

```
<213> ORGANISM: Artificial
<220> FEATURE:
<223> OTHER INFORMATION: Light chain variable region of clone 1105.

<400> SEQUENCE: 103

Met Glu Leu Ile Ser Gln Val Phe Val Phe Leu Leu Trp Leu Ser
1               5                   10                  15

Gly Val Tyr Gly Asn Ile Val Met Thr Gln Ser Pro Thr Ser Met Ser
            20                  25                  30

Thr Ser Val Gly Asp Arg Val Thr Met Ser Cys Lys Ala Ser Gln Asn
                35                  40                  45

Val Gly Ile Asn Val Gly Trp Tyr Gln Gln Lys Thr Gly Gln Ser Pro
    50                  55                  60

Lys Arg Leu Ile Tyr Trp Ala Ser Asn Arg Asp Thr Gly Val Pro Asp
65                  70                  75                  80

Arg Phe Thr Gly Ser Gly Ser Gly Thr Asp Phe Thr Leu Thr Ile Ser
                85                  90                  95

Asn Met Gln Ala Glu Asp Pro Ala Ile Tyr Tyr Cys Leu Gln His Asn
                100                 105                 110

Ser Tyr Pro Arg Ala Phe Gly Gly Gly Thr Lys Leu Glu Leu Arg
        115                 120                 125

<210> SEQ ID NO 104
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 104

Cys Leu Tyr Asp Gly Phe Leu Thr Leu Val
1               5                   10

<210> SEQ ID NO 105
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 105

Phe Leu Leu Tyr Tyr Val Asp Thr Phe Val
1               5                   10

<210> SEQ ID NO 106
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 106

Phe Leu Trp Phe Val Ser Met Asp Leu Val
1               5                   10

<210> SEQ ID NO 107
<211> LENGTH: 10
<212> TYPE: PRT
<213> ORGANISM: Artificial
<220> FEATURE:
<223> OTHER INFORMATION: Predicted HLA type A2-binding peptide derived
``` from TMEM-180 protein.

<400> SEQUENCE: 107

Phe Leu Ser Leu Cys Arg Arg Trp Gly Val
1               5                   10

<210> SEQ ID NO 108
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 108

Phe Leu Leu Lys Leu Gly Leu Ser Leu Leu
1               5                   10

<210> SEQ ID NO 109
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 109

Lys Leu Leu Thr Leu Val Val Thr Asp Leu
1               5                   10

<210> SEQ ID NO 110
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 110

Ala Leu Leu Phe Gly Met Val Ala Leu Val
1               5                   10

<210> SEQ ID NO 111
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 111

Ala Leu Phe Thr Thr Ile Leu His Asn Val
1               5                   10

<210> SEQ ID NO 112
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 112

Trp Leu Leu Gly Leu Pro Thr Ala Val Val
1               5                   10

<210> SEQ ID NO 113

```
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 113

Gln Leu Phe Thr Trp Ser Gln Phe Thr Leu
1               5                   10

<210> SEQ ID NO 114
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 114

Leu Ala Leu Ser Phe Leu Ala Phe Trp Val
1               5                   10

<210> SEQ ID NO 115
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 115

Lys Leu Gly Leu Ser Leu Leu Met Leu Leu
1               5                   10

<210> SEQ ID NO 116
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 116

Gly Leu Gly Gln Pro Gln Ala Trp Leu Leu
1               5                   10

<210> SEQ ID NO 117
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 117

Thr Leu His Gly Arg Arg Leu His Met Val
1               5                   10

<210> SEQ ID NO 118
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 118
```

Leu Leu Trp Asn Ser Leu Asn Asp Pro Leu
1               5                   10

<210> SEQ ID NO 119
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 119

Ser Leu Asn Asp Pro Leu Phe Gly Trp Leu
1               5                   10

<210> SEQ ID NO 120
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 120

Thr Leu Val Asp Leu His His His Ala Leu
1               5                   10

<210> SEQ ID NO 121
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 121

Lys Met Ala Phe Trp Val Gly Glu Thr Val
1               5                   10

<210> SEQ ID NO 122
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 122

Tyr Leu Leu Val Leu Val Pro Ile Thr Cys
1               5                   10

<210> SEQ ID NO 123
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 123

Asn Leu Ser Gln Ala Gln Thr Leu Asp Val
1               5                   10

<210> SEQ ID NO 124
<211> LENGTH: 10
<212> TYPE: PRT
<213> ORGANISM: Artificial
<220> FEATURE:

```
<223> OTHER INFORMATION: Predicted HLA type A2-binding peptide derived
      from TMEM-180 protein.

<400> SEQUENCE: 124

Leu Leu Thr Leu Val Val Thr Asp Leu Val
1               5                   10

<210> SEQ ID NO 125
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 125

Leu Leu Ser Asp His Ile Ser Leu Ser Thr
1               5                   10

<210> SEQ ID NO 126
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 126

Leu Met Leu Leu Ala Gly Pro Asp His Leu
1               5                   10

<210> SEQ ID NO 127
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 127

Arg Gln Leu Ala Arg His Arg Asn Phe Leu
1               5                   10

<210> SEQ ID NO 128
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 128

Cys Leu Cys Leu Tyr Asp Gly Phe Leu Thr
1               5                   10

<210> SEQ ID NO 129
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 129

Leu Leu Cys Phe Tyr Thr Gly His Asp Leu
1               5                   10
```

```
<210> SEQ ID NO 130
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 130

Val Leu Val Pro Ile Thr Cys Ala Leu Leu
1               5                   10

<210> SEQ ID NO 131
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 131

Leu Leu Ala Gly Pro Asp His Leu Ser Leu
1               5                   10

<210> SEQ ID NO 132
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 132

Phe Gly Trp Leu Ser Asp Arg Gln Phe Leu
1               5                   10

<210> SEQ ID NO 133
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 133

Ser Leu Cys Arg Arg Trp Gly Val Tyr Ala
1               5                   10

<210> SEQ ID NO 134
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 134

Leu Gln Leu Phe Thr Trp Ser Gln Phe Thr
1               5                   10

<210> SEQ ID NO 135
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 135
```

```
<210> SEQ ID NO 136
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 136

Gly Leu Gly Phe Leu Gly Ala Thr Gln Leu
1               5                   10

<210> SEQ ID NO 137
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 137

Gly Leu Gln Phe Leu Leu Cys Leu Cys Leu
1               5                   10

<210> SEQ ID NO 138
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 138

Ala Leu Ser Ala His Asp Arg Thr His Leu
1               5                   10

<210> SEQ ID NO 139
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 139

Gln Leu Leu Arg Arg Arg Val Glu Ala Ala
1               5                   10

<210> SEQ ID NO 140
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 140

Val Val Tyr Gly Ser Leu Ala Leu Phe Thr
1               5                   10

<210> SEQ ID NO 141
<211> LENGTH: 10
<212> TYPE: PRT
<213> ORGANISM: Artificial
```

Phe Leu Ser Ser Gln Pro Arg Ser Gly Ala
1               5                   10

```
<220> FEATURE:
<223> OTHER INFORMATION: Predicted HLA type A2-binding peptide derived
      from TMEM-180 protein.

<400> SEQUENCE: 141

Leu Leu Val Leu Val Pro Ile Thr Cys Ala
1               5                   10

<210> SEQ ID NO 142
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.]

<400> SEQUENCE: 142

Leu Leu Phe Gly Met Val Ala Leu Val Thr
1               5                   10

<210> SEQ ID NO 143
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 143

Ser Met Asp Leu Val Gln Val Phe His Cys
1               5                   10

<210> SEQ ID NO 144
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 144

Ala Leu Leu Ala Asp Leu Ala Leu Ser Ala
1               5                   10

<210> SEQ ID NO 145
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 145

Tyr Ala Val Val Arg Gly Leu Phe Leu Leu
1               5                   10

<210> SEQ ID NO 146
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 146

Tyr Lys Ile Asn Lys Met Ala Phe Trp Val
1               5                   10
```

<210> SEQ ID NO 147
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 147

Phe Asn Ser Asn Phe Phe Pro Leu Phe Leu
1               5                   10

<210> SEQ ID NO 148
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 148

Leu Val Leu Val Pro Ile Thr Cys Ala Leu
1               5                   10

<210> SEQ ID NO 149
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 149

Gly Leu Ser Ser Arg Ala Val Val Leu Ala
1               5                   10

<210> SEQ ID NO 150
<211> LENGTH: 10
<212> TYPE: PRT
<213> ORGANISM: Artificial
<220> FEATURE:
<223> OTHER INFORMATION: Predicted HLA type A2-binding peptide derived
      from TMEM-180 protein.

<400> SEQUENCE: 150

Phe Ala Pro Leu Leu Gly Thr Trp Leu Leu
1               5                   10

<210> SEQ ID NO 151
<211> LENGTH: 10
<212> TYPE: PRT
<213> ORGANISM: Artificial
<220> FEATURE:
<223> OTHER INFORMATION: Predicted HLA type A24-binding peptide derived
       from TMEM-180 protein.

<400> SEQUENCE: 151

Ser Tyr Val Ala Pro His Leu Asn Asn Leu
1               5                   10

<210> SEQ ID NO 152
<211> LENGTH: 10
<212> TYPE: PRT
<213> ORGANISM: Artificial
<220> FEATURE:
<223> OTHER INFORMATION: Predicted HLA type A24-binding peptide derived
      from TMEM-180 protein.

```
<400> SEQUENCE: 152

Val Tyr Ala Val Val Arg Gly Leu Phe Leu
1               5                   10

<210> SEQ ID NO 153
<211> LENGTH: 10
<212> TYPE: PRT
<213> ORGANISM: Artificial
<220> FEATURE:
<223> OTHER INFORMATION: Predicted HLA type A24-binding peptide derived
      from TMEM-180 protein.

<400> SEQUENCE: 153

Ser Tyr Ala Phe Trp Asn Lys Glu Asp Phe
1               5                   10

<210> SEQ ID NO 154
<211> LENGTH: 10
<212> TYPE: PRT
<213> ORGANISM: Artificial
<220> FEATURE:
<223> OTHER INFORMATION: Predicted HLA type A24-binding peptide derived
      from TMEM-180 protein.

<400> SEQUENCE: 154

Asn Phe Leu Trp Phe Val Ser Met Asp Leu
1               5                   10

<210> SEQ ID NO 155
<211> LENGTH: 10
<212> TYPE: PRT
<213> ORGANISM: Artificial
<220> FEATURE:
<223> OTHER INFORMATION: Predicted HLA type A24-binding peptide derived
      from TMEM-180 protein.

<400> SEQUENCE: 155

Phe Phe Pro Leu Phe Leu Glu His Leu Leu
1               5                   10

<210> SEQ ID NO 156
<211> LENGTH: 10
<212> TYPE: PRT
<213> ORGANISM: Artificial
<220> FEATURE:
<223> OTHER INFORMATION: Predicted HLA type A24-binding peptide derived
      from TMEM-180 protein.

<400> SEQUENCE: 156

Leu Phe Leu Leu Lys Leu Gly Leu Ser Leu
1               5                   10

<210> SEQ ID NO 157
<211> LENGTH: 10
<212> TYPE: PRT
<213> ORGANISM: Artificial
<220> FEATURE:
<223> OTHER INFORMATION: Predicted HLA type A24-binding peptide derived
      from TMEM-180 protein.

<400> SEQUENCE: 157

Thr Phe Ala Pro Leu Leu Gly Thr Trp Leu
1               5                   10

<210> SEQ ID NO 158
<211> LENGTH: 10
<212> TYPE: PRT
```

```
<213> ORGANISM: Artificial
<220> FEATURE:
<223> OTHER INFORMATION: Predicted HLA type A24-binding peptide derived
      from TMEM-180 protein.

<400> SEQUENCE: 158

Val Phe Thr Glu Gly Thr Cys Lys Leu Leu
1               5                   10

<210> SEQ ID NO 159
<211> LENGTH: 10
<212> TYPE: PRT
<213> ORGANISM: Artificial
<220> FEATURE:
<223> OTHER INFORMATION: Predicted HLA type A24-binding peptide derived
      from TMEM-180 protein.

<400> SEQUENCE: 159

Asn Phe Phe Pro Leu Phe Leu Glu His Leu
1               5                   10

<210> SEQ ID NO 160
<211> LENGTH: 10
<212> TYPE: PRT
<213> ORGANISM: Artificial
<220> FEATURE:
<223> OTHER INFORMATION: Predicted HLA type A24-binding peptide derived
      from TMEM-180 protein.

<400> SEQUENCE: 160

Ala Phe Trp Val Gly Glu Thr Val Phe Leu
1               5                   10

<210> SEQ ID NO 161
<211> LENGTH: 10
<212> TYPE: PRT
<213> ORGANISM: Artificial
<220> FEATURE:
<223> OTHER INFORMATION: Predicted HLA type A24-binding peptide derived
      from TMEM-180 protein.

<400> SEQUENCE: 161

His Phe Asn Ser Asn Phe Phe Pro Leu Phe
1               5                   10

<210> SEQ ID NO 162
<211> LENGTH: 10
<212> TYPE: PRT
<213> ORGANISM: Artificial
<220> FEATURE:
<223> OTHER INFORMATION: Predicted HLA type A24-binding peptide derived
      from TMEM-180 protein.

<400> SEQUENCE: 162

Lys Leu Leu Thr Leu Val Val Thr Asp Leu
1               5                   10

<210> SEQ ID NO 163
<211> LENGTH: 10
<212> TYPE: PRT
<213> ORGANISM: Artificial
<220> FEATURE:
<223> OTHER INFORMATION: Predicted HLA type A24-binding peptide derived
      from TMEM-180 protein.

<400> SEQUENCE: 163

Val Phe Leu Leu Tyr Tyr Val Asp Thr Phe
1               5                   10
```

<210> SEQ ID NO 164
<211> LENGTH: 10
<212> TYPE: PRT
<213> ORGANISM: Artificial
<220> FEATURE:
<223> OTHER INFORMATION: Predicted HLA type A24-binding peptide derived
      from TMEM-180 protein.

<400> SEQUENCE: 164

Arg Gln Leu Ala Arg His Arg Asn Phe Leu
1               5                   10

<210> SEQ ID NO 165
<211> LENGTH: 10
<212> TYPE: PRT
<213> ORGANISM: Artificial
<220> FEATURE:
<223> OTHER INFORMATION: Predicted HLA type A24-binding peptide derived
      from TMEM-180 protein.

<400> SEQUENCE: 165

Arg Gly Leu Phe Leu Leu Lys Leu Gly Leu
1               5                   10

<210> SEQ ID NO 166
<211> LENGTH: 10
<212> TYPE: PRT
<213> ORGANISM: Artificial
<220> FEATURE:
<223> OTHER INFORMATION: Predicted HLA type A24-binding peptide derived
      from TMEM-180 protein.

<400> SEQUENCE: 166

Arg Gln Asn Leu Ser Gln Ala Gln Thr Leu
1               5                   10

<210> SEQ ID NO 167
<211> LENGTH: 10
<212> TYPE: PRT
<213> ORGANISM: Artificial
<220> FEATURE:
<223> OTHER INFORMATION: Predicted HLA type A24-binding peptide derived
      from TMEM-180 protein.

<400> SEQUENCE: 167

Leu Phe Thr Thr Ile Leu His Asn Val Phe
1               5                   10

<210> SEQ ID NO 168
<211> LENGTH: 10
<212> TYPE: PRT
<213> ORGANISM: Artificial
<220> FEATURE:
<223> OTHER INFORMATION: Predicted HLA type A24-binding peptide derived
      from TMEM-180 protein.

<400> SEQUENCE: 168

Ser Leu Asn Asp Pro Leu Phe Gly Trp Leu
1               5                   10

<210> SEQ ID NO 169
<211> LENGTH: 10
<212> TYPE: PRT
<213> ORGANISM: Artificial
<220> FEATURE:
<223> OTHER INFORMATION: Predicted HLA type A24-binding peptide derived
      from TMEM-180 protein.

<400> SEQUENCE: 169

Val Phe His Cys His Phe Asn Ser Asn Phe
1               5                   10

<210> SEQ ID NO 170
<211> LENGTH: 10
<212> TYPE: PRT
<213> ORGANISM: Artificial
<220> FEATURE:
<223> OTHER INFORMATION: Predicted HLA type A24-binding peptide derived
      from TMEM-180 protein.

<400> SEQUENCE: 170

Leu Phe Gly Trp Leu Ser Asp Arg Gln Phe
1               5                   10

CANCER-CELL-SPECIFIC ANTI-TMEM-180 MONOCLONAL ANTIBODY, ANTICANCER DRUG, AND CANCER TESTING METHOD

REFERENCE TO A SEQUENCE LISTING SUBMITTED VIA EFS-WEB

The content of the ASCII text file of the sequence listing named "20170307_101603_001US1_seq" which is 63.5 kb in size was created on Mar. 7, 2017 and electronically submitted via EFS-Web herewith the application is incorporated herein by reference in its entirety.

TECHNICAL FIELD

The present invention relates to a novel anti-TMEM-180 antibody, an anticancer drug containing an anti-TMEM-180 antibody, a cancer testing method involving measuring TMEM-180 in a sample, and the like.

BACKGROUND ART

Recently, numerous molecular targeted drugs that act specifically on a specific molecule have been developed for use as anticancer drugs. In particular, development has been proceeding on various antibody drugs having, as antigens, molecules specifically expressed in certain cancer cells or molecules exhibiting increased expression in cancer cells. In the development of such antibody drugs, a comparison is first made between expression of mRNA in cancer tissue collected at the time of surgery and expression of mRNA in normal tissue collected from a nearby site, molecules specifically expressed only in cancer tissue or molecules exhibiting increased expression in cancer tissue are identified, and antibodies are then prepared by using those molecules as antigens.

Colon cancer is manifest from cells of the intestinal mucosa. Cetuximab has previously been developed for use against colon cancer as an antibody drug that targets epidermal growth factor receptor (EGFR) (Non-Patent Documents 1 to 3). However, since EGFR is also expressed in normal tissue, Cetuximab also has the potential to act on normal tissue, thereby resulting in the desire to develop a molecular targeted drug that targets molecules more specifically expressed during colon cancer. With regard to this point, since there is only a small amount of mucosal tissue in which colon cancer occurs, there has been the problem of it being difficult to identify a target molecule by comparing cancerous mucosal cells and normal mucosal cells.

CITATION LIST

Non-Patent Documents

Non-Patent Document 1: Cunningham, D., et al., The New England Journal of Medicine, Vol. 351, No. 4, 2004, pp. 337-345

Non-Patent Document 2: Goldstein, N. I., et al., Clin. Cancer Res., Vol. 1, 1311-1318, 1995

Non-Patent Document 3: Karapetis, C. S., et al., The New Engl. J. Med., Vol. 359, 1757-1765

SUMMARY

Technical Problem

An object of the present invention is to provide an anticancer drug capable of treating cancer by finding a target molecule specifically expressed in cancer cells and by specifically acting on the target molecule, and to provide a cancer testing method comprising a step of measuring the target molecule in a sample.

Solution to Problem

In order to solve the above-mentioned problems, the inventors of the present invention compared mRNA expression between various types of colon cancer cell lines and normal mucosal cells contained in the washing liquid obtained during colonoscopy by analyzing using a DNA microarray to seek out molecules that are only expressed in colon cancer cell lines. As a result, transmembrane protein 180 (TMEM-180) was identified as a protein that is expressed in all colon cancer cell lines but which is not observed to be expressed in the cells of healthy subjects. Moreover, in addition to confirming that TMEM-180 is not expressed in normal colon tissue by quantitative PCR and in situ hybridization, TMEM-180 was also confirmed to not be expressed in prominent normal tissues, thereby confirming TMEM-180 to be an ideal molecule for use as a target of anticancer drugs and as an indicator in cancer testing.

Antibody to TMEM-180 was produced, and this antibody was confirmed to demonstrate a cytocidal effect on colon cancer cells as well as be able to detect recurrence in particular with greater sensitivity than conventional colon cancer markers, thereby leading to completion of the present invention.

Namely, the present invention is as indicated below.

[1] An anticancer drug containing, as an active ingredient thereof, an anti-transmembrane protein 180 (TMEM-180) antibody or an antigen-binding fragment thereof.

[2] An anticancer drug containing, as an active ingredient thereof, an anti-TMEM-180 antibody having a substance having anticancer activity bound thereto, or an antigen-binding fragment thereof.

[3] The anticancer drug described in [1] or [2] above, wherein the anti-TMEM-180 antibody has at least one of the six CDRs indicated below:

```
heavy chain CDR1:
                                      (SEQ ID NO: 1)
GFSLTRYNVH;

heavy chain CDR2:
                                      (SEQ ID NO: 2)
VIWTGGSTD;

heavy chain CDR3:
                                      (SEQ ID NO: 3)
DLGY;

light chain CDR1:
                                      (SEQ ID NO: 4)
KSSQSLKYRDGKTYLN;

light chain CDR2:
                                      (SEQ ID NO: 5)
QVSKLDS;
and light chain CDR3:
                                      (SEQ ID NO: 6)
CQGSYSPHT.
```

[4] The anticancer drug described in [1] or [2] above, wherein the anti-TMEM-180 antibody has at least one of the six CDRs indicated below:

heavy chain CDR1:
GFSLTSYYMQ; (SEQ ID NO: 7)

heavy chain CDR2:
FIRSGGSTE; (SEQ ID NO: 8)

heavy chain CDR3:
AFYGGYYFDY; (SEQ ID NO: 9)

light chain CDR1:
KASQNVGSNVD; (SEQ ID NO: 10)

light chain CDR2:
KASNRYT; (SEQ ID NO: 11)
and light chain CDR3:
MQSNTKYT. (SEQ ID NO: 12)

[5] The anticancer drug described in [1] or [2] above, wherein the anti-TMEM-180 antibody has at least one of the six CDRs indicated below:

heavy chain CDR1:
GFTFSDYAMA; (SEQ ID NO: 40)

heavy chain CDR2:
TIIYDGSST; (SEQ ID NO: 41)

heavy chain CDR3:
HWYWYFDF; (SEQ ID NO: 42)

light chain CDR1:
LASEGISNDLA; (SEQ ID NO: 43)

light chain CDR2:
AASRLQD; (SEQ ID NO: 44)
and light chain CDR3:
QQSYKYPLT. (SEQ ID NO: 45)

[6] The anticancer drug described in [1] or [2] above, wherein the anti-TMEM-180 antibody has at least one of the six CDRs indicated below:

heavy chain CDR1:
DCALN; (SEQ ID NO: 48)

heavy chain CDR2:
WINTQTGKPTYADDF; (SEQ ID NO: 49)

heavy chain CDR3:
EDYGYFDY; (SEQ ID NO: 50)

light chain CDR1:
QASQNINKFIA; (SEQ ID NO: 51)

light chain CDR2:
YTSTLVS; (SEQ ID NO: 52)
and light chain CDR3:
LQYDNLR. (SEQ ID NO: 53)

[7] The anticancer drug described in [1] or [2] above, wherein the anti-TMEM-180 antibody has at least one of the six CDRs indicated below:

heavy chain CDR1:
NYGMH; (SEQ ID NO: 56)

heavy chain CDR2:
SISPSGGSTYYRDSV; (SEQ ID NO: 57)

heavy chain CDR3:
SASITAYYYVMDA; (SEQ ID NO: 58)

light chain CDR1:
KASQNVGSNVD; (SEQ ID NO: 59)

light chain CDR2:
KASNRYT; (SEQ ID NO: 60)
and light chain CDR3:
MQSNSYPPT. (SEQ ID NO: 61)

[8] The anticancer drug described in [1] or [2] above, wherein the anti-TMEM-180 antibody has at least one of the six CDRs indicated below:

heavy chain CDR1:
NYWMT; (SEQ ID NO: 64)

heavy chain CDR2:
SITNTGGSTYYPDSV; (SEQ ID NO: 65)

heavy chain CDR3:
AGYSSYPDYFDY; (SEQ ID NO: 66)

light chain CDR1:
KAGQNIYNYLA; (SEQ ID NO: 67)

light chain CDR2:
NANSLQT; (SEQ ID NO: 68)
and light chain CDR3:
QQYSSGW. (SEQ ID NO: 69)

[9] The anticancer drug described in [1] or [2] above, wherein the anti-TMEM-180 antibody has at least one of the six CDRs indicated below:

heavy chain CDR1:
(SEQ ID NO: 72)
DYWVS;

heavy chain CDR2:
(SEQ ID NO: 73)
EIYPNSGATNFNENFK;

heavy chain CDR3:
(SEQ ID NO: 74)
DGTMGIAYYFDY;

light chain CDR1:
(SEQ ID NO: 75)
KASQNINRYLN;

light chain CDR2:
(SEQ ID NO: 76)
NANSLQT;
and light chain CDR3:
(SEQ ID NO: 77)
LQHNSWPYT.

[10] The anticancer drug described in [1] or [2] above, wherein the anti-TMEM-180 antibody has at least one of the six CDRs indicated below:

heavy chain CDR1:
(SEQ ID NO: 80)
SYDIS;

heavy chain CDR2:
(SEQ ID NO: 81)
AINPGSGGTGYNEKFKGK;

heavy chain CDR3:
(SEQ ID NO: 82)
IHGGYRYWFAY;

light chain CDR1:
(SEQ ID NO: 83)
RASSSVSYMH;

light chain CDR2:
(SEQ ID NO: 84)
DTSKLAS;
and light chain CDR3:
(SEQ ID NO: 85)
LQRSSYPPT.

[11] The anticancer drug described in [1] or [2] above, wherein the anti-TMEM-180 antibody has at least one of the six CDRs indicated below:

heavy chain CDR1:
(SEQ ID NO: 88)
SNGVG;

heavy chain CDR2:
(SEQ ID NO: 89)
TIWTGGGTNYNSGVQS;

heavy chain CDR3:
(SEQ ID NO: 90)
EYMGFDY;

light chain CDR1:
(SEQ ID NO: 91)
KASQNVGINVG;

light chain CDR2:
(SEQ ID NO: 92)
WASNRDT;
and light chain CDR3:
(SEQ ID NO: 93)
LQHNSYPRT.

[12] The anticancer drug described in [1] or [2] above, wherein the anti-TMEM-180 antibody has at least one of the six CDRs indicated below:

heavy chain CDR1:
(SEQ ID NO: 96)
SNGVG;

heavy chain CDR2:
(SEQ ID NO: 97)
TIWSGGGTNYNSAVQS;

heavy chain CDR3:
(SEQ ID NO: 98)
EEKGFAY;

light chain CDR1:
(SEQ ID NO: 99)
KASQNVGINVG;

light chain CDR2:
(SEQ ID NO: 100)
WASNRDT;
and light chain CDR3:
(SEQ ID NO: 101)
LQHNSYPRA.

[13] The anticancer drug described in any one of [3] to [12] above, wherein the anti-TMEM-180 antibody is such that
at least one of the heavy chain CDR1 to CDR3 and light chain CDR1 to CDR3 contains one to several amino acid additions, substitutions or deletions, or at least one of the heavy chain CDR1 to CDR3 and light chain CDR1 to CDR3 has an amino acid sequence having identity of 80% or more with the amino acid sequences of the heavy chain CDR1 to CDR3 and light chain CDR1 to CDR3.

[14] The anticancer drug described in [1] or [2] above, wherein the anti-TMEM-180 antibody contains:
a heavy chain containing the amino acid sequence represented by SEQ ID NO: 13;
a heavy chain containing an amino acid sequence containing one to several amino acid additions, substitutions or deletions in the amino acid sequence represented by SEQ ID NO: 13; or
a heavy chain containing an amino acid sequence having identity of 80% or more with the amino acid sequence represented by SEQ ID NO: 13, and/or
a light chain containing the amino acid sequence represented by SEQ ID NO: 14;
a light chain containing an amino acid sequence containing one to several amino acid additions, substitutions or deletions in the amino acid sequence represented by SEQ ID NO: 14; or
a light chain containing an amino acid sequence having identity of 80% or more with the amino acid sequence represented by SEQ ID NO: 14.

[15] The anticancer drug described in [1] or [2] above, wherein the anti-TMEM-180 antibody contains:

a heavy chain containing the amino acid sequence represented by SEQ ID NO: 15;

a heavy chain containing an amino acid sequence containing one to several amino acid additions, substitutions or deletions in the amino acid sequence represented by SEQ ID NO: 15; or a heavy chain containing an amino acid sequence having identity of 80% or more with the amino acid sequence represented by SEQ ID NO: 15, and/or a light chain containing the amino acid sequence represented by SEQ ID NO: 16;

a light chain containing an amino acid sequence containing one to several amino acid additions, substitutions or deletions in the amino acid sequence represented by SEQ ID NO: 16; or a light chain containing an amino acid sequence having identity of 80% or more with the amino acid sequence represented by SEQ ID NO: 16.

[16] The anticancer drug described in [1] or [2] above, wherein the anti-TMEM-180 antibody contains:

a heavy chain containing the amino acid sequence represented by SEQ ID NO: 46;

a heavy chain containing an amino acid sequence containing one to several amino acid additions, substitutions or deletions in the amino acid sequence represented by SEQ ID NO: 46; or a heavy chain containing an amino acid sequence having identity of 80% or more with the amino acid sequence represented by SEQ ID NO: 46, and/or a light chain containing the amino acid sequence represented by SEQ ID NO: 47;

a light chain containing an amino acid sequence containing one to several amino acid additions, substitutions or deletions in the amino acid sequence represented by SEQ ID NO: 47; or a light chain containing an amino acid sequence having identity of 80% or more with the amino acid sequence represented by SEQ ID NO: 47.

[17] The anticancer drug described in [1] or [2] above, wherein the anti-TMEM-180 antibody contains:

a heavy chain containing the amino acid sequence represented by SEQ ID NO: 54;

a heavy chain containing an amino acid sequence containing one to several amino acid additions, substitutions or deletions in the amino acid sequence represented by SEQ ID NO: 54; or a heavy chain containing an amino acid sequence having identity of 80% or more with the amino acid sequence represented by SEQ ID NO: 54, and/or a light chain containing the amino acid sequence represented by SEQ ID NO: 55;

a light chain containing an amino acid sequence containing one to several amino acid additions, substitutions or deletions in the amino acid sequence represented by SEQ ID NO: 55; or a light chain containing an amino acid sequence having identity of 80% or more with the amino acid sequence represented by SEQ ID NO: 55.

[18] The anticancer drug described in claim 1 or 2, wherein the anti-TMEM-180 antibody contains:

a heavy chain containing the amino acid sequence represented by SEQ ID NO: 62;

a heavy chain containing an amino acid sequence containing one to several amino acid additions, substitutions or deletions in the amino acid sequence represented by SEQ ID NO: 62; or a heavy chain containing an amino acid sequence having identity of 80% or more with the amino acid sequence represented by SEQ ID NO: 62, and/or a light chain containing the amino acid sequence represented by SEQ ID NO: 63;

a light chain containing an amino acid sequence containing one to several amino acid additions, substitutions or deletions in the amino acid sequence represented by SEQ ID NO: 63; or a light chain containing an amino acid sequence having identity of 80% or more with the amino acid sequence represented by SEQ ID NO: 63.

[19] The anticancer drug described in [1] or [2] above, wherein the anti-TMEM-180 antibody contains:

a heavy chain containing the amino acid sequence represented by SEQ ID NO: 70;

a heavy chain containing an amino acid sequence containing one to several amino acid additions, substitutions or deletions in the amino acid sequence represented by SEQ ID NO: 70; or a heavy chain containing an amino acid sequence having identity of 80% or more with the amino acid sequence represented by SEQ ID NO: 70, and/or a light chain containing the amino acid sequence represented by SEQ ID NO: 71;

a light chain containing an amino acid sequence containing one to several amino acid additions, substitutions or deletions in the amino acid sequence represented by SEQ ID NO: 71; or a light chain containing an amino acid sequence having identity of 80% or more with the amino acid sequence represented by SEQ ID NO: 71.

[20] The anticancer drug described in [1] or [2] above, wherein the anti-TMEM-180 antibody contains:

a heavy chain containing the amino acid sequence represented by SEQ ID NO: 78;

a heavy chain containing an amino acid sequence containing one to several amino acid additions, substitutions or deletions in the amino acid sequence represented by SEQ ID NO: 78; or a heavy chain containing an amino acid sequence having identity of 80% or more with the amino acid sequence represented by SEQ ID NO: 78, and/or a light chain containing the amino acid sequence represented by SEQ ID NO: 79;

a light chain containing an amino acid sequence containing one to several amino acid additions, substitutions or deletions in the amino acid sequence represented by SEQ ID NO: 79; or a light chain containing an amino acid sequence having identity of 80% or more with the amino acid sequence represented by SEQ ID NO: 79.

[21] The anticancer drug described in [1] or [2] above, wherein the anti-TMEM-180 antibody contains:

a heavy chain containing the amino acid sequence represented by SEQ ID NO: 86;

a heavy chain containing an amino acid sequence containing one to several amino acid additions, substitutions or deletions in the amino acid sequence represented by SEQ ID NO: 86; or a heavy chain containing an amino acid sequence having identity of 80% or more with the amino acid sequence represented by SEQ ID NO: 86, and/or a light chain containing the amino acid sequence represented by SEQ ID NO: 87;

a light chain containing an amino acid sequence containing one to several amino acid additions, substitutions or deletions in the amino acid sequence represented by SEQ ID NO: 87; or a light chain containing an amino acid sequence having identity of 80% or more with the amino acid sequence represented by SEQ ID NO: 87.

[22] The anticancer drug described in [1] or [2] above, wherein the anti-TMEM-180 antibody contains:

a heavy chain containing the amino acid sequence represented by SEQ ID NO: 94;

a heavy chain containing an amino acid sequence containing one to several amino acid additions, substitutions or deletions in the amino acid sequence represented by SEQ ID NO: 94; or a heavy chain containing an amino acid sequence having identity of 80% or more with the amino acid sequence represented by SEQ ID NO: 94, and/or a light chain containing the amino acid sequence represented by SEQ ID NO: 95;

a light chain containing an amino acid sequence containing one to several amino acid additions, substitutions or deletions in the amino acid sequence represented by SEQ ID NO: 95; or a light chain containing an amino acid sequence having identity of 80% or more with the amino acid sequence represented by SEQ ID NO: 95.

[23] The anticancer drug described in [1] or [2] above, wherein the anti-TMEM-180 antibody contains:

a heavy chain containing the amino acid sequence represented by SEQ ID NO: 102;

a heavy chain containing an amino acid sequence containing one to several amino acid additions, substitutions or deletions in the amino acid sequence represented by SEQ ID NO: 102; or a heavy chain containing an amino acid sequence having identity of 80% or more with the amino acid sequence represented by SEQ ID NO: 102, and/or a light chain containing the amino acid sequence represented by SEQ ID NO: 103;

a light chain containing an amino acid sequence containing one to several amino acid additions, substitutions or deletions in the amino acid sequence represented by SEQ ID NO: 103; or a light chain containing an amino acid sequence having identity of 80% or more with the amino acid sequence represented by SEQ ID NO: 103.

[24] The anticancer drug described in any one of [1] to [23] above, wherein the anti-TMEM-180 antibody has one or more N-linked oligosaccharides bound to the Fc region and fucose is not bound to N-acetylglucosamine on the reducing end of the N-linked oligosaccharide.

[25] The anticancer drug described in any one of [1] to [24] above, which is targeted at cancer expressing TMEM-180.

[26] The anticancer drug described in any one of [1] to [24] above, which is targeted at colon cancer.

[27] The anticancer drug described in any one of [1] to [24] above, which is administered concomitantly with vaccine therapy using a composition containing at least one peptide comprising an amino acid sequence represented by SEQ ID NOs: 104 to 170.

[28] An anti-TMEM-180 antibody described in any one of [3] to [24] above or an antigen-binding fragment thereof.

[29] A nucleic acid encoding any one of the heavy chains CDR1 to CDR3 and light chains CDR1 to CDR3 described in any one of [3] to [13] above.

[30] A nucleic acid encoding any one of the heavy chains and light chains described in any one of [14] to [23] above.

[31] An expression vector containing the nucleic acid described in [29] or [30] above.

[32] A transformant containing the expression vector described in [31] above.

[33] A method for producing an anti-TMEM-180 antibody, or an antigen-binding fragment thereof, the method comprising the steps of:

expressing an antibody in the transformant described in [32] above; and recovering the antibody.

[34] A cancer testing method, comprising a step of measuring the amount of TMEM-180 in a sample collected from a subject.

[35] The cancer testing method described in [34] above, wherein the amount of TMEM-180 is measured by immunoassay using an anti-TMEM-180 antibody or an antigen-binding fragment thereof.

[36] The cancer testing method described in [35] above, wherein the anti-TMEM-180 antibody or antigen-binding fragment thereof is the anti-TMEM-180 antibody or antigen-binding fragment thereof described in [28] above.

[37] The cancer testing method described in any one of [34] to [36] above, which is targeted at colon cancer.

[38] The cancer testing method described in [34] to [37], which is used to test for recurrence or metastasis following treatment.

[39] A cancer testing kit containing an anti-TMEM-180 antibody or an antigen-binding fragment thereof.

[40] The cancer testing kit described in [39] above, wherein the anti-TMEM-180 antibody or antigen-binding fragment thereof is the anti-TMEM-180 antibody or antigen-binding fragment thereof described in [28] above.

[41] The cancer testing kit described in [39] or [40] above, which is targeted at colon cancer.

Advantageous Effects of Invention

The anticancer drug containing an anti-TMEM-180 antibody or an antigen-binding fragment thereof according to the present invention targets TMEM-180, which is a protein specifically expressed in certain cancers but is not expressed in normal tissue, and is thought to allow the obtaining of a potent effect specific to cancer cells with few adverse side effects.

Since TMEM-180 is specifically expressed in certain cancers but not expressed in normal tissue, a cancer testing method and testing kit that uses the anti-TMEM-180 antibody or antigen-binding fragment thereof according to the present invention enables cancer testing to be carried out easily. The cancer testing method and testing kit according to the present invention are able to detect recurrence of cancer in particular with greater sensitivity in comparison with conventional colon cancer markers.

In addition, according to the anticancer drug containing an anti-TMEM-180 antibody having a substance having anticancer activity bound thereto, or an antigen-binding fragment thereof, according to the present invention, that anticancer drug can be specifically delivered to cancer cells expressing TMEM-180, thereby facilitating the use of a highly toxic substance for the substance having anticancer activity.

BRIEF DESCRIPTION OF THE DRAWINGS

FIG. 1A indicates expression levels of TMEM-180 obtained as a result of conducting an exhaustive expression analysis on human colon cancer cell lines and colon mucosal cells obtained from healthy subjects by DNA microarray analysis. FIG. 1B indicates the results of analyzing expression of TMEM-180 in colon cancer cells and adjacent normal colon tissue by quantitative PCR. FIGS. 1C and 1D indicate the results of investigating expression of TMEM-180 at cancerous sites and normal sites by in situ hybridization.

DESCRIPTION OF EMBODIMENTS

Anti-TMEM-180 Antibody and Anticancer Drug

Figure 2A:
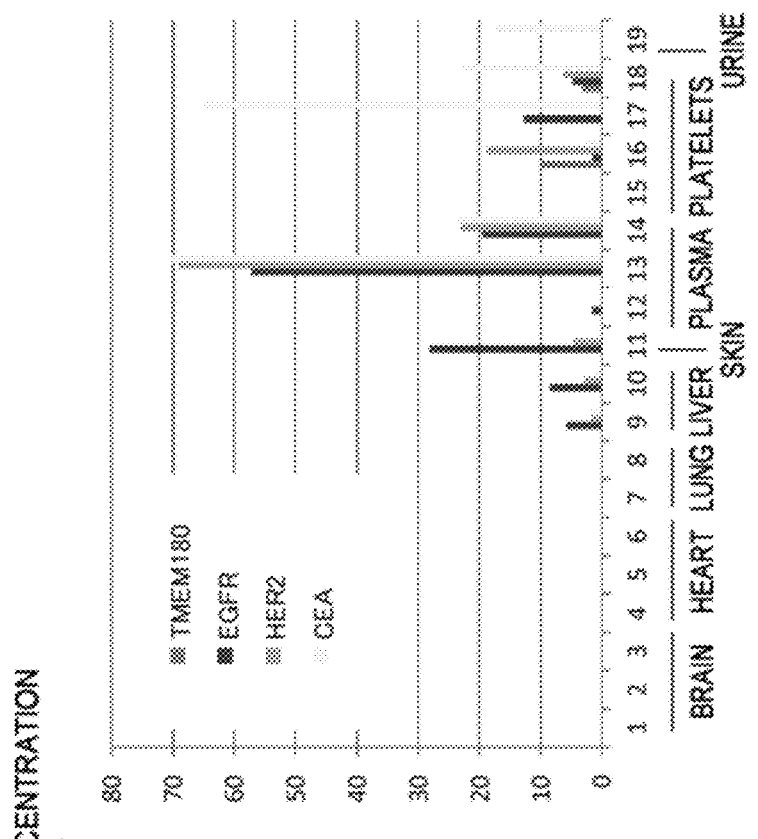
FIG. 2A indicates the results of investigating expression of TMEM-180 in various normal tissues using a database.

One aspect of the anticancer drug according to the present invention contains an anti-TMEM-180 antibody, or an antigen-binding fragment thereof, as active ingredient.

In the present description, the anti-TMEM-180 antibody refers to an antibody that specifically binds to transmembrane protein 180 (TMEM-180). In the present description, in the case of referring to TMEM-180, the TMEM-180 may be TMEM-180 derived from any animal, and may be a mutant thereof provided it serves as a target of an anticancer drug or an indicator of a cancer testing method. The amino acid sequence of human TMEM-180 is indicated in SEQ ID NO: 17 as an example of TMEM-180.

In the present description, an "antibody" refers to a protein having a structure of the association of two heavy chains (H chains) and two light chains (L chains) that are stabilized by a pair of disulfide bonds. The heavy chains are formed from a heavy chain variable region VH, heavy chain constant regions CH1, CH2 and CH3, and a hinge region between CH1 and CH2, while the light chains are formed from a light chain variable region VL and a light chain constant region CL. Among these chains, a variable region fragment (Fv) formed of VH and VL is directly involved in antigen binding and is a region that provides the antibody with diversity. In addition, an antigen-binding region formed of VL, CL, VH and CH1 is referred to as the Fab region, while the region formed of the hinge region, CH2 and CH3 is referred to as the Fc region.

Among the variable regions, the region that makes direct contact with antigen undergoes considerable change in particular, and is referred to as a complementarity-determining region (CDR). The region other than CDR that remains comparatively unchanged is referred to as the framework region (FR). Three CDRs each are present in the variable regions of the light chain and heavy chain, and are referred to as heavy chain CDR1 to CDR3 and light chain CDR1 to CDR3, respectively, in order starting from the side of the N-terminal.

The anti-TMEM-180 antibody according to the present invention may be a monoclonal antibody or polyclonal antibody. In addition, the anti-TMEM-180 antibody of the present invention may be an isotype of any of IgG, IgM, IgA, IgD or IgE. It may also be that produced by immunizing a non-human animal such as a mouse, rat, hamster, guinea pig, rabbit or chicken, or may be a recombinant antibody, chimeric antibody, humanized antibody, fully human antibody or the like. A chimeric antibody refers to an antibody in which fragments of antibodies from different species are linked.

A "humanized antibody" refers to an antibody in which a location corresponding to human antibody has been substituted with an amino acid sequence specific to an antibody from a non-human origin, and an example thereof is an antibody that has the heavy chain CDR1 to CDR3 and light chain CDR1 to CDR3 of an antibody produced by immunizing a mouse or rat, and in which all other regions, including each of the four framework regions (FR) of the heavy chain and light chain, are derived from human antibody. This type of antibody may also be referred to as a CDR-grafted antibody. The term "humanized antibody" may also include human chimeric antibody.

In the present description, an "antigen-binding fragment" of the anti-TMEM-180 antibody refers to a fragment of the anti-TMEM-180 antibody that binds to TMEM-180. More specifically, examples thereof include, but are not limited to, Fab formed of a VL, VH, CL and CH1 region, F(ab')2 obtained by linking two Fab in a hinge region with disulfide bonds, Fv formed of VL and VH, single-stranded antibody in the form of scFv, in which VL and VH are linked with an artificial polypeptide linker, as well as bispecific antibodies such as diabodies, scDb, tandem sdFv and leucine zippers.

One aspect of the anti-TMEM-180 antibody according to the present invention has at least one of the six CDRs indicated below. These CDRs are the CDR sequences of anti-TMEM-180 antibody clone 98 indicated in the examples to be subsequently described.

Heavy chain CDR1:
GFSLTRYNVH (SEQ ID NO: 1)

Heavy chain CDR2:
VIWTGGSTD (SEQ ID NO: 2)

Heavy chain CDR3:
DLGY (SEQ ID NO: 3)

Light chain CDR1:
KSSQSLKYRDGKTYLN (SEQ ID NO: 4)

Light chain CDR2:
QVSKLDS (SEQ ID NO: 5)

Light chain CDR3:
CQGSYSPHT (SEQ ID NO: 6)

One aspect of the anti-TMEM-180 antibody according to the present invention has at least one of the six CDRs indicated below. These CDRs are the CDR sequences of anti-TMEM-180 antibody clone 101 indicated in the examples to be subsequently described.

Heavy chain CDR1:
GFSLTSYYMQ (SEQ ID NO: 7)

Heavy chain CDR2:
FIRSGGSTE (SEQ ID NO: 8)

Heavy chain CDR3:
AFYGGYYFDY (SEQ ID NO: 9)

Light chain CDR1:
KASQNVGSNVD (SEQ ID NO: 10)

Light chain CDR2:
KASNRYT (SEQ ID NO: 11)

Light chain CDR3:
MQSNTKYT (SEQ ID NO: 12)

One aspect of the anti-TMEM-180 antibody according to the present invention has at least one of the six CDRs indicated below. These CDRs are the CDR sequences of anti-TMEM-180 antibody clone 212 indicated in the examples to be subsequently described.

Heavy chain CDR1:
GFTFSDYAMA (SEQ ID NO: 40)

Heavy chain CDR2:
TIIYDGSST (SEQ ID NO: 41)

Heavy chain CDR3:
HWYWYFDF (SEQ ID NO: 42)

Light chain CDR1:
LASEGISNDLA (SEQ ID NO: 43)

Light chain CDR2:
AASRLQD (SEQ ID NO: 44)

Light chain CDR3:
QQSYKYPLT (SEQ ID NO: 45)

One aspect of the anti-TMEM-180 antibody according to the present invention has at least one of the six CDRs indicated below. These CDRs are the CDR sequences of anti-TMEM-180 antibody clone 129 indicated in the examples to be subsequently described.

Heavy chain CDR1:
DCALN (SEQ ID NO: 48)

Heavy chain CDR2:
WINTQTGKPTYADDF (SEQ ID NO: 49)

Heavy chain CDR3:
EDYGYFDY (SEQ ID NO: 50)

Light chain CDR1:
QASQNINKFIA (SEQ ID NO: 51)

Light chain CDR2:
YTSTLVS (SEQ ID NO: 52)

Light chain CDR3:
LQYDNLR (SEQ ID NO: 53)

One aspect of the anti-TMEM-180 antibody according to the present invention has at least one of the six CDRs indicated below. These CDRs are the CDR sequences of anti-TMEM-180 antibody clone 382 indicated in the examples to be subsequently described.

Heavy chain CDR1:
NYGMH (SEQ ID NO: 56)

Heavy chain CDR2:
SISPSGGSTYYRDSV (SEQ ID NO: 57)

Heavy chain CDR3:
SASITAYYYVMDA (SEQ ID NO: 58)

Light chain CDR1:
KASQNVGSNVD (SEQ ID NO: 59)

Light chain CDR2:
KASNRYT (SEQ ID NO: 60)

Light chain CDR3:
MQSNSYPPT (SEQ ID NO: 61)

One aspect of the anti-TMEM-180 antibody according to the present invention has at least one of the six CDRs indicated below. These CDRs are the CDR sequences of anti-TMEM-180 antibody clone 1361 indicated in the examples to be subsequently described.

Heavy chain CDR1:
(SEQ ID NO: 64)
NYWMT

Heavy chain CDR2:
(SEQ ID NO: 65)
SITNTGGSTYYPDSV

Heavy chain CDR3:
(SEQ ID NO: 66)
AGYSSYPDYFDY

Light chain CDR1:
(SEQ ID NO: 67)
KAGQNIYNYLA

Light chain CDR2:
(SEQ ID NO: 68)
NANSLQT

Light chain CDR3:
(SEQ ID NO: 69)
QQYSSGW

One aspect of the anti-TMEM-180 antibody according to the present invention has at least one of the six CDRs indicated below. These CDRs are the CDR sequences of anti-TMEM-180 antibody clone 669 indicated in the examples to be subsequently described.

Heavy chain CDR1:
(SEQ ID NO: 72)
DYWVS

Heavy chain CDR2:
(SEQ ID NO: 73)
EIYPNSGATNFNENFK

Heavy chain CDR3:
(SEQ ID NO: 74)
DGTMGIAYYFDY

Light chain CDR1:
(SEQ ID NO: 75)
KASQNINRYLN

Light chain CDR2:
(SEQ ID NO: 76)
NANSLQT

Light chain CDR3:
(SEQ ID NO: 77)
LQHNSWPYT

One aspect of the anti-TMEM-180 antibody according to the present invention has at least one of the six CDRs indicated below. These CDRs are the CDR sequences of anti-TMEM-180 antibody clone 699 indicated in the examples to be subsequently described.

Heavy chain CDR1:
(SEQ ID NO: 80)
SYDIS

Heavy chain CDR2:
(SEQ ID NO: 81)
AINPGSGGTGYNEKFKGK

Heavy chain CDR3:
(SEQ ID NO: 82)
IHGGYRYWFAY

Light chain CDR1:
(SEQ ID NO: 83)
RASSSVSYMH

Light chain CDR2:
(SEQ ID NO: 84)
DTSKLAS

Light chain CDR3:
(SEQ ID NO: 85)
LQRSSYPPT

One aspect of the anti-TMEM-180 antibody according to the present invention has at least one of the six CDRs indicated below. These CDRs are the CDR sequences of anti-TMEM-180 antibody clone 1052 indicated in the examples to be subsequently described.

Heavy chain CDR1:
(SEQ ID NO: 88)
SNGVG

Heavy chain CDR2:
(SEQ ID NO: 89)
TIWTGGGTNYNSGVQS

Heavy chain CDR3:
(SEQ ID NO: 90)
EYMGFDY

Light chain CDR1:
(SEQ ID NO: 91)
KASQNVGINVG

Light chain CDR2:
(SEQ ID NO: 92)
WASNRDT

Light chain CDR3:
(SEQ ID NO: 93)
LQHNSYPRT

One aspect of the anti-TMEM-180 antibody according to the present invention has at least one of the six CDRs indicated below. These CDRs are the CDR sequences of anti-TMEM-180 antibody clone 1105 indicated in the examples to be subsequently described.

Heavy chain CDR1:
(SEQ ID NO: 96)
SNGVG

Heavy chain CDR2:
(SEQ ID NO: 97)
TIWSGGGTNYNSAVQS

Heavy chain CDR3:
(SEQ ID NO: 98)
EEKGFAY

Light chain CDR1:
(SEQ ID NO: 99)
KASQNVGINVG

Light chain CDR2:
(SEQ ID NO: 100)
WASNRDT

Light chain CDR3:
(SEQ ID NO: 101)
LQHNSYPRA

In each of the above-mentioned aspects, although the anti-TMEM-180 antibody may contain any of the six CDRs provided the effects of the present invention are demonstrated, it can also contain, for example, two or more, three or more, four or more, five or more or all six of the six CDRs.

In each of the above-mentioned aspects, at least one of heavy chain CDR1 to CDR3 and light chain CDR1 to CDR3 may contain one to several amino acid additions, substitutions or deletions.

In the present description, an "amino acid" is used in the broadest sense, and includes artificial amino acid variants and derivatives in addition to naturally-occurring amino acids. Amino acids may be indicated using customary one-letter or three-letter codes. In the present description, examples of amino acids or derivatives thereof include natural protein L-amino acids, unnatural amino acids, and chemically synthesized compounds having properties widely known in the art to be properties of amino acids. Examples of unnatural amino acids include, but are not limited to, α,α-disubstituted amino acids (such as α-methylalanine), N-alkyl-α-amino acids, D-amino acids, β-amino acids and α-hydroxy acids having main chain structures that differ from those occurring naturally, amino acids having side chain structures that differ from those occurring naturally (such as norleucine or homohistidine), amino acids having a surplus methylene in a side chain thereof (such as homoamino acid, homophenylalanine or homohistidine), and amino acids in which a carboxylic acid functional group has been substituted with a sulfonic acid group in a side chain thereof (such as cysteic acid).

In the present description, in the case of referring to "having one to several amino acid additions, substitutions or deletions", although there are no particular limitations on the number of, for example, added, substituted or deleted amino acids provided the polypeptide obtained as a result thereof retains the function of a CDR, examples thereof include one, two, three or four amino acid additions, substitutions or deletions. The substituted or added amino acids may be unnatural amino acids or amino acid analogs in addition to natural protein amino acids. The location of an amino acid deletion, substitution or addition may be at any location of the original CDR sequence provided the function of a CDR is retained.

In each of the aspects of the above-mentioned anti-TMEM-180 antibody, at least one of the heavy chain CDR1 to CDR3 and light chain CDR1 to CDR3 may have an amino acid sequence having identity of 80% or more with the original amino acid sequences of the heavy chain CDR1 to CDR3 and light chain CDR1 to CDR3.

In the present description, "having identity of 80% or more" means that the number of common amino acid residues is 80% or more of the amino acids of the original sequence when the amino acid sequence of a polypeptide having the original sequence is aligned with the amino acid sequence of a polypeptide having a mutated sequence so that there is maximum agreement between the two.

Identity may be of any percentage of 80% or more that retains the function of a CDR, and can be, for example, 85% or more, 90% or more, 95% or more, 98% or more or 99% or more.

A CDR comprising an amino acid sequence in which an amino acid has been added, substituted or deleted in the amino acid sequences of heavy chain CDR1 to CDR3 and light chain CDR1 to CDR3, or a CDR having sequence identity of 80% or more with the amino acid sequences of heavy chain CDR1 to CDR3 and light chain CDR1 to CDR3, can be produced using a known method such as site-specific mutagenesis, random mutagenesis, chain shuffling or CDR walking. According to these methods, antibody or antigen fragments having various mutations in the CDR thereof can be presented on a phage surface by phage display, and CDRs having a higher degree of affinity maturation are well known among persons with ordinary skill in the art to be obtained by screening using antigen (see, for example, Wu, et al., PNAS, 95: 6037-6042 (1998); Schier, R., et al., J. Mol. Biol., 263, 551-567 (1996); Schier, R., et al., J. Mol. Biol., 255, 28-43 (1996); Yang, W. P., et al., J. Mol. Biol., 254, 392-403 (1995)).

Another aspect of the anti-TMEM-180 antibody according to the present invention contains:

a heavy chain containing the amino acid sequence represented by SEQ ID NO: 13;

a heavy chain containing an amino acid sequence containing one to several amino acid additions, substitutions or deletions in the amino acid sequence represented by SEQ ID NO: 13; or a heavy chain containing an amino acid sequence having identity of 80% or more with the amino acid sequence represented by SEQ ID NO: 13.

The amino acid sequence represented by SEQ ID NO: 13 is an amino acid sequence of the heavy chain variable region of anti-TMEM-180 antibody clone 98.

In the present description, in the case of one to several amino acid additions, substitutions or deletions in the amino acid sequence of the heavy chain or light chain, the number of amino acids that are added, substituted or deleted can be, for example, one, two, three, four, five, six, seven, eight, nine, or ten. Other terms are as previously described.

Another aspect of the anti-TMEM-180 antibody according to the present invention contains:

a light chain containing the amino acid sequence represented by SEQ ID NO: 14;

a light chain containing an amino acid sequence containing one to several amino acid additions, substitutions or deletions in the amino acid sequence represented by SEQ ID NO: 14; or a light chain containing an amino acid sequence having identity of 80% or more with the amino acid sequence represented by SEQ ID NO: 14.

The amino acid sequence represented by SEQ ID NO: 14 is an amino acid sequence of the light chain variable region of anti-TMEM-180 antibody clone 98.

The anti-TMEM-180 antibody according to the present invention may contain a heavy chain containing the amino acid sequence represented by SEQ ID NO: 13, a heavy chain containing an amino acid sequence containing one to several amino acid additions, substitutions or deletions in the amino acid sequence represented by SEQ ID NO: 13, or a heavy chain containing an amino acid sequence having identity of 80% or more with the amino acid sequence represented by SEQ ID NO: 13, and a light chain containing the amino acid sequence represented by SEQ ID NO: 14, a light chain containing an amino acid sequence containing one to several amino acid additions, substitutions or deletions in the amino acid sequence represented by SEQ ID NO: 14, or a light chain containing an amino acid sequence having identity of 80% or more with the amino acid sequence represented by SEQ ID NO: 14.

Another aspect of the anti-TMEM-180 antibody according to the present invention contains:

a heavy chain containing the amino acid sequence represented by SEQ ID NO: 15;

a heavy chain containing an amino acid sequence containing one to several amino acid additions, substitutions or deletions in the amino acid sequence represented by SEQ ID NO: 15; or a heavy chain containing an amino acid sequence having identity of 80% or more with the amino acid sequence represented by SEQ ID NO: 15.

The amino acid sequence represented by SEQ ID NO: 15 is an amino acid sequence of the heavy chain variable region of anti-TMEM-180 antibody clone 101.

Another aspect of the anti-TMEM-180 antibody according to the present invention contains:

a light chain containing the amino acid sequence represented by SEQ ID NO: 16;

a light chain containing an amino acid sequence containing one to several amino acid additions, substitutions or deletions in the amino acid sequence represented by SEQ ID NO: 16; or a light chain containing an amino acid sequence having identity of 80% or more with the amino acid sequence represented by SEQ ID NO: 16.

The amino acid sequence represented by SEQ ID NO: 16 is an amino acid sequence of the light chain variable region of anti-TMEM-180 antibody clone 101.

Another aspect of the anti-TMEM-180 antibody according to the present invention may contain a heavy chain containing the amino acid sequence represented by SEQ ID NO: 15, a heavy chain containing an amino acid sequence containing one to several amino acid additions, substitutions or deletions in the amino acid sequence represented by SEQ ID NO: 15, or a heavy chain containing an amino acid sequence having identity of 80% or more with the amino acid sequence represented by SEQ ID NO: 15, and a light chain containing the amino acid sequence represented by SEQ ID NO: 16, a light chain containing an amino acid sequence containing one to several amino acid additions, substitutions or deletions in the amino acid sequence represented by SEQ ID NO: 16, or a light chain containing an amino acid sequence having identity of 80% or more with the amino acid sequence represented by SEQ ID NO: 16.

Another aspect of the anti-TMEM-180 antibody according to the present invention contains:

a heavy chain containing the amino acid sequence represented by SEQ ID NO: 46;

a heavy chain containing an amino acid sequence containing one to several amino acid additions, substitutions or deletions in the amino acid sequence represented by SEQ ID NO: 46; or a heavy chain containing an amino acid sequence having identity of 80% or more with the amino acid sequence represented by SEQ ID NO: 46.

The amino acid sequence represented by SEQ ID NO: 46 is an amino acid sequence of the heavy chain variable region of anti-TMEM-180 antibody clone 212.

Another aspect of the anti-TMEM-180 antibody according to the present invention contains:

a light chain containing the amino acid sequence represented by SEQ ID NO: 47;

a light chain containing an amino acid sequence containing one to several amino acid additions, substitutions or deletions in the amino acid sequence represented by SEQ ID NO: 47; or a light chain containing an amino acid sequence having identity of 80% or more with the amino acid sequence represented by SEQ ID NO: 47.

The amino acid sequence represented by SEQ ID NO: 47 is an amino acid sequence of the light chain variable region of anti-TMEM-180 antibody clone 212.

Another aspect of the anti-TMEM-180 antibody according to the present invention may contain a heavy chain containing the amino acid sequence represented by SEQ ID NO: 46, a heavy chain containing an amino acid sequence containing one to several amino acid additions, substitutions or deletions in the amino acid sequence represented by SEQ ID NO: 46, or a heavy chain containing an amino acid sequence having identity of 80% or more with the amino acid sequence represented by SEQ ID NO: 46, and a light chain containing the amino acid sequence represented by SEQ ID NO: 47, a light chain containing an amino acid sequence containing one to several amino acid additions, substitutions or deletions in the amino acid sequence represented by SEQ ID NO: 47, or a light chain containing an amino acid sequence having identity of 80% or more with the amino acid sequence represented by SEQ ID NO: 47.

Another aspect of the anti-TMEM-180 antibody according to the present invention contains:

a heavy chain containing the amino acid sequence represented by SEQ ID NO: 54;

a heavy chain containing an amino acid sequence containing one to several amino acid additions, substitutions or deletions in the amino acid sequence represented by SEQ ID NO: 54; or a heavy chain containing an amino acid sequence having identity of 80% or more with the amino acid sequence represented by SEQ ID NO: 54.

The amino acid sequence represented by SEQ ID NO: 54 is an amino acid sequence of the heavy chain variable region of anti-TMEM-180 antibody clone 129.

Another aspect of the anti-TMEM-180 antibody according to the present invention contains:

a light chain containing the amino acid sequence represented by SEQ ID NO: 55;

a light chain containing an amino acid sequence containing one to several amino acid additions, substitutions or deletions in the amino acid sequence represented by SEQ ID NO: 55; or a light chain containing an amino acid sequence having identity of 80% or more with the amino acid sequence represented by SEQ ID NO: 55.

The amino acid sequence represented by SEQ ID NO: 55 is an amino acid sequence of the light chain variable region of anti-TMEM-180 antibody clone 129.

Another aspect of the anti-TMEM-180 antibody according to the present invention may contain a heavy chain containing the amino acid sequence represented by SEQ ID NO: 54, a heavy chain containing an amino acid sequence containing one to several amino acid additions, substitutions or deletions in the amino acid sequence represented by SEQ ID NO: 54, or a heavy chain containing an amino acid sequence having identity of 80% or more with the amino acid sequence represented by SEQ ID NO: 54, and a light chain containing the amino acid sequence represented by SEQ ID NO: 55, a light chain containing an amino acid sequence containing one to several amino acid additions, substitutions or deletions in the amino acid sequence represented by SEQ ID NO: 55, or a light chain containing an amino acid sequence having identity of 80% or more with the amino acid sequence represented by SEQ ID NO: 55.

Another aspect of the anti-TMEM-180 antibody according to the present invention contains:

a heavy chain containing the amino acid sequence represented by SEQ ID NO: 62;

a heavy chain containing an amino acid sequence containing one to several amino acid additions, substitutions or deletions in the amino acid sequence represented by SEQ ID NO: 62; or a heavy chain containing an amino acid sequence having identity of 80% or more with the amino acid sequence represented by SEQ ID NO: 62.

The amino acid sequence represented by SEQ ID NO: 62 is an amino acid sequence of the heavy chain variable region of anti-TMEM-180 antibody clone 382.

Another aspect of the anti-TMEM-180 antibody according to the present invention contains:

a light chain containing the amino acid sequence represented by SEQ ID NO: 63;

a light chain containing an amino acid sequence containing one to several amino acid additions, substitutions or deletions in the amino acid sequence represented by SEQ ID NO: 63; or a light chain containing an amino acid sequence having identity of 80% or more with the amino acid sequence represented by SEQ ID NO: 63.

The amino acid sequence represented by SEQ ID NO: 63 is an amino acid sequence of the light chain variable region of anti-TMEM-180 antibody clone 382.

Another aspect of the anti-TMEM-180 antibody according to the present invention may contain a heavy chain containing the amino acid sequence represented by SEQ ID NO: 62, a heavy chain containing an amino acid sequence containing one to several amino acid additions, substitutions or deletions in the amino acid sequence represented by SEQ ID NO: 62, or a heavy chain containing an amino acid sequence having identity of 80% or more with the amino acid sequence represented by SEQ ID NO: 62, and a light chain containing the amino acid sequence represented by SEQ ID NO: 63, a light chain containing an amino acid sequence containing one to several amino acid additions, substitutions or deletions in the amino acid sequence represented by SEQ ID NO: 63, or a light chain containing an amino acid sequence having identity of 80% or more with the amino acid sequence represented by SEQ ID NO: 63.

Another aspect of the anti-TMEM-180 antibody according to the present invention contains:

a heavy chain containing the amino acid sequence represented by SEQ ID NO: 70;

a heavy chain containing an amino acid sequence containing one to several amino acid additions, substitutions or deletions in the amino acid sequence represented by SEQ ID NO: 70; or a heavy chain containing an amino acid sequence having identity of 80% or more with the amino acid sequence represented by SEQ ID NO: 70.

The amino acid sequence represented by SEQ ID NO: 70 is an amino acid sequence of the heavy chain variable region of anti-TMEM-180 antibody clone 1361.

Another aspect of the anti-TMEM-180 antibody according to the present invention contains:

a light chain containing the amino acid sequence represented by SEQ ID NO: 71;

a light chain containing an amino acid sequence containing one to several amino acid additions, substitutions or deletions in the amino acid sequence represented by SEQ ID NO: 71; or a light chain containing an amino acid sequence having identity of 80% or more with the amino acid sequence represented by SEQ ID NO: 71.

The amino acid sequence represented by SEQ ID NO: 71 is an amino acid sequence of the light chain variable region of anti-TMEM-180 antibody clone 1361.

Another aspect of the anti-TMEM-180 antibody according to the present invention may contain a heavy chain containing the amino acid sequence represented by SEQ ID NO: 70, a heavy chain containing an amino acid sequence containing one to several amino acid additions, substitutions or deletions in the amino acid sequence represented by SEQ ID NO: 70, or a heavy chain containing an amino acid sequence having identity of 80% or more with the amino acid sequence represented by SEQ ID NO: 70, and a light chain containing the amino acid sequence represented by SEQ ID NO: 71, a light chain containing an amino acid sequence containing one to several amino acid additions, substitutions or deletions in the amino acid sequence represented by SEQ ID NO: 71, or a light chain containing an amino acid sequence having identity of 80% or more with the amino acid sequence represented by SEQ ID NO: 71.

Another aspect of the anti-TMEM-180 antibody according to the present invention contains:

a heavy chain containing the amino acid sequence represented by SEQ ID NO: 78;

a heavy chain containing an amino acid sequence containing one to several amino acid additions, substitutions or deletions in the amino acid sequence represented by SEQ ID NO: 78; or a heavy chain containing an amino acid sequence having identity of 80% or more with the amino acid sequence represented by SEQ ID NO: 78.

The amino acid sequence represented by SEQ ID NO: 78 is an amino acid sequence of the heavy chain variable region of anti-TMEM-180 antibody clone 669.

Another aspect of the anti-TMEM-180 antibody according to the present invention contains:

a light chain containing the amino acid sequence represented by SEQ ID NO: 79;

a light chain containing an amino acid sequence containing one to several amino acid additions, substitutions or deletions in the amino acid sequence represented by SEQ ID NO: 79; or a light chain containing an amino acid sequence having identity of 80% or more with the amino acid sequence represented by SEQ ID NO: 79.

The amino acid sequence represented by SEQ ID NO: 79 is an amino acid sequence of the light chain variable region of anti-TMEM-180 antibody clone 669.

Another aspect of the anti-TMEM-180 antibody according to the present invention may contain a heavy chain containing the amino acid sequence represented by SEQ ID NO: 78, a heavy chain containing an amino acid sequence containing one to several amino acid additions, substitutions or deletions in the amino acid sequence represented by SEQ ID NO: 78, or a heavy chain containing an amino acid sequence having identity of 80% or more with the amino acid sequence represented by SEQ ID NO: 78, and a light chain containing the amino acid sequence represented by SEQ ID NO: 79, a light chain containing an amino acid sequence containing one to several amino acid additions, substitutions or deletions in the amino acid sequence represented by SEQ ID NO: 79, or a light chain containing an amino acid sequence having identity of 80% or more with the amino acid sequence represented by SEQ ID NO: 79.

Another aspect of the anti-TMEM-180 antibody according to the present invention contains:

a heavy chain containing the amino acid sequence represented by SEQ ID NO: 86;

a heavy chain containing an amino acid sequence containing one to several amino acid additions, substitutions or deletions in the amino acid sequence represented by SEQ ID NO: 86; or a heavy chain containing an amino acid sequence having identity of 80% or more with the amino acid sequence represented by SEQ ID NO: 86.

The amino acid sequence represented by SEQ ID NO: 86 is an amino acid sequence of the heavy chain variable region of anti-TMEM-180 antibody clone 699.

Another aspect of the anti-TMEM-180 antibody according to the present invention contains:

a light chain containing the amino acid sequence represented by SEQ ID NO: 87;

a light chain containing an amino acid sequence containing one to several amino acid additions, substitutions or deletions in the amino acid sequence represented by SEQ ID NO: 87; or a light chain containing an amino acid sequence having identity of 80% or more with the amino acid sequence represented by SEQ ID NO: 87.

The amino acid sequence represented by SEQ ID NO: 87 is an amino acid sequence of the light chain variable region of anti-TMEM-180 antibody clone 699.

Another aspect of the anti-TMEM-180 antibody according to the present invention may contain a heavy chain containing the amino acid sequence represented by SEQ ID NO: 86, a heavy chain containing an amino acid sequence containing one to several amino acid additions, substitutions or deletions in the amino acid sequence represented by SEQ ID NO: 86, or a heavy chain containing an amino acid sequence having identity of 80% or more with the amino acid sequence represented by SEQ ID NO: 86, and a light chain containing the amino acid sequence represented by SEQ ID NO: 87, a light chain containing an amino acid sequence containing one to several amino acid additions, substitutions or deletions in the amino acid sequence represented by SEQ ID NO: 87, or a light chain containing an amino acid sequence having identity of 80% or more with the amino acid sequence represented by SEQ ID NO: 87.

Another aspect of the anti-TMEM-180 antibody according to the present invention contains:

a heavy chain containing the amino acid sequence represented by SEQ ID NO: 94;

a heavy chain containing an amino acid sequence containing one to several amino acid additions, substitutions or deletions in the amino acid sequence represented by SEQ ID NO: 94; or a heavy chain containing an amino acid sequence having identity of 80% or more with the amino acid sequence represented by SEQ ID NO: 94.

The amino acid sequence represented by SEQ ID NO: 94 is an amino acid sequence of the heavy chain variable region of anti-TMEM-180 antibody clone 1052.

Another aspect of the anti-TMEM-180 antibody according to the present invention contains:

a light chain containing the amino acid sequence represented by SEQ ID NO: 95;

a light chain containing an amino acid sequence containing one to several amino acid additions, substitutions or deletions in the amino acid sequence represented by SEQ ID NO: 95; or a light chain containing an amino acid sequence having identity of 80% or more with the amino acid sequence represented by SEQ ID NO: 95.

The amino acid sequence represented by SEQ ID NO: 95 is an amino acid sequence of the light chain variable region of anti-TMEM-180 antibody clone 1052.

Another aspect of the anti-TMEM-180 antibody according to the present invention may contain a heavy chain containing the amino acid sequence represented by SEQ ID NO: 94, a heavy chain containing an amino acid sequence containing one to several amino acid additions, substitutions or deletions in the amino acid sequence represented by SEQ ID NO: 94, or a heavy chain containing an amino acid sequence having identity of 80% or more with the amino acid sequence represented by SEQ ID NO: 94, and a light chain containing the amino acid sequence represented by SEQ ID NO: 95, a light chain containing an amino acid sequence containing one to several amino acid additions, substitutions or deletions in the amino acid sequence represented by SEQ ID NO: 95, or a light chain containing an amino acid sequence having identity of 80% or more with the amino acid sequence represented by SEQ ID NO: 95.

Another aspect of the anti-TMEM-180 antibody according to the present invention contains:

a heavy chain containing the amino acid sequence represented by SEQ ID NO: 102;

a heavy chain containing an amino acid sequence containing one to several amino acid additions, substitutions or deletions in the amino acid sequence represented by SEQ ID NO: 102; or a heavy chain containing an amino acid sequence having identity of 80% or more with the amino acid sequence represented by SEQ ID NO: 102.

The amino acid sequence represented by SEQ ID NO: 102 is an amino acid sequence of the heavy chain variable region of anti-TMEM-180 antibody clone 1105.

Another aspect of the anti-TMEM-180 antibody according to the present invention contains:

a light chain containing the amino acid sequence represented by SEQ ID NO: 103;

a light chain containing an amino acid sequence containing one to several amino acid additions, substitutions or deletions in the amino acid sequence represented by SEQ ID NO: 103; or a light chain containing an amino acid sequence having identity of 80% or more with the amino acid sequence represented by SEQ ID NO: 103.

The amino acid sequence represented by SEQ ID NO: 103 is an amino acid sequence of the light chain variable region of anti-TMEM-180 antibody clone 1105.

Another aspect of the anti-TMEM-180 antibody according to the present invention may contain a heavy chain containing the amino acid sequence represented by SEQ ID NO: 102, a heavy chain containing an amino acid sequence containing one to several amino acid additions, substitutions or deletions in the amino acid sequence represented by SEQ ID NO: 102, or a heavy chain containing an amino acid sequence having identity of 80% or more with the amino acid sequence represented by SEQ ID NO: 102, and a light chain containing the amino acid sequence represented by SEQ ID NO: 103, a light chain containing an amino acid sequence containing one to several amino acid additions, substitutions or deletions in the amino acid sequence represented by SEQ ID NO: 103, or a light chain containing an amino acid sequence having identity of 80% or more with the amino acid sequence represented by SEQ ID NO: 103.

The anti-TMEM-180 antibody according to the present invention may be an antibody in which one or more N-linked oligosaccharides are bound to the Fc region, and fucose is not bound to N-acetylglucosamine on the reducing end of the N-linked oligosaccharide.

For example, two N-linked oligosaccharide binding sites are present in the Fc region of IgG antibody and a complex oligosaccharide is bound to this site. N-linked oligosaccharides refer to oligosaccharides bound to Asn of the sequence Asn-X-Ser/Thr that have the common structure of Man3GlcNAc2-Asn. These are classified into high mannose types, mixed types, complex types and the like depending on the type of oligosaccharide that binds to the two mannose (Man) on the non-reducing end.

Although fucose can be bound to N-acetylglucosamine (GlcNAc) on the reducing end of N-linked oligosaccharides, ADCC activity is known to increase considerably in the case fucose is not bound to this site in comparison with the case in which it is bound thereto. This finding is described in, for example, WO 2002/031140, and the disclosure thereof is incorporated in the present description in its entirety by reference.

Since the dosage of an antibody can be reduced in the case of using as a pharmaceutical due to this considerable increase in ADCC activity, in addition to making it possible to reduce adverse side effects, medical expenses can also be reduced.

One aspect of the anticancer drug according to the present invention contains, as an active ingredient thereof, an anti-TMEM-180 antibody having a substance having anticancer activity bound thereto, or an antigen-binding fragment thereof. In this aspect, the anti-TMEM-180 antibody or antigen-binding fragment thereof may also have anticancer activity per se or may only have the ability to bind to TMEM-180 without exhibiting anticancer activity.

In the present description, a "substance having anticancer activity" refers to a substance that causes at least one of a reduction (delay or interruption) of tumor size, inhibition of tumor metastasis, inhibition (delay or interruption) of tumor growth and alleviation of one or multiple symptoms associated with cancer. More specifically, examples thereof include, but are not limited to, toxins, anticancer drugs and radioisotopes.

Examples of toxins having anticancer activity include Pseudomonas exotoxin (PE) and cytotoxic fragments thereof (such as PE38), diphtheria toxin and lysin A. Since these toxins having anticancer activity demonstrate toxicity only in cells recognized by the anti-TMEM-180 antibody, namely cancer cells expressing TMEM-180, they offer the advantage of allowing the obtaining of specific effects without having a detrimental effect on surrounding cells.

Examples of anticancer drugs include low molecular weight compounds such as adriamycin, daunomycin, mitomycin, cisplatin, vincristine, epirubicin, methotrexate, 5-fluorouracil, aclacinomycin, nitrogen mustard, cyclophosphamide, bleomycin, daunorubicin, doxorubicin, vincristine, vinblastine, vindesine, tamoxifen or dexamethasone, and proteins such as cytokines that activate immunocompetent cells (such as human interleukin 2, human granulocyte-macrophage colony stimulating factor, human macrophage colony stimulating factor or human interleukin 12).

Examples of radioisotopes having anticancer activity include $^{32}P$, $^{14}C$, $^{125}I$, $^{3}H$, $^{131}I$, $^{211}At$ and $^{90}Y$.

Substances having anticancer activity are able to bind to the anti-TMEM-180 antibody either directly or through a linker according to a known method or method in compliance therewith. A substance having anticancer activity may be enclosed in a carrier such as a micelle or liposome and then bind the liposome to the anti-TMEM-180 antibody or an antigen-binding fragment thereof.

In the case the above-mentioned substance having anticancer activity is a protein or polypeptide, it may also be expressed in the form of a fusion protein formed of the substance having anticancer activity and an anti-TMEM-180 antibody by linking a nucleic acid encoding the anti-TMEM-180 antibody of the present invention to be subsequently described, encoding a substance having anticancer activity using DNA, and then inserting into a suitable expression vector.

In the present description, an "anticancer drug" refers to a pharmaceutical that causes at least one of a reduction (delay or interruption) of tumor size, inhibition of tumor metastasis, inhibition (delay or interruption) of tumor growth and alleviation of one or multiple symptoms associated with cancer.

The anticancer drug according to the present invention may also contain a pharmaceutically acceptable carrier or additive in addition to the active ingredient.

Examples of carriers and additives include, but are not limited to, pharmaceutically acceptable organic solvents such as water, saltwater, phosphate buffer, dextrose, glycerol and ethanol, as well as collagen, polyvinyl alcohol, polyvinylpyrrolidone, carboxyvinyl polymer, carboxymethyl cellulose sodium, sodium polyacrylate, sodium alginate, water-soluble dextran, sodium carboxymethyl starch, pectin, methyl cellulose, ethyl cellulose, xanthan gum, gum arabic, casein, agar, polyethylene glycol, diglycerin, glycerin, propylene glycol, Vaseline, paraffin, stearyl alcohol, stearic acid, human serum albumin, mannitol, sorbitol, lactose and surfactants.

The pharmaceutical composition of the present invention can adopt various forms, such as a liquid (e.g. injection preparation), dispersion, suspension, tablet, pill, powder or suppository. The pharmaceutical composition is preferably in the form of an injection preparation, and is preferably administered parenterally (such as intravenously, percutaneously, intraperitoneally or intramuscularly).

The pharmaceutical composition of the present invention is effective for treatment of cancer expressing TMEM-180. Examples of cancer expressing TMEM-180 include, but are not limited to, colon cancer and brain tumors.

The present invention also includes a method for treating cancer that involves administering the anticancer drug according to the present invention.

The dosage of the anticancer drug of the present invention is such that, for example, the dosage of the anti-TMEM-180 antibody or antigen-binding fragment thereof is 0.025 mg/kg to 50 mg/kg, preferably 0.1 mg/kg to 0 mg/kg, more preferably 0.1 mg/kg to 25 mg/kg, and even more preferably 0.1 mg/kg to 10 mg/kg or 0.1 mg/kg to 3 mg/kg, although not limited thereto.

The anticancer drug according to the present invention may be combined with other cancer therapy. Examples of other cancer therapy include administration of the above-mentioned other anticancer drugs, radiotherapy, surgery and cancer vaccine therapy.

In the present description, "cancer vaccine therapy" refers to a method for preventing or treating cancer that involves enhancing the immunity of a patient per se against cancer cells by administering a cancer antigen to the patient or stimulating patient-derived immune cells in vitro with a cancer antigen and then returning the cells to the patient. A peptide derived from a protein specifically expressed by cancer cells (cancer antigen-derived peptide) is used as an example of a cancer antigen used in cancer vaccine therapy.

A cancer antigen-derived peptide activates cytotoxic T lymphocytes (CTL) as a result of binding to human leukocyte antigen (HLA) on the surface of antigen-presenting cells such as dendritic cells and being presented on the CTL. Activated CTL then attack and eliminate cancer cells expressing the same antigen as the peptide. HLA molecules have a high degree of genetic diversity and demonstrate different genotypes depending on the individual. The sequences of those peptides having the possibility of being derived from a certain cancer antigen protein and binding to an HLA molecule of a specific genotype can be determined with known software or the like.

For example, those peptides derived from TMEM-180 protein and having the possibility of binding to HLA type A2 or HLA type A24 commonly found among Japanese were predicted as indicated below using HLA Peptide Binding Predictions published by the Bioinformatics and Molecular Analysis Section of the U.S. National Institutes of Health. In the tables, "Start position" indicates the location in the amino acid sequence set forth in SEQ ID NO: 17.

According to cancer vaccine therapy using these peptides, since CTL can be activated to attack cancer cells expressing TMEM-180 protein, cancer cells can be efficiently attacked by using in combination with the anticancer drug according to the present invention that targets TMEM-180, thereby making it possible to prevent or treat cancer. Cancer vaccine compositions containing these peptides can be prepared by a person with ordinary skill in the art in accordance with known methods.

TABLE 1

HLA molecule type: A_0201
Cutoff Score: 10 (Estimate of Half Time of Disassociation of a Molecule Containing This Subsequence)

| Rank | Start Position | Sequence | SEQ ID NO |
|---|---|---|---|
| 1 | 132 | CLYDgFLTLV | 104 |
| 2 | 33 | FLLYyVDTFV | 105 |
| 3 | 266 | FLWFvSMDLV | 106 |
| 4 | 322 | FLSLcRRWGV | 107 |
| 5 | 339 | FLLKIGLSLL | 108 |
| 6 | 376 | KLLTIVVTDL | 109 |
| 7 | 401 | ALLFgMVALV | 110 |
| 8 | 23 | ALFTtILHNV | 111 |
| 9 | 9 | WLLGIPTAVV | 112 |
| 10 | 482 | QLFTwSQFTL | 113 |
| 11 | 109 | LALSfLAFWV | 114 |
| 12 | 342 | KLGLsLLMLL | 115 |
| 13 | 2 | GLGQpQAWLL | 116 |
| 14 | 490 | TLHGrRLHMV | 117 |
| 15 | 60 | LLWNsLNDPL | 118 |
| 16 | 64 | SLNDpLFGWL | 119 |
| 17 | 139 | TLVDIHHHAL | 120 |
| 18 | 49 | KMAFwVGETV | 121 |
| 19 | 469 | YLLVIVPITC | 122 |
| 20 | 505 | NLSQaQTLDV | 123 |
| 21 | 377 | LLTLvVTDLV | 124 |
| 22 | 294 | LLSDhISLST | 125 |
| 23 | 348 | LMLLaGPDHL | 126 |
| 24 | 258 | RQLArHRNFL | 127 |

TABLE 1-continued

HLA molecule type: A_0201
Cutoff Score: 10 (Estimate of Half Time of Disassociation of a Molecule Containing This Subsequence)

| Rank | Start Position | Sequence | SEQ ID NO |
|---|---|---|---|
| 25 | 130 | CLCLyDGFLT | 128 |
| 26 | 425 | LLCFyTGHDL | 129 |
| 27 | 472 | VLVPiTCALL | 130 |
| 28 | 350 | LLAGpDHLSL | 131 |
| 29 | 70 | FGWLsDRQFL | 132 |
| 30 | 324 | SLCRrWGVYA | 133 |
| 31 | 481 | LQLFtWSQFT | 134 |
| 32 | 78 | FLSSqPRSGA | 135 |
| 33 | 204 | GLGFIGATQL | 136 |
| 34 | 124 | GLQFILCLCL | 137 |
| 35 | 153 | ALSAhDRTHL | 138 |
| 36 | 212 | QLLRrRVEAA | 139 |
| 37 | 17 | VVYGsLALFT | 140 |
| 38 | 470 | LLVLvPITCA | 141 |
| 39 | 402 | LLFGmVALVT | 142 |
| 40 | 271 | SMDLvQVFHC | 143 |
| 41 | 147 | ALLAdLALSA | 144 |
| 42 | 332 | YAVVrGLFLL | 145 |
| 43 | 45 | YKINkMAFWV | 146 |
| 44 | 282 | FNSNfFPLFL | 147 |
| 45 | 471 | LVLVpITCAL | 148 |
| 46 | 88 | GLSSrAVVLA | 149 |
| 47 | 417 | FAPLIGTWLL | 150 |

TABLE 2

HLA molecule type: A24
Cutoff Score: 10 (Estimate of Half Time of Disassociation of a Molecule Containing This Subsequence)

| Rank | Start Position | Sequence | SEQ ID NO |
|---|---|---|---|
| 1 | 311 | SYVApHLNNL | 151 |
| 2 | 331 | VYAVvRGLFL | 152 |
| 3 | 180 | SYAFwNKEDF | 153 |
| 4 | 265 | NFLWfVSMDL | 154 |
| 5 | 286 | FFPLfLEHLL | 155 |
| 6 | 338 | LFLLkLGLSL | 156 |
| 7 | 416 | TFAPILGTWL | 157 |
| 8 | 369 | VFTEgTCKLL | 158 |

TABLE 2-continued

HLA molecule type: A24
Cutoff Score: 10 (Estimate of Half Time of Disassociation of a Molecule Containing This Subsequence)

| Rank | Start Position | Sequence | SEQ ID NO |
|---|---|---|---|
| 9 | 285 | NFFPIFLEHL | 159 |
| 10 | 51 | AFWVgETVFL | 160 |
| 11 | 281 | HFNSnFFPLF | 161 |
| 12 | 376 | KLLTIVVTDL | 162 |
| 13 | 32 | VFLLyYVDTF | 163 |
| 14 | 258 | RQLArHRNFL | 164 |
| 15 | 336 | RGLFILKLGL | 165 |
| 16 | 503 | RQNLsQAQTL | 166 |
| 17 | 24 | LFTTiLHNVF | 167 |
| 18 | 64 | SLNDpLFGWL | 168 |
| 19 | 277 | VFHChFNSNF | 169 |
| 20 | 69 | LFGWISDRQF | 170 |

Nucleic Acid

The present invention also includes a nucleic acid that encodes the anti-TMEM-180 antibody, or antigen-binding fragment thereof, according to the present invention. The nucleic acid may be a naturally-occurring nucleic acid or artificial nucleic acid, and examples thereof include, but are not limited to, DNA, RNA and chimeras of DNA and RNA. The base sequence of a nucleic acid encoding the anti-TMEM-180 antibody or antigen-binding fragment thereof can be determined by a person with ordinary skill in the art in accordance with a known method or method complying therewith, and can also be prepared using a known method or method complying therewith.

Examples of nucleic acids encoding the anti-TMEM-180 antibody or antigen-binding fragment thereof according to the present invention include, but are not limited to, nucleic acid containing DNA encoding a heavy chain or light chain of anti-TMEM-180 antibody clone 98, nucleic acid containing DNA encoding any of heavy chain CDR1 to CDR3 and light chain CDR1 to CDR3 of anti-TMEM-180 antibody clone 98, nucleic acid containing DNA encoding a heavy chain or light chain of anti-TMEM-180 antibody clone 101, nucleic acid containing DNA encoding any of heavy chain CDR1 to CDR3 and light chain CDR1 to CDR3 of anti-TMEM-180 antibody clone 101, nucleic acid containing DNA encoding a heavy chain or light chain of anti-TMEM-180 antibody clone 212, and nucleic acid containing DNA encoding any of heavy chain CDR1 to CDR3 and light chain CDR1 to CDR3 of anti-TMEM-180 antibody clone 212.

Expression Vector

The expression vector according to the present invention contains nucleic acid encoding the anti-TMEM-180 antibody, or antigen-binding fragment thereof, according to the present invention. The expression vector can be suitably selected according to the host cells used, and examples thereof include plant virus vectors such as a plasmid, retrovirus vector, adenovirus vector, adeno-associated virus (AAV) vector, cauliflower mosaic virus vector or tobacco mosaic virus vector, as well as a cosmid, YAC or EBV-derived episomal vector. Nucleic acid encoding the anti-TMEM-180 antibody of the present invention can be inserted into these expression vectors using a known method (such as a method using a restriction enzyme).

The expression vector according to the present invention can further contain a promoter for regulating expression of antibody gene, a replication origin or a selection marker gene and the like. The promoter and replication origin can be suitably selected according to the types of host cells and vector.

Transformant

The transformant according to the present invention contains the vector according to the present invention. A transformant can be obtained by transfecting suitable host cells with the vector of the present invention. Examples of host cells that can be used include eukaryotic cells in the manner of mammalian cells (such as CHO cells, COS cells, myeloma cells, HeLa cells or Vero cells), insect cells, plant cells and fungal cells (such as cells of fungi belonging to the genii *Saccharomyces* and *Aspergillus*), and prokaryotic cells in the manner of *Escherichia coli* (*E. coli*) or *Bacillus subtilis* cells.

Antibody Production Method

Although there are no particular limitations on the method used to produce the anti-TMEM-180 antibody or antigen-binding fragment thereof according to the present invention, anti-TMEM-180 monoclonal antibody, for example, can be obtained by isolating antibody-producing cells from a non-human mammal immunized with TMEM-180 or a fragment thereof, fusing these cells with myeloma cells or the like to produce a hybridoma, and then purifying antibody produced by this hybridoma. In addition, anti-TMEM-180 polyclonal antibody can be obtained from the serum of an animal immunized with TMEM-180 or a fragment thereof.

In the case of producing the anti-TMEM-180 antibody according to the present invention by genetic recombination, for example, a suitable host is transformed with an expression vector containing the nucleic acid according to the present invention and this transformant is then cultured under suitable conditions to express antibody followed by isolating and purifying the antibody in accordance with known methods.

Examples of isolation and purification methods include an affinity column using Protein A or the like, other chromatography column, filter, ultrafiltration, salting out and dialysis, and these methods can also be suitably combined.

Human chimeric antibody and human CDR-grafted antibody can be produced by cloning antibody gene from mRNA of a hybridoma that produces antibody of an animal other than a human, and then linking this with a portion of a human antibody gene using genetic recombination technology.

For example, in the case of human chimeric antibody, cDNA is synthesized from the mRNA of a hybridoma producing mouse antibody using reverse transcriptase, and the heavy chain variable region (VH) and light chain variable region (LH) are cloned by PCR followed by analysis of the sequences thereof. Next, 5'-primers containing a leader sequence are produced starting with the antibody base sequence having the highest identity rate, and the region from the signal sequence to the 3'-end of the variable region is cloned by PCR from the above-mentioned cDNA by the 5'-primer and variable region 3'-primer. On the other hand, the constant regions of the heavy chain and light chain of human IgG1 are cloned, and the variable portions derived from mouse antibody and the constant regions derived from human antibody are linked for each of heavy chain and light chain by PCR using the overlapping hanging method and then amplified. The resulting DNA can then be inserted into a suitable vector followed by transformation thereof to obtain human chimeric antibody.

In the case of CDR-grafted antibody, the variable portion of mouse antibody used and the variable portion of human antibody demonstrating the highest homology are selected and cloned followed by modifying the base sequence of the CDR by site-directed mutagenesis using the megaprimer method. In cases in which antigen cannot be bound specifically following humanization of the amino acid sequence that composes the framework region, the amino acids of a portion of the framework region may be converted from human amino acids to rat amino acids.

CDRs comprising an amino acid sequence having one or two amino acid deletions, substitutions or additions in the original sequence, and CDRs comprising an amino acid sequence having identity of X % or more with the original sequence can be produced using a known method such as site-specific mutagenesis, random mutagenesis, chain shuffling or CDR walking.

According to these methods, CDRs having a higher degree of affinity maturation are well known among persons with ordinary skill in the art to be obtained by presenting antibodies or antibody fragments having various mutations in the CDR thereof on a phage surface by phage display followed by screening using antigen (see, for example, Wu, et al., PNAS, 95, 6037-6042 (1998); Schier, R., et al., J. Mol. Biol., 263, 551-567 (1996); Schier, R., et al., J. Mol. Biol., 255, 28-43 (1996); Yang, W. P., et al., J. Mol. Biol., 254, 392-403 (1995)). The present invention also includes an antibody containing the CDR subjected to affinity maturation using such methods.

Examples of other antibody production methods include the Adlib method, by which an antibody-producing line is acquired from a chicken B cell-derived DT40 cell line treated with trichostatin A (Seo, H., et al., Nat. Biotechnol., 6, 731-736, 2002), and a method involving immunizing KM mice introduced with human antibody gene following destruction of mouse antibody gene to produce human antibody (Itoh, K., et al., Jpn. J. Cancer Res., 92, 1313-1321, 2001; Koide, A., et al., J. Mol. Biol., 284, 1141-1151, 1998), and these methods can be applied to production of the antibody according to the present invention.

An antigen-binding fragment of the anti-TMEM-180 antibody according to the present invention may be expressed according to the above-mentioned methods using DNA encoding the fragment, or by fragmenting the full-length antibody by treating with an enzyme such as papain or pepsin.

The anti-TMEM-180 antibody according to the present invention can vary in terms of amino acid sequence, molecular weight, isoelectric point, presence or absence of oligosaccharide or form and the like according to the production method or purification method. However, the resulting antibody is included in the present invention provided it has a function that is equivalent to that of the antibody of the present invention. For example, in the case the antibody of the present invention has been expressed in E. coli or other prokaryotic cells, a methionine residue is added to the N-terminal of the amino acid sequence of the original antibody. This antibody is also included in the present invention.

In the case the anti-TMEM-180 antibody according to the present invention is an antibody having an N-linked oligosaccharide in which fucose is not bound to N-acetylglucosamine of the reducing end, the antibody can be produced in accordance with a known method or method complying therewith. Methods for producing this antibody are described in, for example, WO 2002/031140 and Japanese Patent Application Publication No. 2009-225781, and the disclosure thereof is incorporated in the present description in its entirety by reference.

More specifically, the anti-TMEM-180 antibody according to the present invention can be obtained, for example, by transforming cells deficient in or lacking enzyme activity involved in synthesis of GDP-fucose or α-1,6-fucosyl transferase activity using a vector containing DNA encoding the anti-TMEM-180 antibody according to the present invention, and then culturing the resulting transformant followed by purifying the target anti-TMEM-180 antibody.

Examples of enzymes involved in synthesis of GDP-fucose include GDP-mannose 4,6-dehydratase (GMP), GDP-keto-6-deoxymannose 3,5-epimerase, 4-reductase (Fx) and GDP-beta-L-fucose pyrophosphorylase (GFPP).

Here, although there are no particular limitations thereon, the cells are preferably mammalian cells, and for example, CHO cells deficient in or lacking the above-mentioned enzyme activity can be used.

Although there are cases in which an antibody composition obtained according to the above-mentioned method may contain antibody in which fucose is bound to N-acetylglucosamine on the reducing end, the proportion of antibody in which fucose is bound in this manner is 20% by weight or less, preferably 10% by weight or less, more preferably 5% by weight or less, and most preferably 3% by weight or less of total antibody weight.

In addition, antibody having an N-linked oligosaccharide in which fucose is not bound to N-acetylglucosamine on the reducing end can be obtained by introducing a vector containing DNA encoding the anti-TMEM-180 antibody according to the present invention into insect eggs, allowing the eggs to hatch and grow into insects, and then cross-breeding the insects as necessary to produce transgenic insects followed by extracting the anti-TMEM-180 antibody from the transgenic insects or secretions thereof. Silkworms can be used as the transgenic insects and in this case, antibody can be extracted from the cocoon.

Although there are also cases in which an antibody composition obtained according to this method may contain antibody in which fucose is bound to N-acetylglucosamine of the reducing end, the proportion antibody in which fucose is bound in this manner is 20% by weight or less, preferably 10% by weight or less, more preferably 5% by weight or less, and most preferably 3% by weight or less of total antibody weight.

Activity of Antibody of Present Invention

The mechanism of the efficacy of an antibody drug is based on two types of biological activity associated with the antibody. The first is binding activity specific to a target antigen in which the function of a target antigen molecule is neutralized as a result of binding thereto. Neutralization of the function of a target antigen molecule is demonstrated via the Fab region.

The other type of biological activity is antibody biological activity referred to as effector activity. Effector activity is demonstrated via the antibody Fc region in the form of, for example, antibody-dependent cellular cytotoxicity (ADCC), complement-dependent cytotoxicity (CDC) or direction induction of apoptosis.

Activity of the anti-TMEM-180 antibody according to the present invention can be measured using the methods indicated below.

(1) Binding Activity

Antibody binding activity can be measured using a known method such as enzyme-linked immunosorbent assay (ELISA), enzyme immunoassay (EIA), radioimmunoassay (RIA), fluorescent antibody technique or FACS.

(2) ADCC Activity

ADCC activity refers to activity that causes damage to a target cell when the antibody of the present invention has bound to an antigen on the surface of a target cell and an Fcγ receptor-retaining cell (effector cell) binds to the Fc moiety thereof via an Fcγ receptor.

ADCC activity can be determined by mixing a target cell expressing TMEM-180, an effector cell and the antibody of the present invention and measuring the degree of ADCC. Examples of effector cells that can be used include mouse spleen cells and monocytes isolated from human peripheral blood or bone marrow.

TMEM-180-positive colon cancer mucosal cells, for example, can be used as target cells. The target cells are preliminarily labeled with a label such as $^{51}Cr$ and the antibody of the present invention is then added thereto and incubated, followed by adding a suitable ratio of effector cells to the target cells and incubating. Following incubation, the supernatant is collected and ADCC activity can be measured by counting the level of the above-mentioned label in the supernatant.

(3) CDC Activity

CDC activity refers to cytotoxic activity involving complement.

CDC activity can be measured by using complement instead of effector cells in a test of ADCC activity.

(4) Tumor Growth Inhibitory Activity

Tumor growth inhibitory activity can be measured using tumor model animals. For example, the antibody of the present invention is administered after having transplanted a tumor beneath the skin of a mouse. Tumor growth inhibitory effect can be measured by comparing the volume of tumor tissue between a non-dose group and dose group.

Furthermore, the tumor growth inhibitory activity of the present invention may be that occurring as a result of inhibiting the growth of individual cells or that occurring as a result of inducting cell death.

Testing Method and Testing Kit

As was previously described, TMEM-180 is only expressed in specific cancer cells. Thus, the cancer testing method according to the present invention includes a step of measuring the amount of TMEM-180 in a sample collected from a subject.

In the present description, the sample collected from a subject can be any sample suitable for cancer testing, and can be suitably determined and collected according to the type of cancer by a person with ordinary skill in the art. Examples of samples include, but are not limited to, serum, plasma, whole blood, urine, stool, coelomic fluid and tissue. In the case of testing for colon cancer, the sample may be tissue collected from the subject with a colon endoscope or the like, or mucosal cells contained in washings following colonoscopy.

Carcinoembryonic antigen (CEA) has conventionally been widely used as a marker for colon cancer. Although plasma CEA levels decrease due to treatment such as surgical excision of the cancer, since they increase again accompanying recurrence or metastasis, measurement of CEA level is used to monitor progress following treatment. In cases in which CEA level has been observed to rise again, follow-up examinations involving abdominal ultrasonography and abdominal CT are required. However, since only 45% of colon cancer patients demonstrate an increase in CEA level, patients having cancer of a type that does not exhibit an increase in CEA level must undergo several rounds of follow-up examinations in order to monitor their progress.

In contrast, plasma TMEM-180 levels increase even in patients not exhibiting increases in CEA levels and are lower after surgery than before surgery as is indicated in the examples to be subsequently described. Moreover, plasma TMEM-180 levels are also observed to temporarily decrease after surgery and then exhibit a significant increase at the time of recurrence. This increase has been shown to be observed particularly in patients who do not exhibit an increase in CEA levels at the time of recurrence. Thus, this is considered to be an extremely useful marker capable of being used in a wide range of cancer patients.

The cancer testing method according to the present invention may be used for cancer diagnosis or may be used to confirm recurrence or metastasis when monitoring progress following surgery or other treatment.

In the present description, the "step for measuring the amount of TMEM-180 in a sample" includes not only a step of quantifying the amount of TMEM-180, but also includes a step of detecting for the presence or absence of TMEM-180, a step of determining a change in the amount of TMEM-180, and a step of comparing with the amount of TMEM-180 present in another sample.

The amount of TMEM-180 in a sample can be measured using any method used to measure the amount of a specific protein in a sample, and examples thereof include, but are not limited to, immunoassay (including agglutination and turbidimetry), western blotting and surface plasmon resonance (SPR). Among these, immunoassay using an anti-TMEM-180 antibody or an antigen-binding fragment thereof is both easy and useful.

Since TMEM-180 is a membrane protein, the amount thereof may be measured after having solubilized the membrane protein by treating with a commercially available cell lysis buffer, nonionic surfactant, membrane protein solubilizing reagent or the like.

Immunoassay uses an anti-TMEM-180 antibody labeled to allow subsequent detection and/or an antibody to the anti-TMEM-180 antibody labeled to allow subsequent detection (secondary antibody). Antibody labeling methods are classified into enzyme immunoassay (EIA or ELISA), radioimmunoassay (RIA), fluorescent immunoassay (FIA), fluorescence polarization immunoassay (FPIA), chemiluminescence immunoassay (CLIA), fluorescence enzyme immunoassay (FLEIA), chemiluminescence enzyme immunoassay (CLEIA), electrochemiluminescence immunoassay (ECLIA) and the like, and any of these methods can be used in the method of the present invention.

An antibody labeled with an enzyme such as peroxidase or alkaline phosphatase is used in the ELISA method, an antibody labeled with a radioactive substance such as $^{125}$I, $^{131}$I, $^{35}$S or $^{3}$H is used in the RIA method, an antibody labeled with a fluorescent substance such as fluorescein isocyanate, rhodamine, dansyl chloride, phycoerythrin, tetramethylrhodamine isothiocyanate or near-infrared fluorescent material is used in the FPIA method, and an antibody labeled with a luminescent substance such as luciferase, luciferin or aequorin is used in the CLIA method. Antibodies labeled with other substances in the manner of nanoparticles such as metal colloids or quantum dots can also be detected.

In addition, when using an immunoassay, the anti-TMEM-180 antibody can also be detected by labeling with biotin and then binding with avidin or streptavidin labeled with an enzyme and the like.

Among these immunoassays, the ELISA method using an enzyme label enables antigen to be measured both easily and quickly.

The ELISA method includes a competitive method and a sandwich method. In the competitive method, an anti-TMEM-180 antibody or an antigen-binding fragment thereof is immobilized on a microplate or other solid-phase support, and a sample and enzyme-labeled TMEM-180 are added thereto followed by allowing an antigen-antibody reaction to occur. After having washed the support, the antigen-antibody complex is allowed to react with the enzyme substrate resulting in the generation of color followed by measurement of optical absorbance. Since coloring is lighter if a large amount of TMEM-180 is contained in the sample and darker if only a small amount thereof is contained in the sample, the amount of TMEM-180 can be determined using a calibration curve.

In the sandwich method, an anti-TMEM-180 antibody or an antigen-binding fragment thereof is immobilized on a solid-phase support, and after adding a sample and allowing to react, an enzyme-labeled anti-TMEM-180 antibody that recognizes a different epitope is further added and allowed to react. After washing, the resulting complex is allowed to react with the enzyme substrate to generate color followed by measurement of optical absorbance to determine the amount of TMEM-180. In the sandwich method, after having reacted TMEM-180 in a sample with antibody immobilized on a solid-phase support, an unlabeled antibody (primary antibody) may be added followed by enzyme-labeling an antibody to this unlabeled antibody (secondary antibody) and further adding thereto.

Examples of enzyme substrates that can be used in the case the enzyme is peroxidase include 3,3'-diaminobenzidine (DAB), 3,3',5,5'-tetramethylbenzidine (TMB) and o-phenylenediamine (OPD), while examples of substrates in the case the enzyme is alkaline phosphatase include p-nitropheny phosphate (NPP).

Alternatively, TMEM-180 antigen in a sample may be immobilized directly on a microtiter plate or other solid-phase support, and after carrying out the required blocking, an unlabeled antibody (primary antibody) is added followed by enzyme-labeling and further adding an antibody to this unlabeled antibody (secondary antibody).

In the present description, there are no particular limitations on the "solid-phase support" provided it is a support that is capable of immobilizing antibody thereon, and examples thereof include microtiter plates made of glass, metal, resin or the like, substrates, beads, nitrocellulose membranes, nylon membranes and PVDF membranes, and a target substance can be immobilized on these solid-phase supports in accordance with known methods.

In addition, among these immunoassays, agglutination methods are preferable since they enable a trace amount of protein to be detected easily. Examples of agglutination methods include latex agglutination that uses latex particles bound to antibody.

When the anti-TMEM-180 antibody is allowed to bind to the latex particles and then mixed with a suitably treated sample, antibody-bound latex particles end up agglutinating if TMEM-180 is present. Therefore, antigen concentration can be determined by quantifying the amount of agglomerate by irradiating the sample with near-infrared light and measuring optical absorbance (turbidimetry) or measuring scattered light (nephelometry).

The previously described anti-TMEM-180 antibody, or antigen-binding fragment thereof, having the previously listed CDR sequences may be used for the anti-TMEM-180 antibody or antigen-binding fragment thereof.

The cancer testing kit according to the present invention is a kit for testing for cancer using the above-mentioned testing method, and contains an anti-TMEM-180 antibody or antigen-binding fragment thereof. In addition to the anti-TMEM-180 antibody or antigen-binding fragment thereof, the cancer testing kit according to the present invention may also contain reagents and apparatuses required to measure the amount of TMEM-180 in a sample by immunoassay.

One aspect of a testing kit is that for measuring TMEM-180 according to the sandwich method, and contains a microtiter plate, anti-TMEM-180 capture antibody or antigen-binding fragment thereof, an anti-TMEM-180 antibody or antigen-binding fragment thereof labeled with alkaline phosphatase or peroxidase, and alkaline phosphatase substrate (such as NPP) or peroxidase substrate (such as DAB, TMB or OPD).

The capture antibody and labeled antibody recognize different epitopes.

In this type of kit, the capture antibody is first immobilized on a microtiter plate followed by suitably diluting a sample and adding thereto, incubating, removing the sample and washing. Next, the labeled antibody is added followed by incubating and adding substrate to develop color. The amount of TMEM-180 can be determined by measuring the degree of coloring using a microtiter plate reader and the like.

Another aspect of the testing kit is for measuring TMEM-180 according to the sandwich method using secondary antibody, and contains a microtiter plate, anti-TMEM-180 capture antibody, primary antibody in the form of anti-TMEM-180 antibody, secondary antibody in the form of alkaline phosphatase- or peroxidase-labeled anti-TMEM-180 antibody, and alkaline phosphatase substrate (such as NPP) or peroxidase substrate (such as DAB, TMB or OPD).

The capture antibody and primary antibody recognize different epitopes.

In this type of kit, the capture antibody is first immobilized on a microtiter plate followed by suitably diluting a sample and adding thereto, incubating, removing the sample and washing. Continuing, the primary antibody is added followed by incubating and washing, after which the enzyme-labeled secondary antibody is added and incubated followed by adding the substrate to develop color. The amount of TMEM-180 can be determined by measuring the degree of coloring using a microtiter plate reader and the like. The use of secondary antibody makes it possible to amplify the reaction and enhance detection sensitivity.

The testing kit may further contain a required buffer solution, enzyme reaction stopping solution or microplate reader and the like.

The labeled antibody is not limited to an enzyme-labeled antibody, but rather may also be an antibody labeled with a radioactive substance (such as $^{25}$I, $^{131}$I, $^{35}$S or $^{3}$H), fluorescent substance (such as fluorescein isocyanate, rhodamine, dansyl chloride, phycoerythrin, tetramethylrhodamine isothiocyanate or near-infrared fluorescent material), luminescent substance (such as luciferase, luciferin or aequorin), nanoparticles (such as metal colloids or quantum dots) or the like. In addition, biotinated antibody can be used for the labeled antibody and labeled avidin or streptavidin can be added to the kit.

Still another aspect of the testing kit is a testing kit used to measure the amount of TMEM-180 by latex agglutination. This kit contains anti-TMEM-180 antibody-sensitized latex, and agglomerates are quantified by an optical method after mixing with a sample and an anti-TMEM-180 antibody. An agglutination reaction plate for visualizing the agglutination reaction is also preferably contained in the kit.

Disclosures of all patent documents and non-patent documents cited in the present description are incorporated in the present description in their entirety by reference.

EXAMPLES

Although the following provides a detailed explanation of the present invention based on examples thereof, the present invention is not limited thereto. A person with ordinary skill in the art would be able to modify the present invention in various forms without deviating from the significance of the present invention, and all such modifications are included within the scope of the present invention.

1. Identification of TMEM-180 Molecule

1) DNA Microarray Analysis

10 μg aliquots of mRNA were used that were respectively derived from five types of human colon cancer cell lines (HT29, SW480, LOVO, HCT116 and DLD-1) and two types of free colon cells derived from healthy human subjects. Biotin-labeled cRNA was synthesized after obtaining double-stranded cDNA from RNA in accordance with the instructions of the manufacturer (Affymetrix, Inc.). Following fragmentation, the fragments were hybridized with the GeneChip Human Genome U133 Plus 2.0 Array (Affymetrix, Inc.). The hybrids were scanned using the GeneChip Scanner 3000 7G (Affymetrix, Inc.). CEL data was acquired and then subjected to statistical processing to calculate the signal value of each sample. TMEM-180 was selected as a colon cancer cell-specific surface marker for which expression was observed in the five types of human colon cancer cell lines but not observed in the two types of healthy subject colon cells (FIG. 1A).

2) Quantitative PCR

Colon cancer cell tissue sample cDNA (Clontech Laboratories, Inc.) was analyzed with the ABI 7500Fast analyzer (Applied Biosystems) using adjacent normal colon tissue as a negative control for the colon cancer surgical specimens of five patients. 10 μL of 2X TaqMan Fast Universal PCR Master Mix (Applied Biosystems) and 1 μL of 20X TaqMan Gene Expression Assay (Applied Biosystems) were used in 20 μL of reaction solution. In addition, quantitative PCR was carried out with a fast run under conditions of 40 cycles of AmpliTaq Gold Enzyme activation at 95° C. and 20 seconds per cycle, denaturation at 95° C. for 3 seconds, and annealing/extending for 30 seconds at 62° C. The results were analyzed with 7500 Fast System SDS Software Version 1.3. The results of calculating the ratio of the amount of RNA in colon cancer tissue to the amount of RNA in normal tissue are shown in FIG. 1B for each case. In each of the cases, TMEM-180 was confirmed to be strongly expressed in colon cancer tissue as compared with normal colon tissue.

3) In Situ Hybridization

A colon cancer tissue paraffin section (Genostaff Co., Ltd.) was subjected to dewaxing treatment with xylene and then hydrated with ethanol and PBS. The section was then fixed for 15 minutes with 4% para-formaldehyde in PBS. After treating with PBS containing 7 μg/mL of Proteinase K (F. Hoffmann-La Roche Ltd.), the section was again fixed with 4% para-formaldehyde in PBS. The section was acetylated with 0.1 M Tris-HCl (pH 8.0) containing 0.25% acetic anhydride. After washing with PBS, the section was dehydrated with ethanol. The section was then subjected to a hybridization reaction with 300 ng/mL of an RNA probe of digoxigenin-labeled TMEM-180 (475 bp sequence from the 1314th nucleotide to the 1789th nucleotide of GeneBank Accession No. NM_024789, Genostaff Co., Ltd.) for 16 hours at 60° C. After washing, the section was treated with 50 μg/mL of RNaseA, 10 mM Tris-HCl (pH 8.0), 0.1 M NaCl and 1 mM EDTA. After washing again, the section was allowed to react using 0.5% blocking reaction solution (F. Hoffmann-La Roche Ltd.) followed by reacting for 1 hour in blocking reaction solution containing 20% heat-treated sheep serum (Sigma-Aldrich Co. LLC.). AP-labeled anti-DIG antibody (F. Hoffmann-La Roche Ltd.) was then added and allowed to react for 2 hours at room temperature. After washing, color was developed in NBT/NCIP solution (F. Hoffmann-La Roche Ltd.). The results of enclosure and microscopic observation are shown in FIGS. 1C and 1D. TMEM-180 was confirmed to be positive in all five types of the colon cancer tissue and negative in normal colon mucosa.

2. Expression Analysis of TMEM-180 in Normal Tissue

A search was made for TMEM-180 using the public database, PaxDB, in the form of a comprehensive absolute protein abundance database (pax-db.org/#!home, which measures the expression level of each protein by analyzing unique peptides by LC/MS/MS) to investigate measured values in each type of normal tissue. Other than TMEM-180, expression of the following molecules was also investigated as controls.

β-actin (βACT) (housekeeping molecule)
Glyceraldehyde 3-phosphate dehydrogenase (GAPDH) (housekeeping molecule)
Epidermal growth factor receptor (EGFR) (target molecule of antibody drug)
HER2 (target molecule of antibody drug)
Carcinoembryonic antigen (CEA) (typical tumor marker molecule)

Figure 2B:
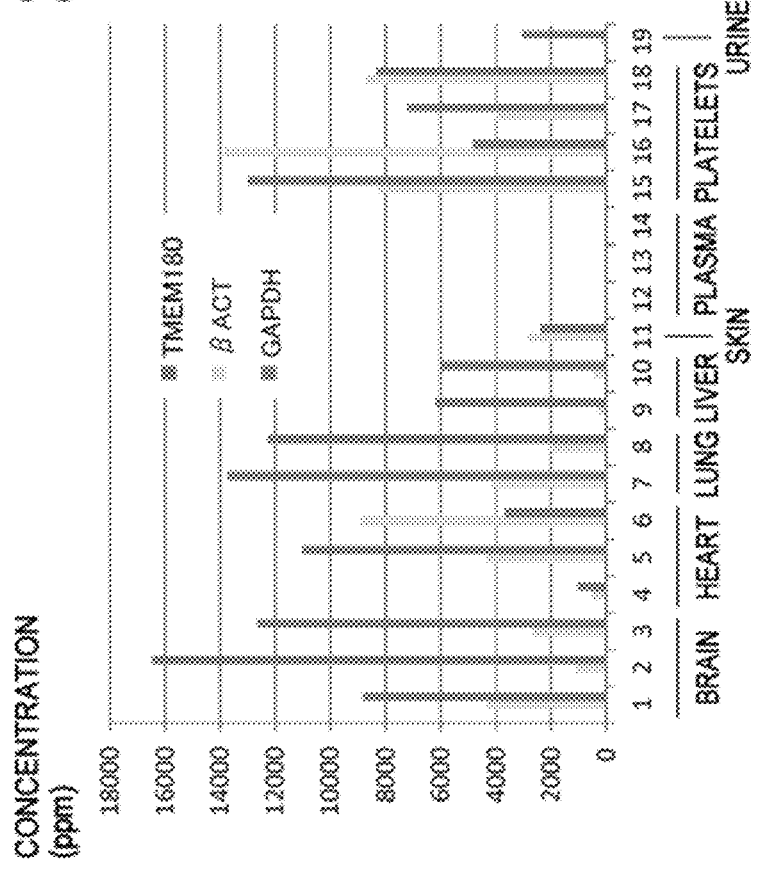
FIG. 2B indicates the results of investigating expression of trace amounts of TMEM-180 for molecules targeted by TMEM-180 and conventional anticancer drugs using the same method as in FIG. 2A.

The results of entering the data into an Excel (2010, Microsoft Corporation) file and generating graphs are shown in FIG. 2. Although TMEM-180 is rarely expressed normally (FIG. 2A) and was observed to be only slightly expressed in platelets when sensitivity was increased, expression was much lower than the conventional antibody drug target molecules of EGFR and HER2 (FIG. 2B), thereby confirming that TMEM-180 is specifically expressed in cancer tissue.

3. Antibody Production and FACS on Various Types of Cancer Cells

1) Antigen Production

PCR Reaction

PCT amplification was carried out on a tag sequence incorporated in pET21b using the primers indicated below.

PCR enzyme used: PRIMESTAR HS DNA polymerase (Takara Bio Inc., R010A)

Primer sequences for producing immunizing antigen 1:

(i)
(SEQ ID NO: 18)
cagacctgcacctgaacgtggttgagagctgaggaattgacggtcactg agggactgtaatgctgcacttcgc (ii)
(SEQ ID NO: 19)
caaccacgttcaggtgcaggtctgtcttcacgtgctgttgtactggctc gtgttcaagagttcaaactggaggacctg (iii)
(SEQ ID NO: 20)
gagatatacatatgtcggaggtgactcgtagtc (iv)
(SEQ ID NO: 21)
tggtgctcgagaataggctgaacatcaaatg Primer sequences for producing immunizing antigen 2:

(i)
(SEQ ID NO: 22)
gcgaagtgcagcattacagtccgatcatctgagtctgctgtgcctctt cattgc (ii)
(SEQ ID NO: 23)
caggtcctccagtttgaactcagaagctgcttgcttacgatgattcag caccaggtcctcgtctac (iii)
(SEQ ID NO: 24)
gagatatacatatgtcggaggtgactcgtagtc (iv)
(SEQ ID NO: 25)
tggtgctcgagaataggctgaacatcaaatg Restriction Enzyme Treatment NdeI (Takara Bio Inc.) and XhoI (Takara Bio Inc.) were reacted for 2 hours with expression vector pET21b and the PCR products in accordance with the manufacturer's protocol, and carrying out 1% agarose gel electrophoresis, the products were purified using the Promega Wizard SV Gal and PCR Clean-up System kit.

Ligation Reaction

A vector and insert were reacted for 30 minutes using Ligation High (Toyobo Co., Ltd.).

Transformation

Transformation was carried out using Competent High DH5α (Toyobo Co., Ltd.) followed by culturing in plates containing LB medium (50 μg/mL).

Gene Confirmation

The plasmid was extracted from the transformed E. coli and the sequence was analyzed to confirm the target sequence.

Transformation (E. coli)

BL21(DE3) was transformed with the plasmid inserted with the target sequence.

Culturing

The transformed E. coli was inoculated into 10 mL of LB medium and cultured for 16 hours at 37° C. followed by transferring the medium to 1 L of LB medium and culturing at 37° C. IPTG was added to a final concentration of 1 mM when the OD value at 600 nm reached 0.6 followed by additionally culturing for 4 hours.

Purification

Sediment of the disrupted E. coli was suspended in 50 mM Tris-HCl, 500 mM NaCl and 6 M GdnHCl followed by recovering supernatant from the sample after shaking for 16 hours and purifying with a nickel column.

Refolding

Since the target antigen had been denatured as a result of dissolving with 6 M GdnHCl, refolding (protein unwinding) was carried out by dialysis.

Refolding was carried out according to the following steps under the conditions indicated below.

(1) 50 mM Tris-HCl, pH 8.5, 500 mM NaCl, 1 mM EDTA, 1 mM DTT, 3 M GdnHCl, 6 hours
(2) 50 mM Tris-HCl, pH 8.5, 500 mM NaCl, 1 mM EDTA, 1 mM DTT, 2 M GdnHCl, 6 hours
(3) 50 mM Tris-HCl, pH 8.5, 500 mM NaCl, 1 mM EDTA, 1 mM DTT, 1 M GdnHCl, 12 hours
(4) 50 mM Tris-HCl, pH 8.5, 500 mM NaCl, 1 mM EDTA, 1 mM DTT, 0.5 M GdnHCl, 12 hours
(5) 50 mM Tris-HCl, pH 8.5, 150 mM NaCl, 50 mM L-Arg, 6 hours
(6) 50 mM Tris-HCl, pH 8.5, 150 mM NaCl, 50 mM L-Arg, 6 hours The dialysis solution of the above-mentioned sample was replaced with 50 mM phosphate buffer (pH 8.0) and 500 mM NaCl using an ultrafiltration membrane (Amicon-Ultra 10K).

Measurement of CD

Helix content was confirmed to approach the theoretical value using a circular dichroic disperser (JASCO Corporation, J-725) in order to confirm whether the refolded immunizing antigen retained its steric structure.

2) Antibody Production

An emulsion prepared by mixing immunizing antigen 1 or immunizing antigen 2, diluted to 100 μg/mL with PBS, with Freund's Complete Adjuvant in a 1:1 ratio was administered in 100 μL aliquots at both sides of the base of the caudal vein in rats (Japan SLC, Inc., Wistar, females, age 6 to 8 weeks). Blood was collected from the caudal vein at 12 to 13 days after immunization and serum antibody titers were evaluated by ELISA using the prepared antiserum and immunizing antigen for the solid phase or by flow cytometry using DLD-1 cells and K562 cells to select individuals for use in cell fusion. Iliac lymph nodes, inguinal lymph nodes, axillary lymph nodes and popliteal lymph nodes were dissected from individuals selected at 14 days after immunization, and lymph node cells and mouse myeloma cells p3X63 were fused according to the PEG method. Culture supernatant was recovered 10 to 14 days after fusion and antibody-producing hybridoma cells that were positive for DLD-1 cells and negative for K562 cells were selected by flow cytometry. The selected antibody-producing hybridoma cells were single-cloned and established by limiting dilution. Antibody isotypes were identified by isotype-specific ELISA (Bethyl Laboratories).

The single-cloned clones were clone 98, clone 101, clone 212 (which are IgM antibodies), clone 129, clone 382, clone 1361 (which are IgG antibodies), clone 669, clone 699, clone 1052 and clone 1105 (which are IgM antibodies).

3) Flow Cytometry

Cancer cells targeted for measurement were cultured in medium and then added to a V-bottom 96-well plate (Corning Incorporated) to a concentration of $1 \times 10^5$ cells/well. The plate was centrifuged for 3 minutes at 440×g and 4° C. followed by removing the supernatant, adding antibody-producing hybridoma culture supernatant or antibody solution to the cell pellet at 50 μL/well and suspending therein. After allowing to react for 45 minutes on ice, the plate was washed three times with a mixture of 0.1% BSA, 2 mM EDTA and PBS at 200 μL/well. The supernatant was removed and secondary antibody was added to the cell pellet at 50 μL/well followed by suspending the cells therein. ALEXAFLUOR 647 goat anti-rat IgG (H-L) (Life Technologies Corporation) was used for the secondary antibody after diluting 400-fold with a mixture of 0.1% BSA, 2 mM EDTA and PBS. After allowing to react for 45 minutes on ice, the plate was washed three times with a mixture of 0.1% BSA, 2 mM EDTA and PBS at 200 μL/well. After removing the supernatant, 50 ng/mL of propidium iodide, 0.1% BSA, 2 mM EDTA and PBS were added to the cell pellet at 250 μL/well followed by suspending therein. The cells stained in this manner were measured using a flow cytometer such as the Guava easyCyte 8HT (Merck Millipore Corporation) followed by analysis of the resulting data using FlowJO (Tomy Digital Biology Co., Ltd.). FACS analysis was carried out using colon cancer, brain tumor and hematologic cancer.

Figure 3:
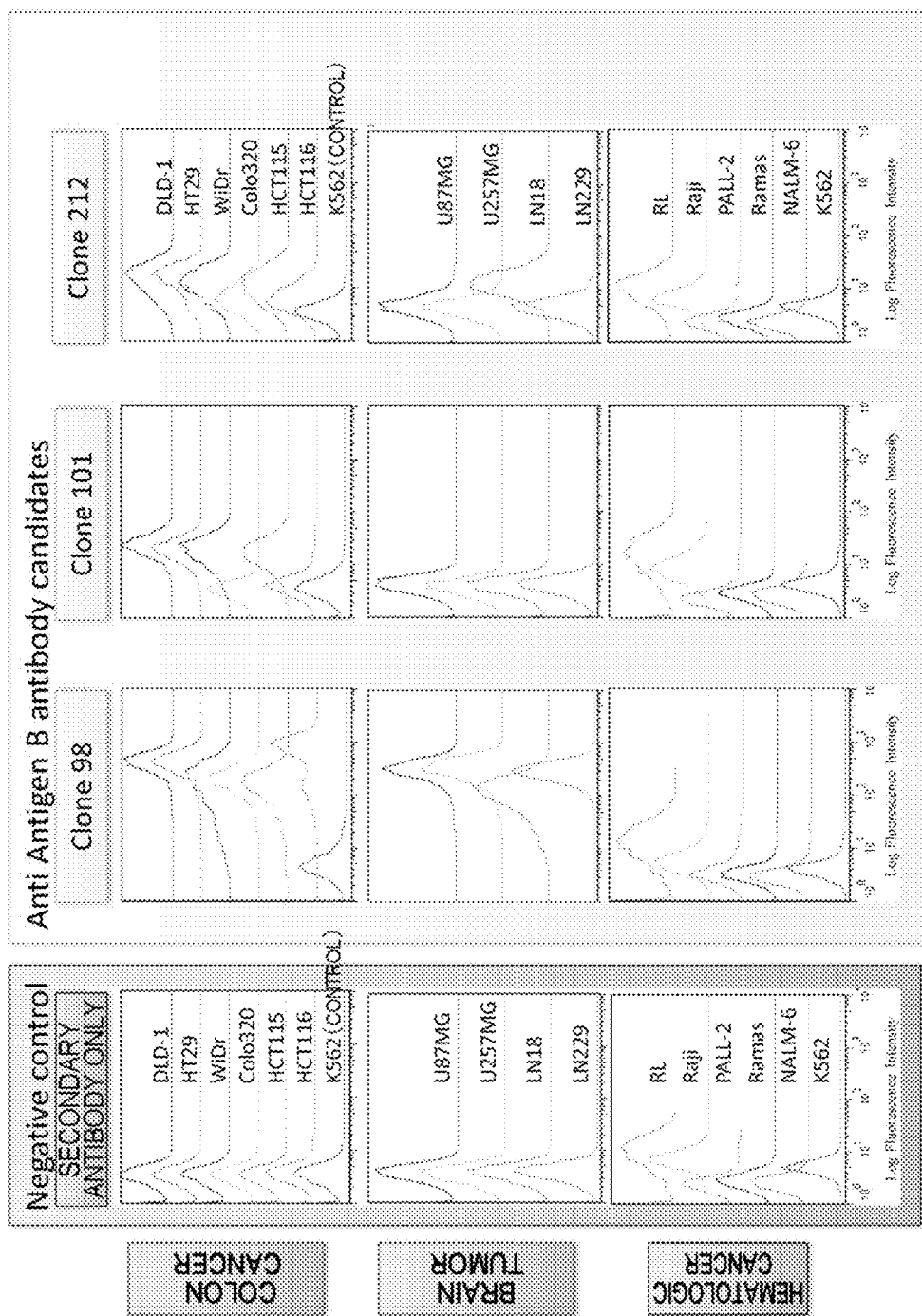
FIG. 3 indicates the results of a flow cytometry analysis of various colon cancer, brain tumor and hematologic cancer cell lines using anti-TMEM-180 antibody clones 98, 101 and 212.

The results of FACS analysis using the acquired anti-TMEM-180 IgM antibody are shown in FIG. 3. Clone 98 was positive for all six types of colon cancers and all four types of brain tumors while clone 101 was positive for four types of colon cancers and negative for all of the brain tumors. Clone 212 was positive for all six types of colon cancers and was positive for only one type of brain tumor. All of the clones were negative for hematologic tumors.

4. Fluorescent Immunostaining of DLD-1 Colon Cancer Cells

DLD-1 cells were added to a 96-well plate (Corning Incorporated, CellBIND) to a concentration of $5 \times 10^3$ cells/well and subjected to cell staining after culturing for 2 days. The cells were subjected to fixation and permeation treatment in the manner indicated below. After washing the cell culturing plate twice with PBS at 200 μL/well, the washings were removed followed by the addition of 4% para-formaldehyde-phosphate buffer (Wako Pure Chemical Industries, Ltd.) containing 0.1% TRITON X-100 (Wako Pure Chemical Industries, Ltd.) at 100 μL/well while cooling with ice and fixing the cells for 10 minutes. After removing the fixation solution, the plate was washed once with PBS at 200 μL/well and once with a mixture of 1% FBS in PBS at 200 μL/well to obtain a cell-immobilized plate. The cells were stained in the manner indicated below. Namely, after removing medium from the non-immobilized cell culturing plate and removing washings from the cell-immobilized plate, cell-producing hybridoma culture supernatant or diluted antibody solution was added at 50 μL/well. After allowing to react for 1 hour on ice, the plate was washed once with PBS at 200 μL/well and twice with a mixture of 1% FBS in PBS at 200 μL/well. After removing the washings, a mixture of 5 μg/mL ALEXAFLUOR 647 goat anti-rat IgG (H-L), 2 μg/mL Hoechst 33342 and 1% FBS/PBS was added at 50 μL/well. After allowing to react for 1 hour on ice, the plate was washed twice with PBS at 200 μL/well. PBS was then added at 50 μL/well followed by measuring with ArrayScan (Thermo Fisher Scientific Inc.).

Figure 4:
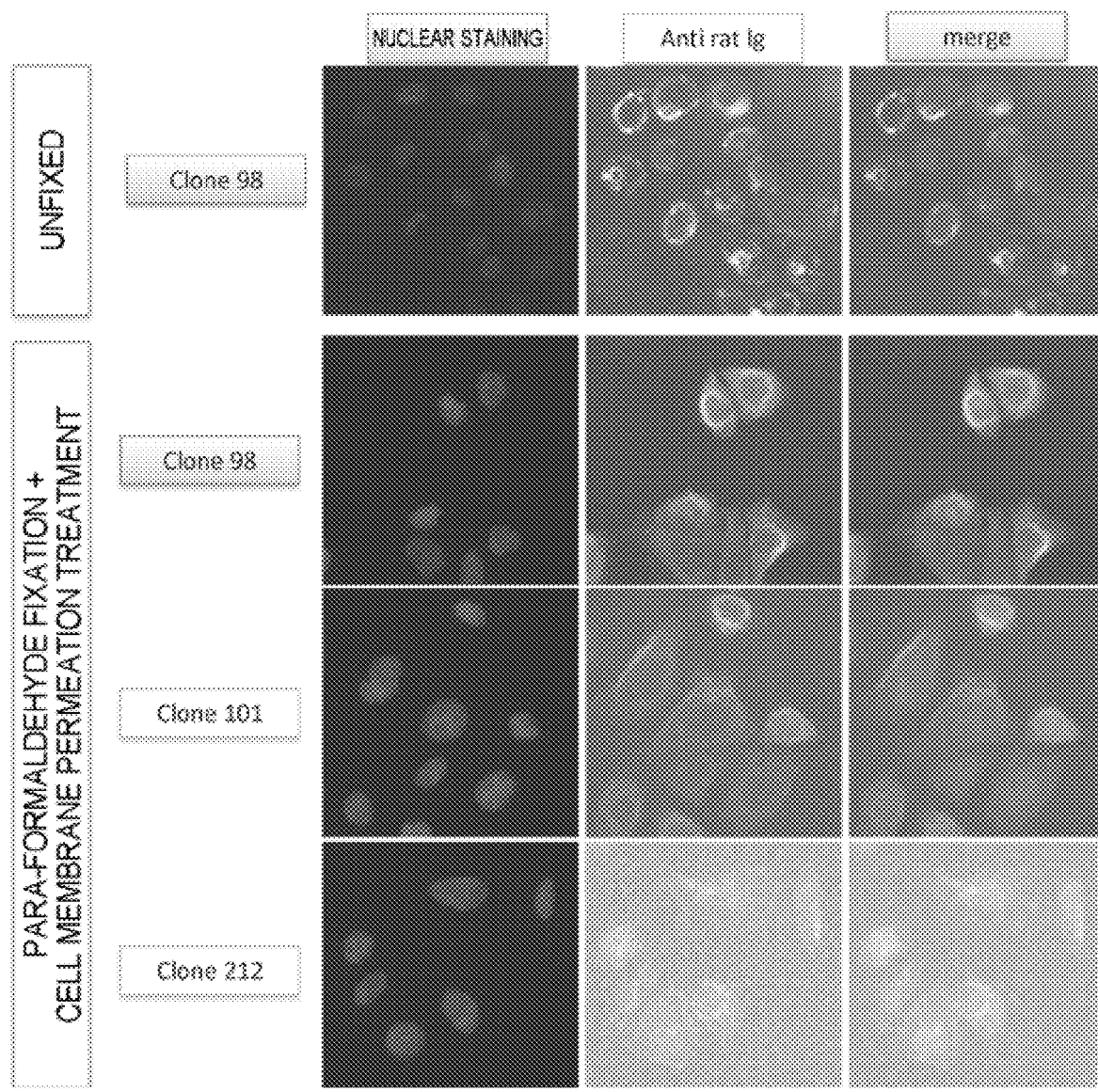
FIG. 4 indicates the results of immunofluorescent staining of colon cancer cells by anti-TMEM-180 antibody clones 98, 101 and 212. Furthermore, the antibody concentrations of each clone are not aligned.

The results of fluorescent immunostaining using clones 98, 101 and 212 of anti-TMEM-180 IgM antibody are shown in FIG. 4. Clone 98 was stained primarily in the membrane. Clones 101 and 212 exhibited weaker fluorescence intensity than clone 98 and the cytoplasm was also stained.

5. FACS of DLD-1 Parent Line and TMEM-180 Knockout Line Using Anti-TMEM-180 Antibody 1) Production of Knockout Cells Transfection 2.5 μg of Sigma CRISPR/Cas9 System (HS0000468201) plasmid were diluted with 0.5 mL of Opti-MEM (Invitrogen Corporation) followed by the addition of 11 μL of Lipofectionamine LTX. After allowing to stand undisturbed for 30 minutes at room temperature, DLD-1 cells ($6.26 \times 10^5$ cells/well, 6-well plate (Corning Incorporated)) were added to the DNA-Lipofection preparation.

Selection of GFP-Expressing Cells

Cells cultured for 2 days after transfection were subjected to cell sorting using the FACSAria Cell Sorter (BD) to acquire only cells that express GFP.

Cloning

After culturing the GFP-expressing cells and confirming that GFP was no longer expressed, the cells were subjected to limiting dilution in a 96-well plate. Genome purification was carried out on those wells containing only a single cell colony using the PureLink Genomic DNA Mini Kit (Invitrogen Corporation) followed by determining knockout cells by confirming the target sequence.

2) Flow Cytometry

Flow cytometry was carried out in accordance with the procedure described in the above-mentioned section 3. Rat IgM antibody clone 98 used as primary antibody was used after diluting antibody-producing hybridoma culture supernatant to 1 μg/mL. The supernatant of a culture of hybridoma producing rat IgM antibody clone 365 was used as a negative control after similarly diluting to 1 μg/mL. Rat-human chimeric antibody clone 98 was used after diluting the culture supernatant of chimeric antibody constantly-expressing cells two-fold. Human tissue factor antibody clone hTF1849, rat anti-human EpCAM antibody clone B8-4, mouse anti-human CD44v6 antibody clone 2F10 (Medical & Biological Laboratories Co., Ltd.) and mouse-human chimeric anti-EGFR antibody (trade name: Erbitux) were respectively used as positive controls after diluting to 1 μg/mL. A mixture of RPMI and 10% FBS was used to dilute each of the antibodies. Furthermore, antibody concentration in the hybridoma culture supernatant was measured by rat IgM-specific ELISA (Bethyl Laboratories). In addition, secondary antibody formed of any of ALEXAFLUOR 647 goat anti-rat IgG (H+L), ALEXAFLUOR 647 goat anti-human IgG (H+L) or ALEXAFLUOR 647 goat anti-mouse IgG (H+L) (Life Technologies Corporation) was used corresponding to the origin of the primary antibody after diluting 400-fold with a mixture of 0.1% BSA, 2 mM EDTA and PBS.

3) Production of Human Chimeric Antibody

Total RNA was extracted from the hybridoma cell lines and cDNA of variable regions of antibody H chain and variable regions of antibody L chain was synthesized with the SMARTer RACE cDNA Amplification Kit (Takara Bio Inc.) using the 5'-end rapid amplification of cDNA ends (RACE) method.

The synthesized cDNA was subjected to amplification by PCR and cloned to pUC19 (Invitrogen Corporation). The variable regions of the H chain and variable regions of the L chain are shown in subsequently indicated Tables 3 to 22.

After amplifying the variable regions of the H chain and L chain by PCR, the variable region of the H chain was inserted into pQCxIP incorporating a constant region (Clontech Laboratories, Inc.) while the variable region of the L chain was inserted into pQCxIH incorporating a constant region (Clontech Laboratories, Inc.) to complete the expression vector. The expression vector was then transfected into 293T cells using Lipofectamine 2000 (Invitrogen Corporation). Human anti-TMEM-180 antibody constantly expressing cell line was subjected to drug selection using puromycin (Sigma-Aldrich Co. LLC.) at 10 μg/mL and hygromycin B (Invitrogen Corporation) at 1 mg/mL and established by acquiring a cell line resistant to both drugs. The established cell line was subjected to maintenance culturing in DMEM (sigma) with 10% FBS, 1% penicillin-streptomycin (Invitrogen Corporation), 10 μg/mL of puromycin and 1 mg/mL of hygromycin B.

Figure 5:
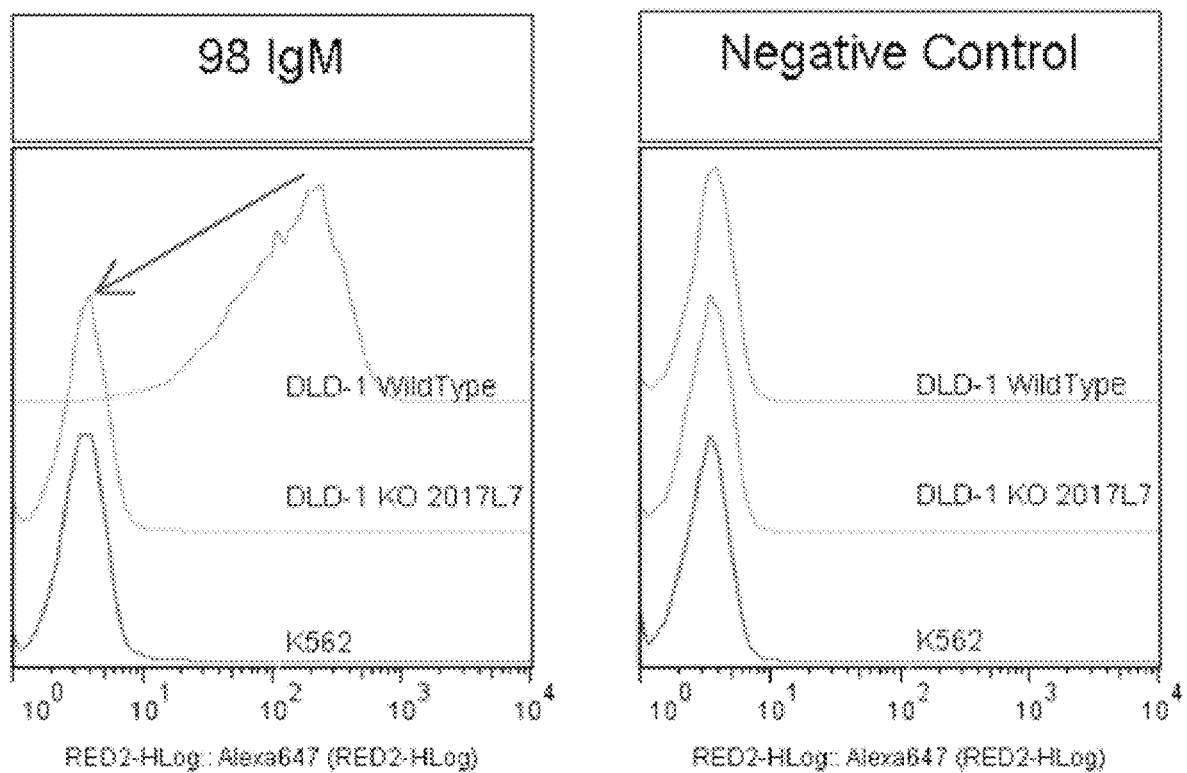
FIG. 5 indicates the results of investigating the reactivity of rat IgM antibody clone 98 and rat-human chimeric antibody clone 98 with colon cancer cell line DLD-1 and a TMEM-180 knockout line thereof by flow cytometry.
Figure 5:
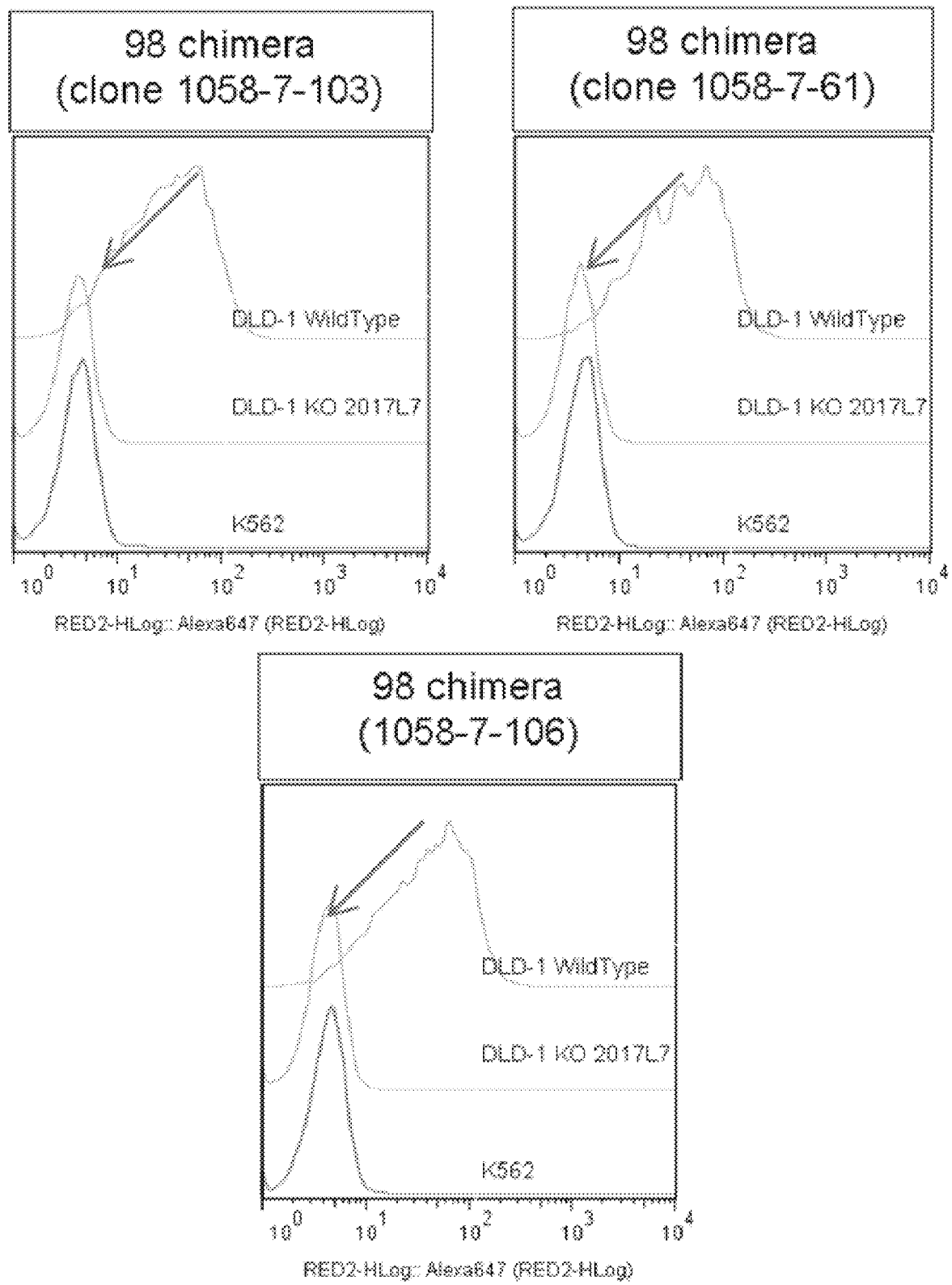

FACS was carried out on the colon cancer DLD-1 parent line and the TMEM-180 knockout line using rat IgM antibody clone 98 and human chimeric IgG antibody. The results are shown in FIG. 5. The rat IgM antibody clone 98 and human chimeric IgG antibody both demonstrated a considerable left shift. There were no differences between the parent line and knockout line in FACS using anti-tissue factor antibody, anti-EpCAM antibody, anti-CD44v6 antibody and anti-EGFR antibody as controls. This indicates that both rat IgM antibody clone 98 and human chimeric IgG antibody specifically recognize TMEM-180.

Figure 6:
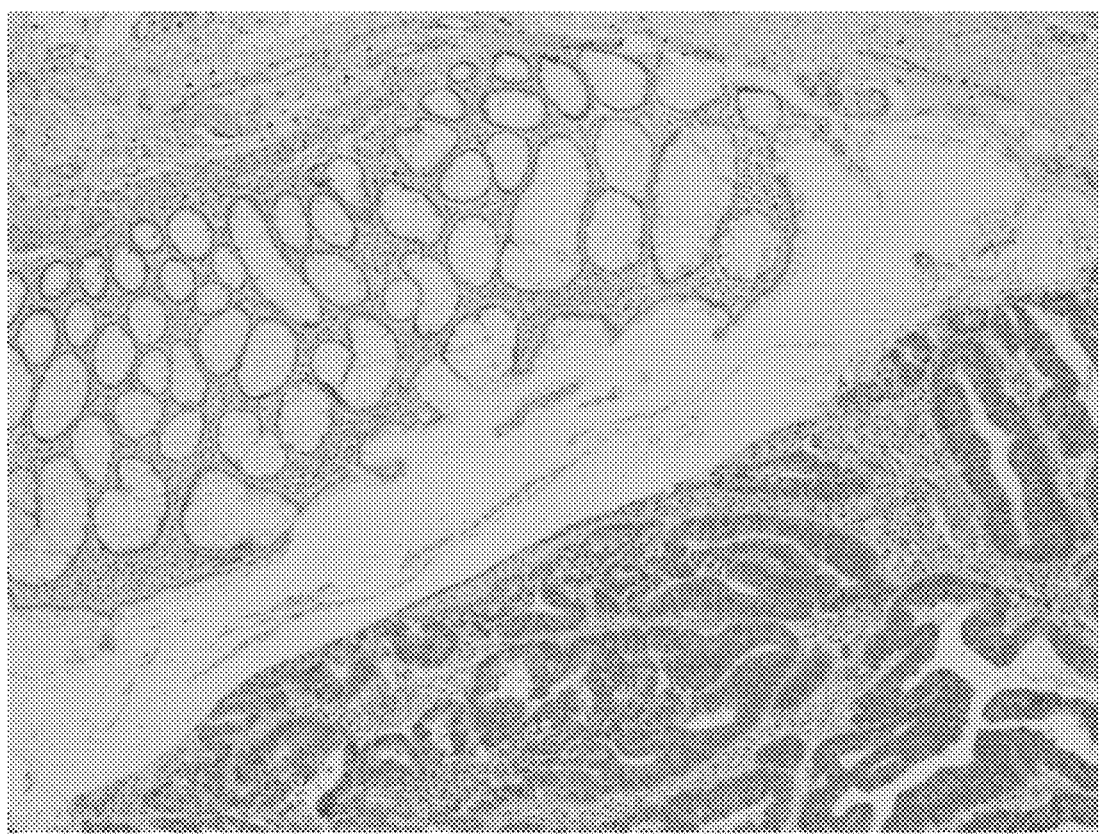
FIG. 6 indicates the results of staining human colon cancer and nearby normal tissue using rat IgM antibody clone 98.

6. Immunostaining of Formalin-Fixed Section of Human Colon Cancer Surgical Specimens by Anti-TMEM-180 Antibody Anti-TMEM-180 IgM rat antibody (clone 98) was reacted with a colon cancer formalin-fixed section at 1 μg/mL. HRP-labeled anti-rat antibody was used as secondary antibody and the section was stained with DAB followed by post-staining with hematoxylin. The result is shown in FIG. 6. Colon cancer was shown to be stained specifically. Both the cell membrane and cytoplasm of the colon cancer cells were stained.

7. Cytocidal Effect of Anti-TMEM-180 IgM Antibody

Figure 7:
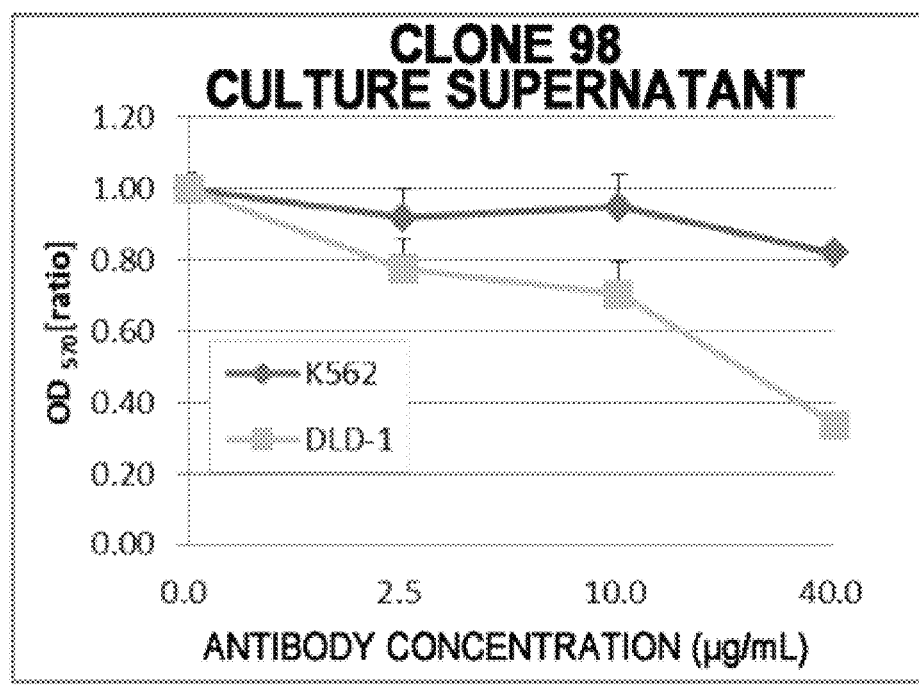
FIG. 7 indicates the results of a cytotoxicity test using culture supernatant of a hybridoma producing rat IgM antibody clone 98. Antibody concentration in the hybridoma culture supernatant was measured by ELISA using IgM-specific antibody.
Figure 8:
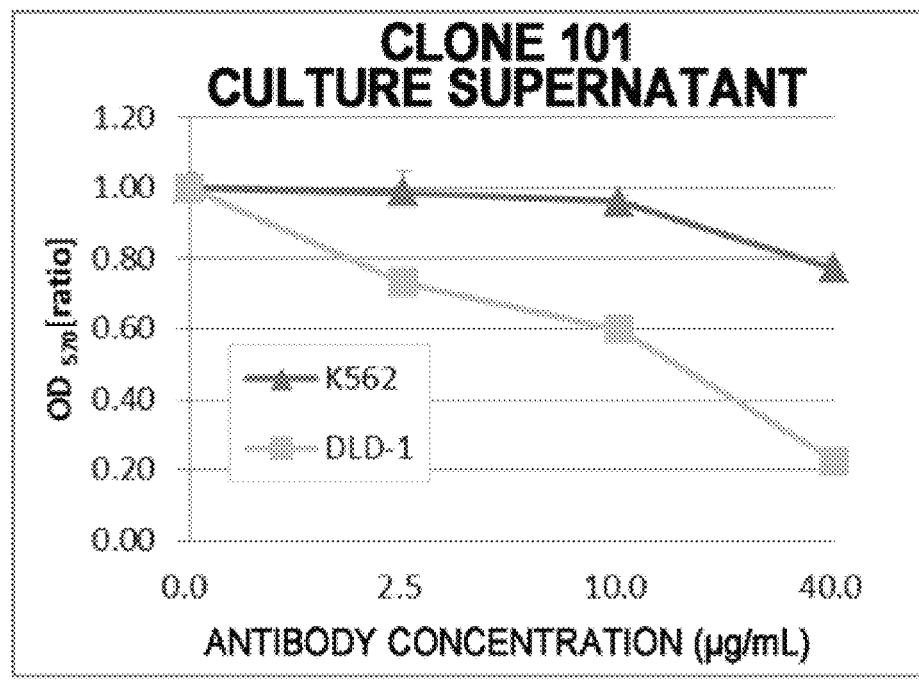
FIG. 8 indicates the results of a cytotoxicity test using culture supernatant of a hybridoma producing rat IgM antibody clone 101. Antibody concentration in the hybridoma culture supernatant was measured by ELISA using IgM-specific antibody.

DLD-1 cells and K562 cells were added to a 96-well plate at $1\times10^3$ cells/100 μL/well followed by culturing for 24 hours. 50 μL of medium were removed from each well of the 96-well plate followed by the addition of rat IgM antibody clone 98-producing hybridoma culture supernatant or rat IgM antibody clone 101-producing hybridoma culture supernatant, in which antibody concentration had been adjusted to 80 μg/mL, 20 μg/mL or 5 μg/mL, at 50 μL/well. Here, n number in each culture condition was 3, and wells containing medium only were prepared as controls. is added After culturing for 96 hours, WST-8 (Dojindo Laboratories, Cell Counting Kit-8) was added at 10 μL/well followed by measuring absorbance at 450 nm with a microplate reader after culturing for 3 hours. The relative values of absorbance at each antibody concentration were plotted by plotting antibody concentration on the horizontal axis and assigning a value of 1 to the optical absorbance of the well containing medium only. The results are shown in FIGS. 7 and 8. Both clone 98 and clone 101 only demonstrated cytocidal effects against colon cancer DLD-1 cells and did not demonstrate cytocidal effects against hematologic tumor K562 cells. Cytocidal effects were also observed for other colon cancer cells Difi, Car1, SW480 and Colo201. In addition, similar effects were observed for brain tumor LN229 cells and breast cancer MCF7 cells. Cytocidal effects are therefore predicted to be demonstrated against a wide range of cancers other than hematologic tumors.

8. Determination of the Base Sequences and CDR of the Variable Portion of Each Clone

1) Extraction of Total RNA

Total RNA was extracted from each antibody-producing hybridoma using the RNeasy Mini Kit (Qiagen).

2) Production of cDNA cDNA was synthesized with the SMARTer RACE cDNA Amplification Kit (Takara Bio Inc.) according to the 5'-end rapid amplification of cDNA ends (RACE) method using the total RNA obtained in the manner described above.

3) Cloning of Anti-TMEM-180 Antibody Gene

The target gene was amplified by using PrimeStar HS DNA Polymerase (Takara Bio Inc.) on the above-mentioned cDNA. Amplification was carried out by touchdown PCR under amplification condition of 5 cycles of denaturing for 10 seconds at 98° C. and annealing/extending for 90 seconds at 72° C., 5 cycles of denaturing for 10 seconds at 98° C., annealing for 5 seconds at 67° C. and extending for 90 seconds at 72° C., and 25 cycles of denaturing for 10 seconds at 98° C., annealing for 5 seconds at 62° C. and extending for 90 seconds at 72° C.

PCR device: Takara PCR Thermal Cycler Dice Gradient
Primer sequences used:

H chain primer:
Forward primer:
(SEQ ID NO: 26)
CTAATACGACTCACTATAGGGCAAGCAGTGGTATCAACGCAGAGT Forward primer:
(SEQ ID NO: 27)
CTAATACGACTCACTATAGGGC Reverse primer:
(SEQ ID NO: 28)
CCCATGGCCACCARATTCTYATCAGACAG L chain primer:
Forward primer:
(SEQ ID NO: 29)
CTAATACGACTCACTATAGGGCAAGCAGTGGTATCAACGCAGAGT Forward primer:
(SEQ ID NO: 30)
CTAATACGACTCACTATAGGGC Reverse primer:
(SEQ ID NO: 31)
GTTGTTCAWGARGCACACGACTGAGGCA The amplified PCR products of the H chain and L chain were phosphorylated using T4 Polynucleotide Kinase (Takara Bio Inc.). The phosphorylated PCR products were inserted into pUC19 (Invitrogen Corporation) cleaved at the SmaI site using Ligation High reagent (Toyobo Co., Ltd.). Following insertion, the PCR products were transformed to DH5α (Toyobo Co., Ltd.) and plasmids were extracted from single colonies using the Plasmid Mini Kit (Qiagen).

4) Gene Analysis

Genes of each of the cloned H chains and L chains were analyzed for gene base sequence using the ABI Prism 3100 Genetic Analyzer. The sequences of the H chain variable region and L chain variable region of each clone are shown in Tables 3 to 22.

Clone 98 H Chain (SEQ ID NO: 13)

TABLE 3

```
  1 ATG GCT GTC CTG GTC CTG TTG CTC TGC CTG GTG ACA TTT CCA ACC TCT GTC CTG TCC CAG  60
    M   A   V   L   V   L   L   L   C   L   V   T   F   P   T   C   V   L   S   Q

61 GTG CAG CTG AAG GAG TCA GGA CCT GGT CTG GTG CAG CCC TCA CAG ACC CTG TCC CTC ACC 120
    V   Q   L   K   E   S   G   P   G   L   V   Q   P   S   Q   T   L   S   L   T

CDR1
121 TGC ACT GTC TCT GGG TTC TCA CTA ACC AGG TAC AAT GTG CAC TGG GTT CGA CAG CCT ACA 180
    C   T   V   S   G   F   S   L   T   R   Y   N   V   H   W   V   R   Q   P   T

CDR2
181 GGA AAA GGT CTG GAG TGG ATG GGA GTA ATA TGG ACT GGT GGA AGC ACA GAT TAC AAT TCA 240
    G   K   G   L   E   W   M   G   V   I   W   T   G   G   S   T   D   Y   N   S

241 GCT CTC AAA TCC CGA CTG AGC ATC AGC AGG GAC ACC TCC AAG AGC CAA CTT TTC TTA AAA 300
    A   L   K   S   R   L   S   I   S   R   D   T   S   K   S   Q   V   F   L   K

CDR3
301 ATG AAC AGT CTG CAA ACT GAA GAC ATA GCC ACT TAC TAC TGT GCC AGA GAT CTG GGT TAC 360
    M   N   S   L   Q   T   E   D   I   A   T   Y   Y   C   A   R   D   L   G   Y

361 TGG GGC CAA GGA CTC ATG GTC ACA GTC TCC TCA                                     393
    W   G   Q   G   L   M   V   T   V   S   S
```

Clone 98 L Chain (SEQ ID NO: 14)

TABLE 4

```
  1 ATG ATG AGT CCT GCC CAG TTC CTG TTT CTG CTA ATG CTC TGG ATC CAG GAA ACC CAC AGT  60
    M   M   S   P   A   Q   F   L   F   L   L   M   L   W   I   Q   E   T   H   S

61 GAT ATT GTG ATG ACA CAG ACT CCA CTC TCT TTG TCA GTT GCC ATT GCA CAA TCA GCC TCC 120
    D   I   V   M   T   Q   T   P   L   S   L   S   V   A   I   G   Q   S   A   S

CDR1
121 ATC TCT TGC AAA TCG AGT CAG AGC CTC AAA TAT CGT GAT GGA AAG ACA TAT TTG AAT TGG 180
    I   S   C   K   S   S   Q   S   L   K   Y   R   D   G   K   T   Y   L   N   W

CDR2
181 GTA TTT CAG AGT CCT GCC AGT CTC CAA AGC GCC TAA ATC TAT CAG GTG TCT AAA CTG GAC 240
    V   F   Q   S   P   G   Q   S   P   K   R   L   I   Y   Q   V   S   K   L   D
```

TABLE 4-continued

```
241 [TCT] GGA GTT CCT GAC AGG TTC AGT GGC ACT GGA TCA GAG ACA GAT TTT ACA CTT AAA ATC 300
    [ S ]  G   V   P   D   R   F   S   G   T   G   S   E   T   D   F   T   L   K   I

CDR3
301 AGC AGA GTG GAG GCA GAC GAT TTG CGA CTT TAT TAC TCC [TGT CAA GCT TCA TAT TCT CCT] 360
     S   R   V   E   A   D   D   L   R   L   Y   Y   S  [ C   Q   G   S   Y   S   P ]

361 [CAC ACG] TTT GGA GCT GGG ACC AAG CTG CAA CTG AAA                                 396
    [ H   T ]  F   G   A   G   T   K   L   E   L   K
```

Clone 101 H Chain (SEQ ID NO: 15)

TABLE 5

```
  1 ATG GCT ATC CTG GTG CTG CTT CTC TGC CTG GTG ACC ATT CCA CAC TCT GTC TTG TCC CAG  60
     M   A   I   L   V   L   L   L   C   L   V   T   I   P   H   S   V   L   S   Q

61 GTG CAG CTG AAG GAG ACA GGA CCT GGC CTG GTG CAA CCA ACA CAG ACC CTG TCC ATC ACA 120
     V   Q   L   K   E   T   G   P   G   L   V   Q   P   T   Q   T   L   S   I   T

CDR1
121 TGT ACT GTT TCT [GGG TTC TCA TTA ACC AGC TAT TAT ATG CAG] TGG GTT CGC CAG ACT CCA 180
     C   T   V   S  [ G   F   S   L   T   S   Y   Y   M   Q ]  W   V   R   Q   T   P

CDR2
181 GGA AAG GGA CTA GAA TGG ATG GGA [TTT ATA CGG AGT GGT GGA AGC ACA GAG] TAT AAT TCA 240
     G   K   G   L   E   W   M   G  [ F   I   R   S   G   G   S   T   E ]  Y   N   S

241 GAG TTC AAA TCC CGA CTT AGC ATC AGC AGG GAC ACC TCC AAG AAC CAA GTT TTC TTA AAA 300
     E   F   K   S   R   L   S   I   S   R   D   T   S   K   N   Q   V   F   L   K

CDR3
301 ATG AAC AGT CTG AAA ACA GAG GAC ACA GGC GTG TAC TAC TGT GCC AGA [GCC TTC TAC GGA 360
     M   N   S   L   K   T   E   D   T   G   V   Y   Y   C   A   R  [ A   F   Y   G

361 GGG TAC TAC TTT GAT TAC] TGG GGC CAA GGA GTC ATG GTC ACA GTC TCC TCA            411
      G   Y   Y   F   D   Y]  W   G   Q   G   V   M   V   T   V   S   S
```

Clone 101 L Chain (SEQ ID NO: 16)

TABLE 6

```
  1 ATG GGC ATC AGG ATG GAG TCA CAT ACT AGG GTC TTC ATA TTC CTG CTG CTC TGG TTG TCT  60
     M   G   I   R   M   E   S   H   T   R   V   F   I   F   L   L   L   W   L   S

61 GGT GCT GAT GGG GAC ATT GTG ATG ACT CAG TCT CCC ACA TCC ATT TCC ATA TCA GTA GGA 120
     G   A   D   G   D   I   V   M   T   Q   S   P   T   S   I   S   I   S   V   G

CDR1
121 GAG AGG GTC ACC ATG AAC TGC [AAG GCC AGT CAG AAT GTG GGT TCT AAT GTA GAC] TGG TAC 180
     E   R   V   T   M   N   C  [ K   A   S   Q   N   V   G   S   N   V   D ]  W   Y

CDR2
181 CAA CAG AAA ACA GGG CAG TCT CCT AAA CTG CTT ATC TAC [AAG GCA TCC AAC CGG TAC ACT] 240
     Q   Q   K   T   G   Q   S   P   K   L   L   I   Y  [ K   A   S   N   R   Y   T ]

241 GGC GTC CCT GAT CGC TTC ACA GGC AGT GGA TCT GGA ACA GAT TTC ACT TTC ACC ATC AGC 300
     G   V   P   D   R   F   T   G   S   G   S   G   T   D   F   T   F   T   I   S

CDR3
300 AAC ATG CAG GCT GAA GAC CTG GCT GTT TAT TAC TGT [ATG CAG TCT AAC ACC AAG TAC ACG 360
     N   M   Q   A   E   D   L   A   V   Y   Y   C  [ M   Q   S   N   T   K   Y   T

361 TTT GCA GCT GGG ACC AAG CTG GAA CTG AAA                                           390
      F   G   A   G   T   K   L   E   L   K
```

Clone 212 H Chain (SEQ ID NO: 46)

TABLE 7

```
  1  ATG GAC ATC AGG CTC AGC TTG GCT TTC CTT GTC CTT TTC ATA AAA GGT GTC CAG TGT GAG  60
     M   D   I   R   L   S   L   A   F   L   V   L   F   I   K   G   V   Q   C   E

61  GTG CAG CTG GTG GAG TCT GGC GGA GGA TTG GTA CAG CCT GGA AAC TCC CTG AAA CTC TCC 120
     V   Q   L   V   E   S   G   G   G   L   V   Q   P   G   N   S   L   K   L   S

CDR1
121  TGT GCA GCC TCA |GGA TTC ACT TTC AGT GAC TAT GCC ATG GCC| TGG GTC CGC CAG TCT CCA 180
     C   A   A   S   |G   F   T   F   S   D   Y   A   M   A  | W   V   R   Q   S   P

CDR2
181  AAG AAG GGT CTG GAG TGG GTC GCA |ACC ATT ATT TAT GAT GGT AGT AGC ACT| TAC TAT CGA 240
     K   K   G   L   E   W   V   A   |T   I   I   Y   D   G   S   S   T  | Y   Y   R

241  GAC TCC GTG AAG GGC CGA TTC ACT ATC TCC AGA GAT AAT GCA AAA AGC ACC CTA TAC CTG 300
     D   S   V   K   G   R   F   T   I   S   R   D   N   A   K   S   T   L   Y   L

CDR3
301  CAA ATG GAC AGT CTG AGG TCT GAG GAC ACG GCC ACT TAT TAC TGT GCA ACA |CAT TGG TAC 360
     Q   M   D   S   L   R   S   E   D   T   A   T   Y   Y   C   A   T  |H   W   Y

361  TGG TAC TTT GAC TTC| TGG GGC CCA GGA ACC ATG GTC ACC GTG TCC TCA                408
     W   Y   F   D   F | W   G   P   G   T   M   V   T   V   S   S
```

Clone 212 L Chain (SEQ ID NO: 47)

TABLE 8

```
  1  ATG GGT GTG CCC ACT CAG CTC CTG GGG TTG TTG CTG CTC TGG ATT ACA GAT GCC ATA TGT  61
     M   G   V   P   T   Q   L   L   G   L   L   L   L   W   I   T   D   A   I   C

61  GAC ATC CAG ATG ACA CAG TCT CCA GCT TCC CTG TCT GCA TCT CTT GGA GAA ACT GTC TCC 120
     D   I   Q   M   T   Q   S   P   A   S   L   S   A   S   L   G   E   T   V   S

121                      CDR1                                                       180
     ATC GAA TGT |CTA GCA AGT GAG GGC ATT TCC AAT GAT TTA GCG| TGG TAT CAG CAG AAG TCA
     I   E   C  |L   A   S   E   G   I   S   N   D   L   A  | W   Y   Q   Q   K   S

181                              CDR2                                               240
     GGG AAA TCT CCT CAG CTC CTG ATC TAT |GCT GCA AGT AGG TTG CAA GAC| GGG GTC CCA TCA
     G   K   S   P   Q   L   L   I   Y  |A   A   S   R   L   Q   D  | G   V   P   S

241  CGG TTC AGT GGC AGT GGA TCT GGC ACA CGG TAT TCT CTC AAG ATC AGC GGC ATG CAA TCA 240
     R   F   S   G   S   G   S   G   T   R   Y   S   L   K   I   S   G   M   Q   P

301                              CDR3                                               360
     GAA GAT GAA GCA GAT TAT TTC TGT |CAA CAG AGT TAC AAG TAT CCT CTC ACG| TTC GGT TCT
     E   D   E   A   D   Y   F   C  |Q   Q   S   Y   K   Y   P   L   T  | F   G   S

361  GGG ACC AAG CTG GAG ATC AAA                                                    381
     G   T   K   L   E   I   K
```

Clone 129 H Chain (SEQ ID NO: 54)

TABLE 9

```
     ATG GAT TGG TTG TGG AAC TTG CTA TTC CTG ATG GTA GTT GCC CAA AGT GCT CAA GCA CAG
     M   D   W   L   W   N   L   L   F   L   M   V   V   A   Q   S   A   Q   A   Q

ATC CAG TTG GTA CAG TCT GGT CCT GAA CTG AAG AAG CCT GGA GAG TCA GTG AAG ATC TCC
     I   Q   L   V   Q   S   G   P   E   L   K   K   P   G   E   S   V   K   I   S

CDR1
     TGC AAG GCT TCT GGG TAT ACC TTC ACA |GAC TGT GCA CTG AAC| TGG GTG AAA CAG GCT CCA
     C   K   A   S   G   Y   T   F   T  |D   C   A   L   N  | W   V   K   Q   A   P
```

TABLE 9-continued

```
                                      CDR2
GGA AAT GGC TTG AAG TGG ATG GGC TGG ATC AAC ACC CAA ACT GGA AAG CCA ACA TAT GCG
 G   N   G   L   K   W   M   G   W   I   N   T   Q   T   G   K   P   T   Y   A

GAT GAT TTC AAA CAA CGG TTT GTC TTC TCC TTG GAA ACT TCT GCC AGC ACT GCA TAC TTG
 D   D   F   K   Q   R   F   V   F   S   L   E   T   S   A   S   T   A   Y   L
                                                                      CDR3
CAG ATC AAC AAC CTC AAT ATT GAG GAC ACA GCT ACA TAT TTC TGT ACA AGA GAG GAC TAC
 Q   I   N   N   L   N   I   E   D   T   A   T   Y   F   C   T   R   E   D   Y

GGG TAT TTT GAT TAC TGG GGC CAA GGA GTC ATG GTC ACA GTC TCC TCA
 G   Y   F   D   Y   W   G   Q   G   V   M   V   T   V   S   S
```

Clone 129 L Chain (SEQ ID NO: 55)

TABLE 10

```
ATG AGG ACT TCA ATT CAA CTC CTG GGG CTC CTG TTG CTC TGG CTT CAT GAT GCT CAG TGT
 M   R   T   S   I   Q   L   L   G   L   L   L   L   W   L   H   D   A   Q   C

GAC ATC CAA ATG ACA CAG TCT CCT CCC TCC CTG TCT GCA TCT CTG GGA GAC AAA GTC ACC
 D   I   Q   M   T   Q   S   P   P   S   L   S   A   S   L   G   D   K   V   T
                  CDR1
ATC ACT TGC CAG GCA AGT CAA AAC ATT AAC AAA TTT ATA GCT TGG TAT CAG CAA AAG CCT
 I   T   C   Q   A   S   Q   N   I   N   K   F   I   A   W   Y   Q   Q   K   P
                                     CDR2
GGA AAA GCT CCT AGG CAT CTC GTA CAT TAC ACT TCT ACA CTA GTG TCA GGC ACC CCA TCG
 G   K   A   P   R   H   L   V   H   Y   T   S   T   L   V   S   G   T   P   S

AGG TTC AGT GGC AGT GGA TCT GGG AGA GAT TAT TCA TTC AGC ATC AGC AAC GTG GAG TCT
 R   F   S   G   S   G   S   G   R   D   Y   S   F   S   I   S   N   V   E   S
                                CDR3
GAA GAT ATT GCA AGT TAT TAC TGT CTA CAG TAC GAT AAC CTT CGG ACG TTC GGT GGA GGC
 E   D   I   A   S   Y   Y   C   L   Q   Y   D   N   L   R   T   F   G   G   G

ACC AAG CTG GAA TTG AAA
 T   K   L   E   L   K
```

Clone 382 H Chain (SEQ ID NO: 62)

TABLE 11

```
ATG GAC ATC AGG CTC AGC TTG GGT TTC CTT GTC CTT TTC ATA AAA GGT GTC CAA TGT GAG
 M   D   I   R   L   S   L   G   F   L   V   L   F   I   K   G   V   Q   C   E

GTG CAG CTG GTG GAG TCT GGG GGC GGC TTG GTG CAG CCT GGA AGG TCC CTG AAA CTC TCC
 V   Q   L   V   E   S   G   G   G   L   V   Q   P   G   R   S   L   K   L   S
                                        CDR1
TGT GCA GCC TCA GGA TTC ACT TTC AGT AAC TAT GGC ATG CAC TGG ATC CGC CAG GCT CCA
 C   A   A   S   G   F   T   F   S   N   Y   G   M   H   W   I   R   Q   A   P
                                 CDR2
ACG AAG GGT CTC GAG TGG GTC GCA TCC ATT AGT CCT AGT GGT GGT AGC ACT TAC TAT CGA
 T   K   G   L   E   W   V   A   S   I   S   P   S   G   G   S   T   Y   Y   R

GAC TCC GTG AAG GGC CGA TTC ACT ATC TCC AGG GAT AAT GCA AAA AGC ACC CTA TAC CTG
 D   S   V   K   G   R   F   T   I   S   R   D   N   A   K   S   T   L   Y   L
                                                                  CDR3
CAA ATG GAC AGT CTG AGG TCT GAG GAC ACG GCC ACT TAT TAC TGT GCA ACC AGC GCG TCT
 Q   M   D   S   L   R   S   E   D   T   A   T   Y   Y   C   A   T   S   A   S
```

TABLE 11-continued

```
ATA ACA GCA TAT TAC TAT GTT ATG GAT GCC TGG GGT CAA GGA GCT TCA GTC ACT GTC TCC
 I   T   A   Y   Y   Y   V   M   D   A   W   G   Q   G   A   S   V   T   V   S

TCA
 S
```

Clone 382 L Chain (SEQ ID NO: 63)

TABLE 12

```
ATG GAG TCA CAT ACT AGG GTC TTC ATA TTC CTG CTG CTC TGG TTG TCT GGT GCT GAT GGG
 M   E   S   H   T   R   V   F   I   F   L   L   L   W   L   S   G   A   D   G

GAC ATT GTG ATG ACT CAG TCT CCC ACA TCC ATG TCC ATA TCA GTA GGA GAC AGG GTC ACC
 D   I   V   M   T   Q   S   P   T   S   M   S   I   S   V   G   D   R   V   T

CDR1
ATG AAC TGC AAG GCC AGT CAA AAT GTG GGT TCT AAT GTA GAC TGG TAC CAA CAG AAA ACA
 M   N   C   K   A   S   Q   N   V   G   S   N   V   D   W   Y   Q   Q   K   T

CDR2
GGG CAG TCT CCT AAA CTG CTT ATC TAC AAA GCA TCC AAC CGG TAC ACG GGA GTC CCT GAT
 G   Q   S   P   K   L   L   I   Y   K   A   S   N   R   Y   T   G   V   P   D

CGC TTC ACA GGC AGT GGA TCT GGA ACA GAT TTC ACT TTC ACC ATC AGC AAC ATG CAG GCT
 R   F   T   G   S   G   S   G   T   D   F   T   F   T   I   S   N   M   Q   A

CDR3
GAA GAC CTG GCT GTT TAT TAC TGT ATG CAG TCT AAC TCC TAT CCT CCG ACG TTC GGT GGA
 E   D   L   A   V   Y   Y   C   M   Q   S   N   S   Y   P   P   T   F   G   G

GGC ACC AAG CTG GAA TTG AGA
 G   T   K   L   E   L   R
```

Clone 1361 H Chain (SEQ ID NO: 70)

TABLE 13

```
ATG GAC ATC AGG CTC AGC TTG GTT TTC CTT GTC CTT TTC ATA AAA GGT GTC CAG TGT GAG
 M   D   I   R   L   S   L   V   F   L   V   L   F   I   K   G   V   Q   C   E

GTG CAG CTG GTG GAG TCT GGG GGA GGC CTA GTG CAG CCT GGA AGG TCT CTG AAA CTA TCC
 V   Q   L   V   E   S   G   G   G   L   V   Q   P   G   R   S   L   K   L   S

CDR1
TGT GTA GCC TCT GGA TTC ACA TTC AAT AAC TAC TGG ATG ACC TGG ATC CGC CAG GCT CCA
 C   V   A   S   G   F   T   F   N   N   Y   W   M   T   W   I   R   Q   A   P

CDR2
GGG AAG GGG CTG GAG TGG GTT GCA TCC ATT ACT AAT ACT GGT GGT AGC ACT TAC TAT CCA
 G   K   G   L   E   W   V   A   S   I   T   N   T   G   G   S   T   Y   Y   P

GAC TCT GTG AAG GGC CGA TTC ACT ATC TCC AGA GAT TAT GCA AAA AGC ACC CTA TAC CTG
 D   S   V   K   G   R   F   T   I   S   R   D   Y   A   K   S   T   L   Y   L

CDR3
CAA ATG AAC AGT CTG AGG TCT GAG GAC ACG GCC ACT TAT TAC TGT ACA AGA GCT GGC TAT
 Q   M   N   S   L   R   S   E   D   T   A   T   Y   Y   C   T   R   A   G   Y

AGC AGC TAT CCC GAC TAC TTT GAT TAC TGG GGC CAA GGA GTC ATG CTC ACA GTC TCC TCA
 S   S   Y   P   D   Y   F   D   Y   W   G   Q   G   V   M   L   T   V   S   S
```

Clone 1361 L Chain (SEQ ID NO: 71)

TABLE 14

```
ATG ATG GCT CCA GTT CAA CTC TTA GGG CTG CTG CTG CTC TGG CTC CCA GCC ATG AGA TGT
 M   M   A   P   V   Q   L   L   G   L   L   L   L   W   L   P   A   M   R   C

AAC ATC CAG ATG ACC CAG TCT CCT TCA CTA CTC TCT GCA TCT GTG GGA GAC AGA GTC ACT
 N   I   Q   M   T   Q   S   P   S   L   L   S   A   S   V   G   D   R   V   T

CDR1
CTC AGC TGC AAA GCA GGT CAG AAT ATT TAC AAT TAC TTA GCC TGG TAT CAG CAA AAG CTT
 L   S   C  |K   A   G   Q   N   I   Y   N   Y   L   A  |W   Y   Q   Q   K   L

CDR2
GGA GAA GCT CCC AAA CTC CTG ATT TAT AAT GCA AAC AGT TTG CAA ACG GGC ATC CCA TCA
 G   E   A   P   K   L   L   I   Y  |N   A   N   S   L   Q   T  |G   I   P   S

AGG TTC AGT GGC AGT GGA TCT GGT ACA GAT TTC ACA CTC ACC ATC AGC AGC CTG CAG CCT
 R   F   S   G   S   G   S   G   T   D   F   T   L   T   I   S   S   L   Q   P

CDR3
GAA GAT GTT GCC ACA TAT TTC TGC CAG CAG TAT AGC AGT GGG TGG ACG TTC GGT GGA GGC
 E   D   V   A   T   Y   F   C  |Q   Q   Y   S   S   G   W  |T   F   G   G   G

ACC AAG CTG GAA TTG AAA
 T   K   L   E   L   K
```

Clone 669 H Chain (SEQ ID NO: 78)

TABLE 15

```
1    ATG GGA TGG ATC TGT ATC ATC TTT CTT GTG GCA ACA GCT ACA GGT GTC CAC TCC CAG GTC  60
      M   G   W   I   C   I   I   F   L   V   A   T   A   T   G   V   H   S   Q   V

61   AAG CTG CTG CAG TCT GGG GCT GCA CTG GTG AAG CCT GGA GCC TCT GTG AAG ATG TCT TGC 120
      K   L   L   Q   S   G   A   A   L   V   K   P   G   A   S   V   K   M   S   C

121                                 CDR1                                             180
     AAA GCT TCT GGT TAT ACA TTC ACT GAC TAC TGG GTG AGC TGG GTG AAG CAG AGT CAT GGA
      K   A   S   G   Y   T   F   T  |D   Y   W   V   S  |W   V   K   Q   S   H   G

181                           CDR2                                                   240
     AAG AGC CTT GAG TGG ATT GGG GAA ATT TAT CCT AAC AGT GGT GCT ACT AAC TTC AAT GAA
      K   S   L   E   W   I   G  |E   I   Y   P   N   S   G   A   T   N   F   N   E

241  AAC TTC AAG GGC AAG GCC ACA TTG ACT GTA GAC AAA TCC ACC AGC ACA GCC TAT ATG GAG 300
     |N   F   K |G   K   A   T   L   T   V   D   K   S   T   S   T   A   Y   M   E

301                                                             CDR3                 360
     CTC AGC AGA TTG ACA TCT GAG GAC TCT GCA ATC TAT TAC TGT ACA AGA GAC GGG ACT ATG
      L   S   R   L   T   S   E   D   S   A   I   Y   Y   C   T   R  |D   G   T   M

361  GGT ATA GCC TAC TAC TTT GAT TAC TGG GGC CAA GGA GTC ATG GTC ACA GTC TCC TCA     420
      G   I   A   Y   Y   F   D   Y |W   G   Q   G   V   M   V   T   V   S   S
```

Clone 669 L Chain (SEQ ID NO: 79)

TABLE 16

```
1    ATG ATG GCT GCA GTT CAA CTC TTA GGG CTG CTG CTG CTT TGG GTC CCA GCC ATG AGA TGT  60
      M   M   A   A   V   Q   L   L   G   L   L   L   L   W   V   P   A   M   R   C

61   GAC ATC CAG ATC ACC CAG TCT CCT TCA TTC CTG TCT GCA TCT GTG GGA GAC AGA GTC ACT 120
      D   I   Q   M   T   Q   S   P   S   F   L   S   A   S   V   G   D   R   V   T

121           CDR1                                                                   180
     ATC AAC TGC AAA GCA AGT CAG AAT ATT AAC AGG TAC TTA AAC TGG TAC CAG CAA AAG CTT
      I   N   C  |K   A   S   Q   N   I   N   R   Y   L   N |W   Y   Q   Q   K   L
```

TABLE 16-continued

```
181                             CDR2                                     240
    GGA GAA GCT CCC AAA CTC CTG ATA TAT AAT GCA AAC AGT TTG CAA ACG GGC ATC CCA TCA
     G   E   A   P   K   L   L   I   Y  N   A   N   S   L   Q   T   G   I   P   S

241 CGG TTC AGT GGC AGT GGA TCT GGT ACT GAT TTC ACA CTC ACC ATC AGC AGC CTG CAG CCT 300
     R   F   S   G   S   G   S   G   T   D   F   T   L   T   I   S   S   L   Q   P

301                                                 CDR3                 360
    GAA GAT GTT GCC ACA TAT TTC TGC TTG CAG CAT AAT AGT TGG CCG TAC ACG TTT GGA GCT
     E   D   V   A   T   Y   F   C  L   Q   H   N   S   W   P   Y   T   F   G   A

361 GGG ACC AAG CTG GAA CTG AAA                                          420
     G   T   K   L   E   L   K
```

Clone 699 H Chain (SEQ ID NO: 86)

TABLE 17

```
1   ATG GAA TGG AAC TGG GTC TTT CTC TTC CTC CTG TCA GTA ACT GCA GGA GTC CAC TCC CAG  60
     M   E   W   N   W   V   F   L   F   L   L   S   V   T   A   G   V   H   S   Q

61  GTC CAG CTG CAG CAG TCT GGA GCT GAG CTG ACA AAG CCT GGC TCT TCA GTG AAG ATT TCC 120
     V   Q   L   Q   Q   S   G   A   E   L   T   K   P   G   S   S   V   K   I   S

121                                 CDR1                                 180
    TGC AAG GCT TCT GGC TAC ACC TTT ACC AGC TAC GAT ATA AGC TGG ATA AAG CAG AGG CCT
     C   K   A   S   G   Y   T   F   T  S   Y   D   I   S   W   I   K   Q   R   P

181                             CDR2                                     240
    GGA CAG GCC CTT GAG TGG ATT GGA GCT ATT AAT CCA GGA AGT GGA GGT ACA GGC TAC AAT
     G   Q   A   L   E   W   I   G  A   I   N   P   G   S   G   G   T   G   Y   N

241 GAG AAG TTC AAG GGC AAG GCC ACA TTG ACT GTA GAC AAA TCC TCC AGC ACA GCC TTC ATG 300
    E   K   F   K   G   K  A   T   L   T   V   D   K   S   S   S   T   A   F   M

301                                                             CDR3     360
    CAA CTC AGC AGC CTC ACA CCT GAG GAC ACT GCG GTC TAT TAC TGT GCA AGA ATC CAC GGA
     Q   L   S   S   L   T   P   E   D   T   A   V   Y   Y   C   A   R  I   H   G 361                                                                      420
    GGG TAT AGA TAT TGG TTT GCT TAC TGG GGC CAA GGC CAA GGC ACT CTG GTC TCT TCA
    G   Y   R   Y   W   F   A   Y  W   G   Q   G   Q   G   T   L   V   S   S
```

Clone 699 L Chain (SEQ ID NO: 87)

TABLE 18

```
1   ATG GAT TTT CAG GTG CAG AGT TTC AGC CTC CTG CTA ATC AGT ATC ACA GTC ATA GTG TCC 120
     M   D   F   Q   V   Q   S   F   S   L   L   L   I   S   I   T   V   I   V   S

61  AGT GGA GAA ATT GTG CTC ACC CAG TCT CCA ACA ACC ATG GCT GCA TCT CCA GGA GAG AAG 180
     S   G   E   I   V   L   T   Q   S   P   T   T   M   A   A   S   P   G   E   K

121                     CDR1                                             240
    GTC ACC ATC ACC TGC CGT GCC AGC TCA AGT GTA AGC TAC ATG CAC TGG TTC CAG CAG AAG
     V   T   I   T   C  R   A   S   S   S   V   S   Y   M   H  W   F   Q   Q   K

181                                 CDR2                                 300
    TCA GGC ACC TCC CCC AAA CCC TGG ATT TAT GAC ACA TCC AAG CTC GCT TCT GGA GTC CCA
     S   G   T   S   P   K   P   W   I   Y  D   T   S   K   L   A   S  G   V   P

241 GAT CGC TTC AGT GGC AGT GGG TCT GGG ACC TCT TAT TCT CTC ACA ATC AGC TCC ATG GAG 360
     D   R   F   S   G   S   G   S   G   T   S   Y   S   L   T   I   S   S   M   E
```

TABLE 18-continued

| 301 | GCT | GAA | GAT | GCT | GCT | ACT | TAT | TAC | TGT | CDR3 CTG CAG AGG AGT AGT TAC CCA CCA ACG | TTT | GGA | 420 |
|---|---|---|---|---|---|---|---|---|---|---|---|---|---|
| | A | E | D | A | A | T | Y | Y | C | L Q R S S Y P P T | F | G | |
| 361 | GCT | GGG | ACC | AAG | CTG | GAA | CTG | AAA | | | | | 480 |
| | A | G | T | K | L | E | L | K | | | | | |

Clone 1052 H Chain (SEQ ID NO: 94)

TABLE 19

| 1 | ATG GCT GTC CTG GTG CTA TTG CTC TGC CTG GTG ACA TTT CCA AGC TGT GTC CTG TCC CAG | 60 |
|---|---|---|
| | M A V L L L C L V T F P S C V L S Q | |
| 61 | GTG CAG CTG AAG GAG TCA GGA CCT GGC TTG ATG CAG CCC TCA GAG ACC CTG TCC CTC ACC | 120 |
| | V Q L K E S G P G L M Q P S E T L S L T | |
| 121 | | 180 |
| | TGC ACT GTC TCT GGC TTC TCA CTC ACC <u>CDR1</u> AGC AAT GGT GTA GGC TGG GTT CGA CAA CCT CTA | |
| | C T V S G F S L T S N G V G W V R Q P L | |
| 181 | | 240 |
| | GGA AAG GGT TTG GTG TGG ATG GGA <u>CDR2</u> ACA ATA TGG ACT GGT GGA GGT ACA AAT TAT AAT TCA | |
| | G K G L V W M G T I W T G G G T N Y N S | |
| 241 | GGT GTC CAA TCC CGA CTG AGC ATC AGC AGG GAA ACC TCC AAG AGC CAA GTG TTC TTA AAA | 300 |
| | G V Q S R L S I S R D T S K S Q V F L K | |
| 301 | | 360 |
| | ATG AAC AGT CTG CAA CCT GAA GAC ACA GGC ACT TAC TAC TGT GCC AGA GAG <u>CDR3</u> TAT ATG GGT | |
| | M N S L Q P E D T G T Y Y C A R E Y M G | |
| 361 | TTT GAT TAC TGG GGC CAA GGA GTC ATG GTC ACA GTC TCC TCA | 420 |
| | F D Y W G Q G V M V T V S S | |

Clone 1052 L Chain (SEQ ID NO: 95)

TABLE 20

| 1 | ATG GAG TTA ATC AGT CAG GTC TTC GTA TTT CTG CTG CTC TGG TTG TCT GGG GTT TAT GGG | 120 |
|---|---|---|
| | M E L I S Q V F V F L L L W L S G V Y G | |
| 61 | AAT ACT GTG ATG ACC CAG TCT CCC ACA TCT ATG TTC ACA TCA GTA GGA GAC AGG GTT ACC | 180 |
| | N T V M T Q S P T S M F T S V G D R V T | |
| 121 | | 240 |
| | ATG AGC TGC <u>CDR1</u> AAG GCC AGT CAG AAT GTA GGT ATT AAT GTA GGC TGG TAC CAA CAG AAA ACA | |
| | M S C K A S Q N V G I N V G W Y Q Q K T | |
| 181 | | 300 |
| | GGG CAG TCT CCT AAA CGG CTT ATC TAC <u>CRD2</u> TGG GCA TCC AAC CGG GAC ACT GGG GTC CCT GAT | |
| | G Q S P K R L I Y W A S N R D T G V P D | |
| 241 | CGC TTC ACA GGC AGT GGA TCT GGG ACA GAT TTC ACT CTC ACC ATC AGC AAC ATG CAG GCT | 360 |
| | R F T G S G S G T D F T L T I S N M Q A | |
| 301 | | 420 |
| | GAA GAC CCA GCT ATT TAT TAC TGT <u>CDR3</u> CTG CAG CAT AAC TCC TAT CCT CGG ACG TTC GGT GGA | |
| | E D P A I Y Y C L Q H N S Y P R T F G G | |
| 361 | GGC ACC AAG CTG GAA TTG AAA | 480 |
| | G T K L E L K | |

Clone 1105 H Chain (SEQ ID NO: 102)

TABLE 21

```
  1  ATG GCT GTC CTG GTG CTA TTG CTC TGC CTG GTG ACA TTT CCA AGC TGT GTC CTG TCC CAG   60
      M   A   V   L   V   L   L   L   C   L   V   T   F   P   S   C   V   L   S   Q

61  GTG CAG CTG AAG GAG TCA GGA CCT GGC TTG ATG CAG CCC TCA GAG ACC CTG TCC CTC ACC  120
      V   Q   L   K   E   S   G   P   G   L   M   Q   P   S   E   T   L   S   L   T

121                                              CDR1                                180
     TGC ACT GTC TCT GGC TTC TCA CTA ACC |AGC AAT GGT GTA GGC| TGG GTT CGA CAA CCT CTA
      C   T   V   S   G   F   S   L   T  | S   N   G   V   G | W   V   R   Q   P   L

181                                    CDR2                                          240
     GGA AAG GGT TTG GTG TGG ATG GGA |ACA ATA TGG TCT GGT GGA GGT ACA AAC TAT AAT TCA
      G   K   G   L   V   W   M   G  | T   I   W   S   G   G   G   T   N   Y   N   S

241  |GCT GTC CAA TCC| CGA CTG AGC ATC ACC AGG GAC ACC TCC AAG AGC CAA GTT TTC TTA AAA  300
     | A   V   Q   S | R   L   S   I   T   R   D   T   S   K   S   Q   V   F   L   K

301                                                              CDR3                360
     ATG AAC AGT CTG CAA CCT GAA GAC ACA GGC ACT TAC TAC TGT GCC AGA |GAG GAA AAG GGG
      M   N   S   L   Q   P   E   D   T   G   T   Y   Y   C   A   R | E   E   K   G

361  |TTT GCT TAC| TGG GGC CAA GGC ACT CTG GTC ACT GTC TCT TCA                          420
     | F   A   Y | W   G   Q   G   T   L   V   T   V   S   S
```

Clone 1105 L Chain (SEQ ID NO: 103)

TABLE 22

```
  1  ATG GAG TTA ATC AGT CAG GTC TTC GTA TTT CTG CTG CTC TGG TTG TCT GGG GTT TAT GGG  120
      M   E   L   I   S   Q   V   F   V   F   L   L   L   W   L   S   G   V   Y   G

61  AAC ATT GTG ATG ACC CAG TCT CCC ACA TCT ATG TCC ACA TCA GTA GGA GAC AGG GTT ACC  180
      N   I   V   M   T   Q   S   P   T   S   M   S   T   S   V   G   D   R   V   T

121                 CDR1                                                             240
     ATG AGC TGC |AAG GCC AGT CAG AAT GTA GGT ATT AAT GTA GGC| TGG TAC CAA CAG AAA ACA
      M   S   C  | K   A   S   Q   N   V   G   I   N   V   G | W   Y   Q   Q   K   T

181                                        CDR2                                      300
     GGG CAG TCT CCT AAA CGG CTT ATC TAC |TGG GCA TCC AAC CGG GAC ACT| GGG GTC CCT GAT
      G   Q   S   P   K   R   L   I   Y  | W   A   S   N   R   D   T | G   V   P   D

241  CGC TTC ACA GGC AGT GGA TCT GGG ACA GAT TTC ACT CTC ACC ATC AGC AAC ATG CAG GCT  360
      R   F   T   G   S   G   S   G   T   D   F   T   L   T   I   S   N   M   Q   A

301                                      CDR3                                        420
     GAA GAC CCA GCT ATT TAT TAC TGT |CTG CAG CAT AAC TCC TAT CCT CGG GCG| TTC GGT GGA
      E   D   P   A   I   Y   Y   C  | L   Q   H   N   S   Y   P   R   A | F   G   G

361  GGC ACC AAG CTG GAA TTG AGA                                                      480
      G   T   K   L   E   L   R
```

9. Cancer Testing Method Involving Measurement of Amount of TMEM-180

1) ELISA Protocol

First, the following indicates the protocol for the ELISA method used in the following examples.
(Reagents)
The following reagents were used.
96-well plate: C8 Maxi Breakapart (Nunc Co., Ltd. #473768)
Plate washing solution: PBS/0.05% TWEEN 20
Blocking solution: PBS/1% BSA
Antibody diluent: PBS/0.05% TWEEN 20/1% BSA Primary antibody: IgM 98 (hybridoma culture supernatant)
Secondary antibody: Polyclonal rabbit anti-rat immunoglobulins/HRP
(Dako #P0450)
Color developing solution: 1-Step Slow TMB-ELISA (Thermo Fisher Scientific Inc. #34024)
Stopping solution: 2N $H_2SO_4$ Procedure Testing was carried out according to the procedure indicated below.

(i) Antigen Immobilization

Antibody culture supernatant or human serum (diluted 1/10 and 1/50) was added to a 96-well plate at 50 μL/well followed by incubating overnight at 4° C.

(ii) Blocking

The antigen-immobilized plate was repeatedly washed five times with plate washing solution at 200 μL/well. Blocking was then carried out with blocking solution at 200 μL/well followed by incubating for 1 hour at room temperature.

(iii) Primary Antibody Reaction

The antigen-immobilized plate was repeatedly washed five times with plate washing solution at 200 μL/well. IgM 98 antibody solution was then added at 100 μL/well and 10 μg/mL followed by incubating for 1 hour at room temperature.

(iv) Secondary Antibody Reaction

The antigen-immobilized plate was repeatedly washed five times with plate washing solution at 200 μL/well. Secondary antibody diluted 4000-fold was added at 100 μL/well followed by incubating for 1 hour at room temperature.

(v) Color Development and Stopping of the Reaction

The antigen-immobilized plate was repeated washed five times with plate washing solution at 200 μL/well. Color developing solution was then added at 100 μL/well followed by incubating for 15 minutes at room temperature. Stopping solution was then added at 100 μL/well.

(vi) Measurement

Absorbance at 450 nm was measured after stopping the reaction.

2) Measurement of Amount of TMEM-180 Protein in Cancer Cell Culture Supernatant Colon cancer cell line DLD-1 that forcibly expresses TMEM-180, the parent line and the TMEM-180 knockdown line were cultured and washed with PBS after nearly reaching confluency. The medium was replaced with serum-free DMEM medium followed by culturing overnight and recovering the supernatant on the following day. This supernatant was used as sample antigen and immobilized on a 96-well plate followed by carrying out ELISA according to the method described in section 1). In addition, a similar experiment was conducted on brain tumor cell line LN229.

Figure 9:
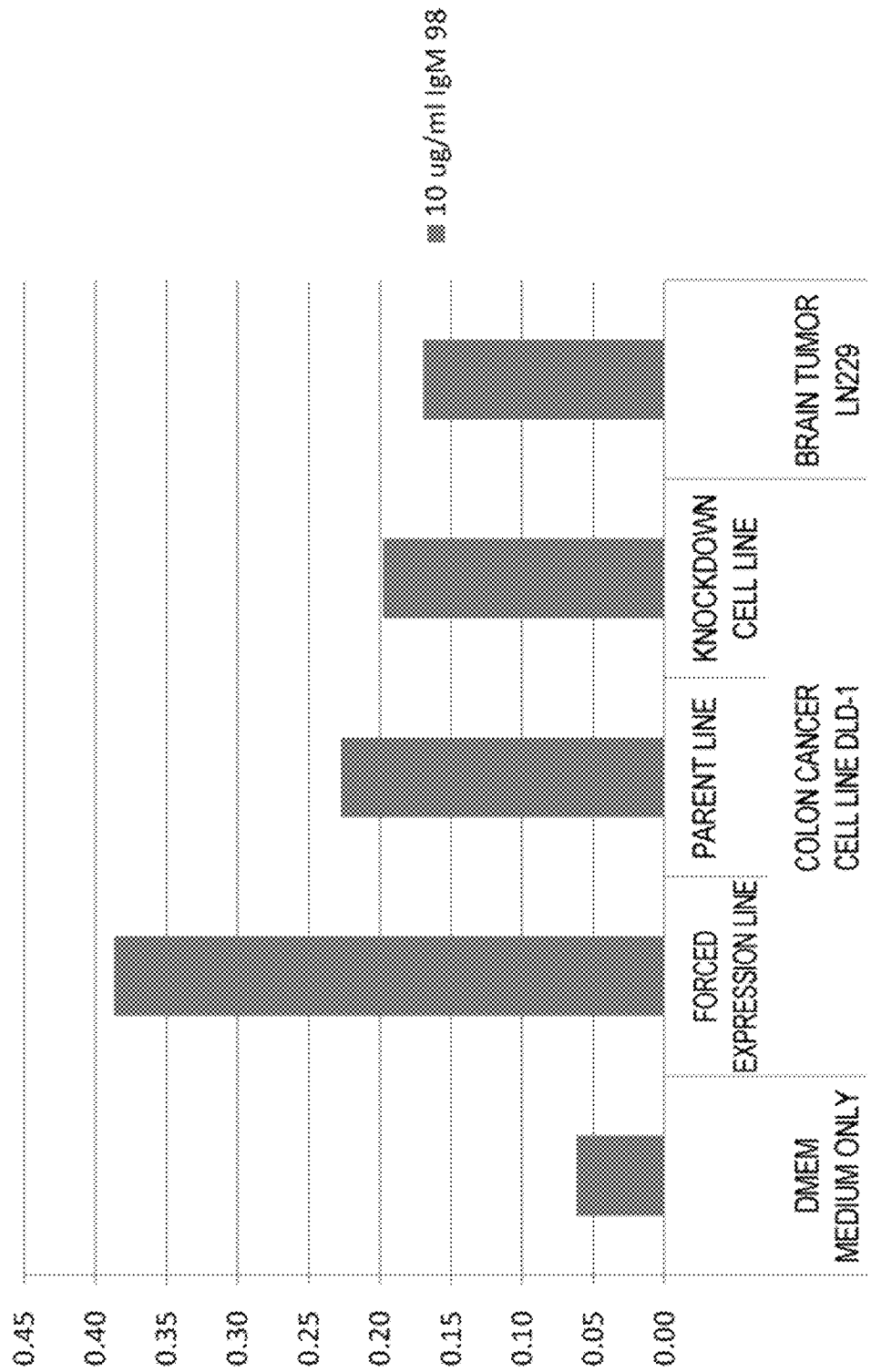
FIG. 9 indicates the results of measuring TMEM-180 protein concentration in culture supernatants of cancer cells.

The results are shown in FIG. 9. In comparison with the normal control (medium only), TMEM-180 exhibited high levels in all of the samples. The forced expression cell line, parent cell line and knockdown cell line demonstrated high levels in that order in colon cancer DLD-1. High levels were also demonstrated in brain tumor cells.

3) Measurement of Amount of TMEM-180 Protein in Plasma of Stage IV Colon Cancer Patients After diluting human plasma collected in EDTA (formed of four samples from stage IV patients and normal subjects) at dilution factors of 1/10 and 1/50, the plasma was used as sample antigen and immobilized on a 96-well plate followed by carrying out ELISA according to the method described in section 1).

Figure 10:
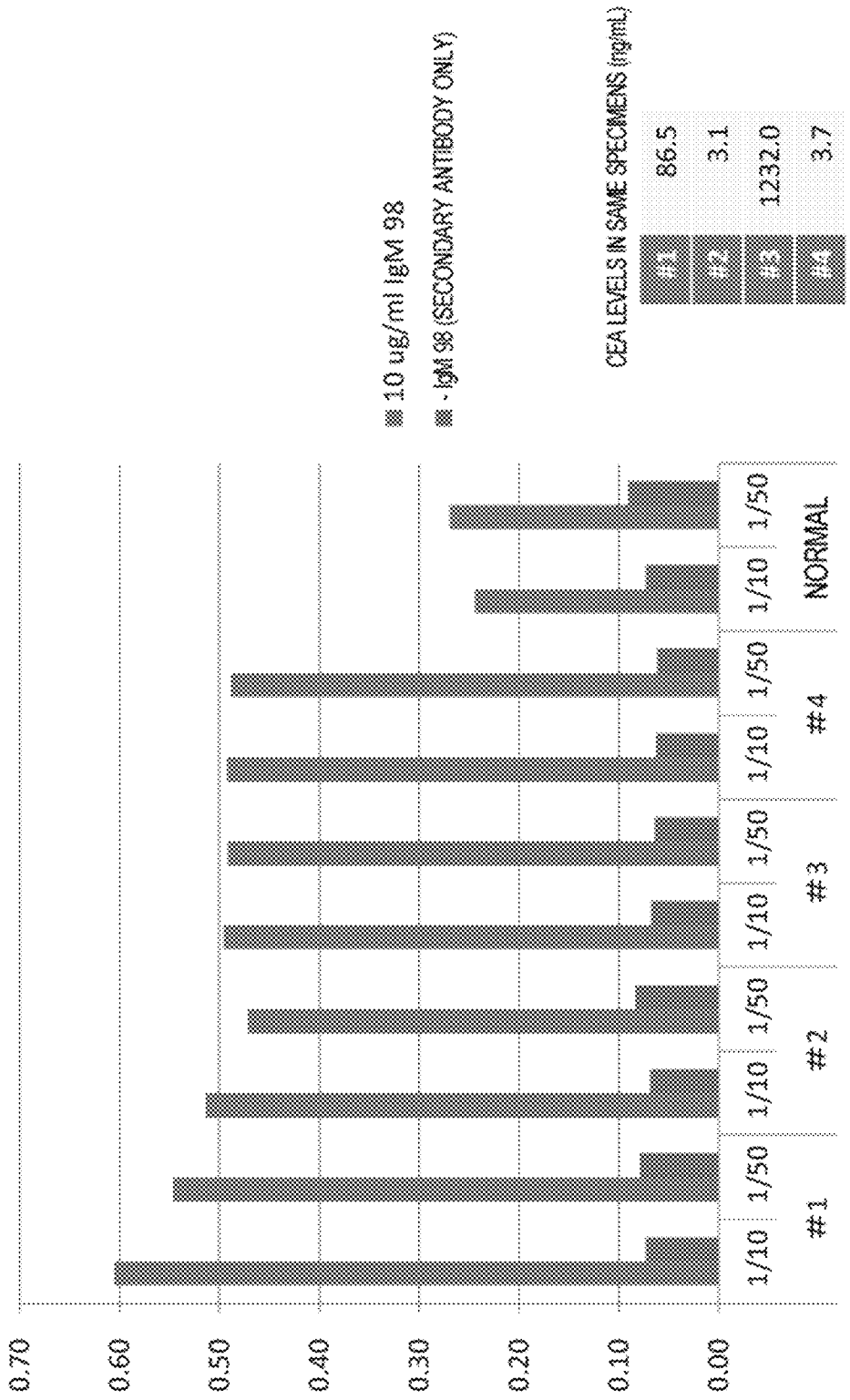
FIG. 10 indicates the results of measuring plasma TMEM-180 protein concentrations in four stage IV colon cancer patients. In addition, the table shown to the right of the graph indicates the results of measuring CEA levels in specimens collected from the same patients.

The results are shown in FIG. 10. In comparison with normal plasma, high levels were demonstrated in all of the patient samples. In addition, plasma TMEM-180 levels were positive (higher than normal) even in patients #2 and #4 who were negative for CEA.

4) Measurement of Amount of TMEM-180 Protein in Plasma of Stage III Colon Cancer Patients Before and After Surgery The amount of TMEM-180 protein in the plasma of stage III colon cancer patients before and after surgery was measured using the same method as section 3).

Figure 11:
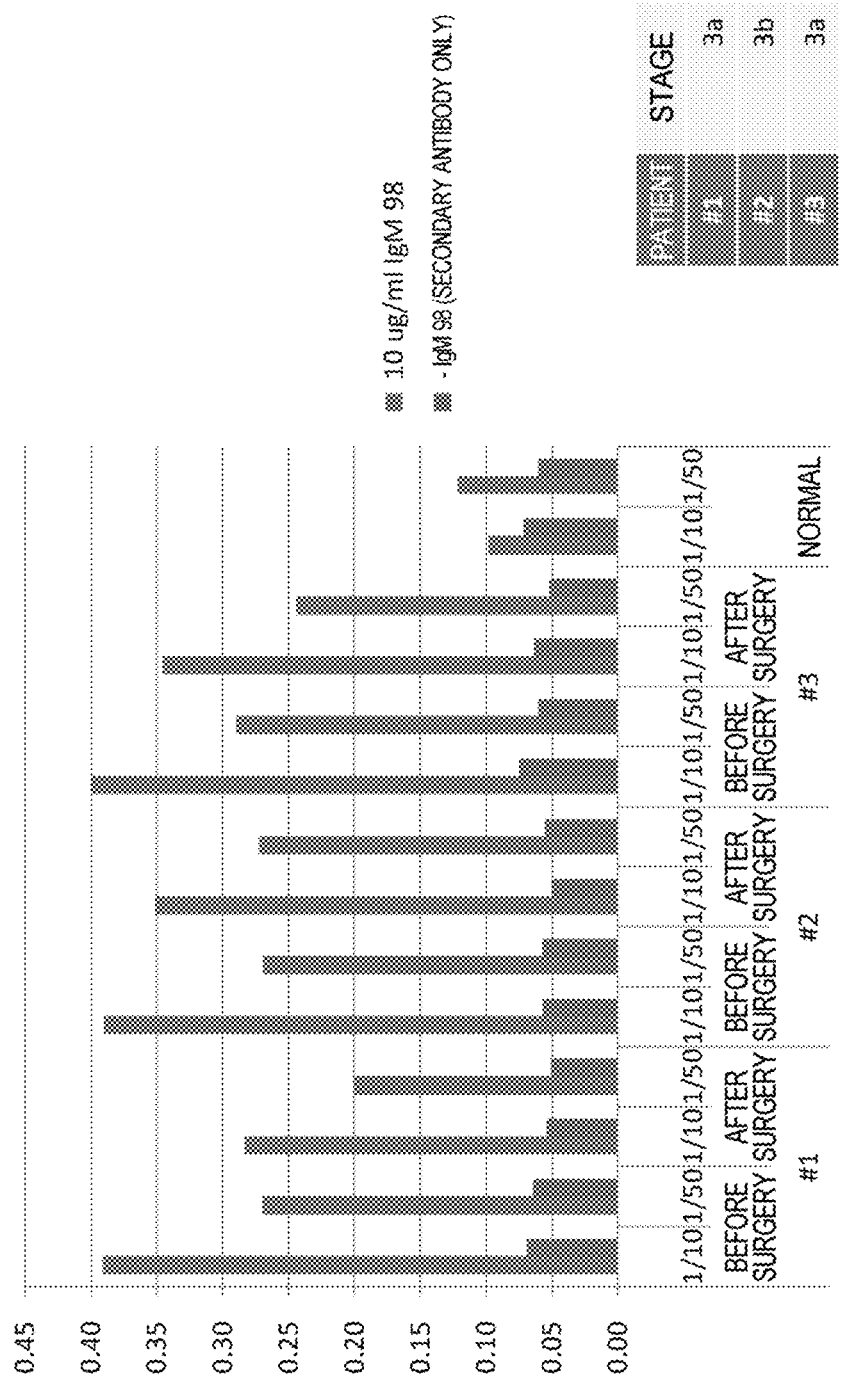
FIG. 11 indicates the results of measuring plasma TMEM-180 protein concentrations before and after surgery in three stage III colon cancer patients.

The results are shown in FIG. 11. TMEM-180 levels decreased after surgery in comparison with before surgery in all of the patients.

5) The amount of TMEM-180 protein and the colon cancer tumor marker, CEA, were measured in the plasma of stage III, II, IV and Ma colon cancer patients before and after surgery and at the time of recurrence. Measurement of TMEM-180 was carried out by sandwich ELISA using clone 669 and clone 1361. The average of the levels of TMEM-180 in the normal plasma of 8 subjects as measured by ELISA in the same manner as in the case of the patient samples was used for the TMEM-180 cutoff value. The normal value used at the National Cancer Center Japan was used for the CEA cutoff value.

Figure 12:
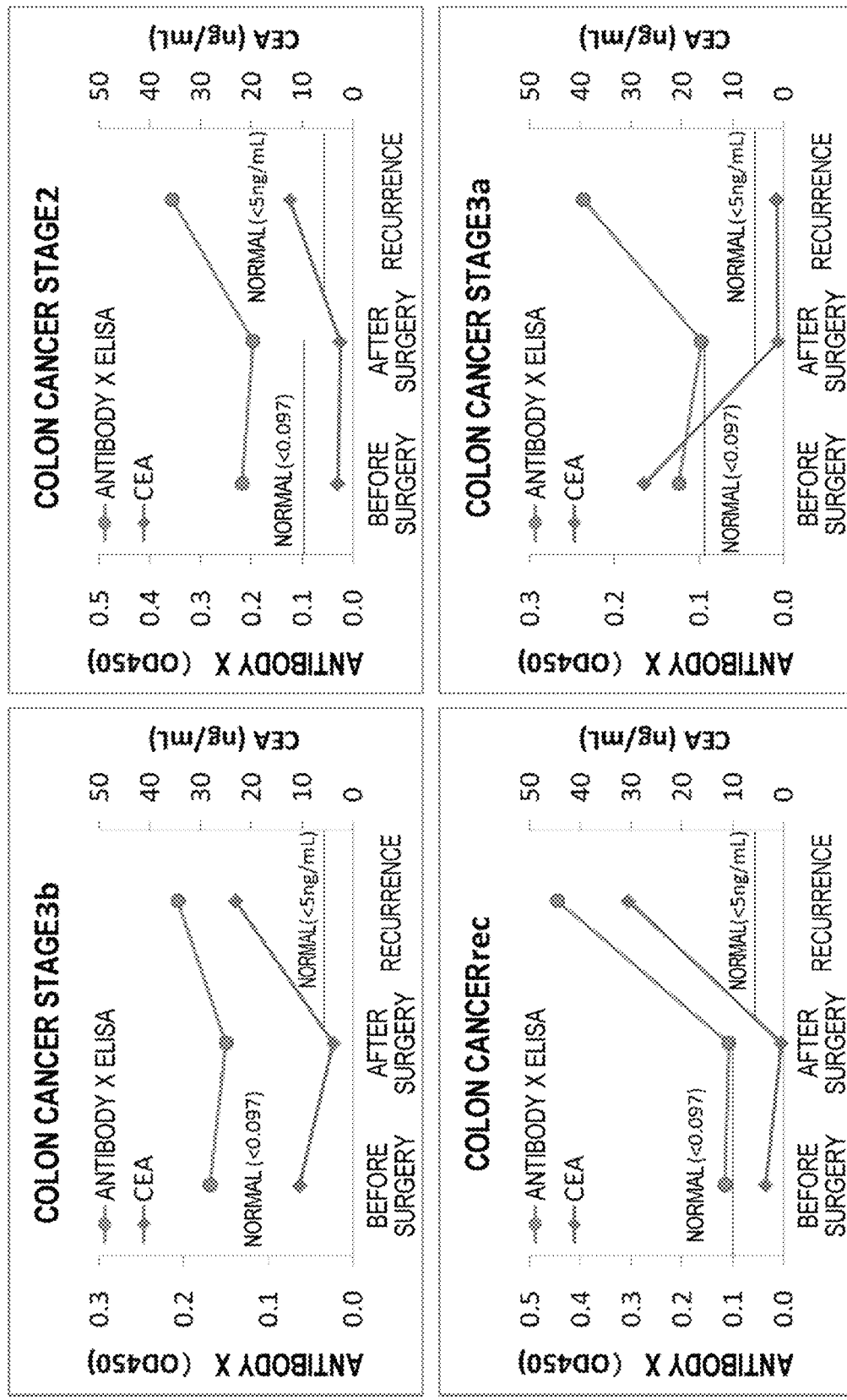
FIG. 12 indicates the results of measuring plasma TMEM-180 protein concentrations and CEA concentrations before surgery, after surgery and at the time of recurrence in colon cancer patients at various stages.

The results are shown in FIG. 12. Stage II patients were positive for TMEM-180 despite being negative for CEA level prior to surgery. In addition, although stage Ma patients remained negative for CEA even after confirmation of recurrence by CT, TMEM-180 levels increased again.

Furthermore, the protocol of the sandwich ELISA procedure used in the example of section 5) is indicated below.

(Reagents)

The following reagents were used.

96-well plate: Maxisoap (Nunc Co., Ltd. #442404)

0.1 M phosphate buffer

Plate washing solution: 10 mM TBS (pH 7.2)/0.05% TWEEN 20/140 mM NaCl

Blocking solution: 10 mM TBS (pH 7.2)/0.05% TWEEN 20/140 mM NaCl/1% BSA

Diluent: 10 mM TBS (pH 7.2)/0.05% TWEEN 20/140 mM NaCl/1% BSA

Immobilized antibody: Clone 669

Labeled antibody: Clone 1361

Streptavidin HRP (Vector Laboratories #SA-5004)

Color developing solution: 1-Step Slow TMB-ELISA (Thermo Fisher Scientific Inc. #34024)

Stopping solution: 2 N $H_2SO_4$ (Procedure)

Measurement was carried out according to the procedure indicated below.

(i) Immobilization

Immobilized antibody clone 669 diluted with 0.1 M phosphate buffer was added to a 96-well plate at 50 μl/well followed by incubating overnight at 4° C.

(ii) Blocking

The antibody-immobilized plate was repeatedly washed three times with plate washing solution at 200 μL/well. Blocking was carried out with blocking solution at 200 μL/well followed by incubating for 30 minutes or more at room temperature.

(iii) Addition of Antigen

The antibody-immobilized plate was repeatedly washed three times with plate washing solution at 200 μL/well. A measurement sample was added to the antibody-immobilized plate at 50 μL/well followed by incubating for 1 hour at room temperature.

(iv) Labeled Antibody Reaction

The antibody-immobilized plate was repeatedly washed three times with plate washing solution at 200 μL/well. Biotin-labeled clone 1361 prepared using an established method was added to the 96-well plate at 50 μL/well after diluting with diluent followed by incubating for 1 hour at room temperature.

(v) Streptavidin HRP Reaction

The antibody-immobilized plate was repeatedly washed three times with plate washing solution at 200 μL/well. Streptavidin HRP diluent was added at 50 μL/well followed by incubating for 1 hour at room temperature.

(vi) Color Development and Stopping of the Reaction

The antibody-immobilized plate was repeatedly washed three times with plate washing solution at 200 μL/well. Color developing solution was added at 100 μL/well followed by incubating for 20 minutes at room temperature. Stopping solution was added at 50 μL/well.

(vii) Measurement

Absorbance at 450 nm was measured after stopping the reaction.

Sequence Listing Free Text

SEQ ID NOs: 1 to 3 respectively indicate the amino acid sequences of clone 98 heavy chain CDR1 to CDR3.

SEQ ID NOs: 4 to 6 respectively indicate the amino acid sequences of clone 98 light chain CDR1 to CDR3.

SEQ ID NOs: 7 to 9 respectively indicate the amino acid sequences of clone 101 heavy chain CDR1 to CDR3.

SEQ ID NOs: 10 to 12 respectively indicate the amino acid sequences of clone 101 light chain CDR1 to CDR3.

SEQ ID NOs: 13 and 14 respectively indicate the amino acid sequences of the heavy chain variable region and light chain variable region of clone 98.

SEQ ID NOs: 15 and 16 respectively indicate the amino acid sequences of the heavy chain variable region and light chain variable region of clone 101.

SEQ ID NO: 17 indicates the amino acid sequence of human TMEM-180 protein.

SEQ ID NOs: 18 to 21 respectively indicate primers (i) to (iv) for producing immunizing antigen 1.

SEQ ID NOs: 22 to 25 respectively indicate primers (i) to (iv) for producing immunizing antigen 2.

SEQ ID NOs: 26 to 31 indicate primers used for cloning an anti-TMEM-180 antibody.

SEQ ID NOs: 40 to 42 respectively indicate the amino acid sequences of clone 212 heavy chain CDR1 to CDR3.

SEQ ID NOs: 43 to 45 respectively indicate the amino acid sequences of clone 212 light chain CDR1 to CDR3.

SEQ ID NOs: 46 and 47 respectively indicate the amino acid sequences of the heavy chain variable region and light chain variable region of clone 212.

SEQ ID NOs: 48 to 50 respectively indicate the amino acid sequences of clone 129 heavy chain CDR1 to CDR3.

SEQ ID NOs: 51 to 53 respectively indicate the amino acid sequences of clone 129 light chain CDR1 to CDR3.

SEQ ID NOs: 54 and 55 respectively indicate the amino acid sequences of the heavy chain variable region and light chain variable region of clone 129.

SEQ ID NOs: 56 to 58 respectively indicate the amino acid sequences of clone 382 heavy chain CDR1 to CDR3.

SEQ ID NOs: 59 to 61 respectively indicate the amino acid sequences of clone 382 light chain CDR1 to CDR3.

SEQ ID NOs: 62 and 63 respectively indicate the amino acid sequences of the heavy chain variable region and light chain variable region of clone 382.

SEQ ID NOs: 64 to 66 respectively indicate the amino acid sequences of clone 1361 heavy chain CDR1 to CDR3.

SEQ ID NOs: 67 to 69 respectively indicate the amino acid sequences of clone 1361 light chain CDR1 to CDR3.

SEQ ID NOs: 70 and 71 respectively indicate the amino acid sequences of the heavy chain variable region and light chain variable region of clone 1361.

SEQ ID NOs: 72 to 74 respectively indicate the amino acid sequences of clone 669 heavy chain CDR1 to CDR3.

SEQ ID NOs: 75 to 77 respectively indicate the amino acid sequences of clone 669 light chain CDR1 to CDR3.

SEQ ID NOs: 78 and 79 respectively indicate the amino acid sequences of the heavy chain variable region and light chain variable region of clone 669.

SEQ ID NOs: 80 to 82 respectively indicate the amino acid sequences of clone 699 heavy chain CDR1 to CDR3.

SEQ ID NOs: 83 to 85 respectively indicate the amino acid sequences of clone 699 light chain CDR1 to CDR3.

SEQ ID NOs: 86 and 87 respectively indicate the amino acid sequences of the heavy chain variable region and light chain variable region of clone 699.

SEQ ID NOs: 88 to 90 respectively indicate the amino acid sequences of clone 1052 heavy chain CDR1 to CDR3.

SEQ ID NOs: 91 to 93 respectively indicate the amino acid sequences of clone 1052 light chain CDR1 to CDR3.

SEQ ID NOs: 94 and 95 respectively indicate the amino acid sequences of the heavy chain variable region and light chain variable region of clone 1052.

SEQ ID NOs: 96 to 98 respectively indicate the amino acid sequences of clone 1105 heavy chain CDR1 to CDR3.

SEQ ID NOs: 99 to 101 respectively indicate the amino acid sequences of clone 1105 light chain CDR1 to CDR3.

SEQ ID NOs: 102 and 103 respectively indicate the amino acid sequences of the heavy chain variable region and light chain variable region of clone 1105.

SEQ ID NOs: 104 to 150 indicate the amino acid sequences of TMEM-180-derived peptides binding to HLA type A2 as predicted by HLA Peptide Binding Predictions.

SEQ ID NOs: 151 to 170 indicate the amino acid sequences of TMEM-180-derived peptides binding to HLA type A24 as predicted by HLA Peptide Binding Predictions.

What is claimed is:

1. An anti-transmembrane protein 180 (TMEM-180) monoclonal antibody or an antigen-binding fragment thereof, wherein the antibody and the antigen-binding fragment thereof comprise the following CDR sequences:

```
Heavy chain CDR1:
                                 (SEQ ID NO: 96)
SNGVG;

Heavy chain CDR2:
                                 (SEQ ID NO: 97)
TIWSGGGTNYNSAVQS;

Heavy chain CDR3:
                                 (SEQ ID NO: 98)
EEKGFAY;

Light chain CDR1:
                                 (SEQ ID NO: 99)
KASQNVGINVG;

Light chain CDR2:
                                 (SEQ ID NO: 100)
WASNRDT;
and Light chain CDR3:
                                 (SEQ ID NO: 101)
LQHNSYPRA.
```

2. The anti-TMEM-180 monoclonal antibody or the antigen-binding fragment thereof according to claim 1, further comprising a substance having anticancer activity bound thereto.

3. The anti-TMEM-180 monoclonal antibody according to claim 1, further comprising an N-linked oligosaccharide bound to the Fc region, wherein fucose is not bound to N-acetylglucosamine on the reducing end of the N-linked oligosaccharide.

4. An isolated nucleic acid which encodes the anti-TMEM-180 monoclonal antibody or the antigen-binding fragment thereof according to claim 1.

5. An isolated expression vector containing the nucleic acid according to claim 4.

6. An isolated transformant containing the expression vector according to claim 5.

7. A kit comprising the anti-TMEM-180 monoclonal antibody or the antigen-binding fragment thereof according to claim 1.

8. A composition comprising the anti-TMEM-180 monoclonal antibody or the antigen-binding fragment thereof according to claim 1, and a pharmaceutically acceptable carrier or pharmaceutically acceptable additive.

9. A method for producing the anti-TMEM-180 monoclonal antibody or the antigen-binding fragment thereof according to claim 1, which comprises
   expressing the anti-TMEM-180 monoclonal antibody or the antigen-binding fragment in an isolated transformant containing an expression vector that encodes the anti-TMEM-180 antibody or the antigen-binding fragment; and
   recovering the anti-TMEM-180 monoclonal antibody or the antigen-binding fragment thereof of claim 1.

10. An assay method which comprises detecting or measuring the amount of a TMEM-180 protein in a sample collected from a subject, wherein the amount of the TMEM-180 protein is measured by immunoassay using the anti-TMEM-180 monoclonal antibody or the antigen-binding fragment thereof according to claim 1.

11. A method of treating a cancer in a subject who has the cancer which comprises administering to the subject the anti-TMEM-180 monoclonal antibody or antigen binding fragment thereof according to claim 1, wherein the cancer expresses TMEM-180.

12. The method according to claim 11, wherein the cancer is colon cancer.

13. An anti-transmembrane protein 180 (TMEM-180) monoclonal antibody or an antigen-binding fragment thereof, wherein the antibody and the antigen-binding fragment thereof comprise the following CDR sequences:

Heavy chain CDR1: SNGVG (SEQ ID NO: 96);

Heavy chain CDR2: TIWSGGGTNYNSAVQS (SEQ ID NO: 97);

Heavy chain CDR3: EEKGFAY (SEQ ID NO: 98);

Light chain CDR1: KASQNVGINVG (SEQ ID NO: 99);

Light chain CDR2: WASNRDT (SEQ ID NO: 100); and

Light chain CDR3: LQHNSYPRA (SEQ ID NO: 101)

wherein said anti-transmembrane protein 180 (TMEM-180) monoclonal antibody is an IgM antibody.

* * * * *